United States Patent
Starczynowski et al.

(10) Patent No.: US 11,254,667 B2
(45) Date of Patent: Feb. 22, 2022

(54) SUBSTITUTED IMIDAZO[1,2-A]PYRIDINES AS IRAK 1/4 AND FLT3 INHIBITORS

(71) Applicants: CHILDREN'S HOSPITAL MEDICAL CENTER, Cincinnati, OH (US); THE UNITED STATES OF AMERICA, AS REPRESENTED BY THE SECRETARY, DEPARTMENT OF HEALTH AND HUMAN SERVICES, Bethesda, MD (US)

(72) Inventors: Daniel T. Starczynowski, Cincinnati, OH (US); Craig J. Thomas, Gaithersburg, MD (US); Garrett Rhyasen, Burlington, MA (US); Katelyn Melgar, Cincinnati, OH (US); Morgan MacKenzie Walker, New Haven, CT (US); Jian-kang Jiang, Columbia, MD (US)

(73) Assignees: CHILDREN'S HOSPITAL MEDICAL CENTER, Cincinnati, OH (US); THE UNITED STATES OF AMERICA AS REPRESENTED BY THE SECRETARY, DEPT. OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/326,571

(22) PCT Filed: Aug. 16, 2017

(86) PCT No.: PCT/US2017/047088
§ 371 (c)(1),
(2) Date: Feb. 19, 2019

(87) PCT Pub. No.: WO2018/038988
PCT Pub. Date: Mar. 1, 2018

(65) Prior Publication Data
US 2020/0270242 A1 Aug. 27, 2020

Related U.S. Application Data

(60) Provisional application No. 62/375,965, filed on Aug. 17, 2016.

(51) Int. Cl.
*A61K 31/437* (2006.01)
*C07D 471/04* (2006.01)
*A61P 35/02* (2006.01)

(52) U.S. Cl.
CPC ............ *C07D 471/04* (2013.01); *A61P 35/02* (2018.01)

(58) Field of Classification Search
CPC ............................ A61K 31/437; C07D 471/04
USPC .......................................... 514/300; 546/121
See application file for complete search history.

(56) References Cited

U.S. PATENT DOCUMENTS

| | | | |
|---|---|---|---|
| 4,522,811 A | 6/1985 | Eppstein et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 8,288,377 B2 | 10/2012 | Storck et al. |
| 9,168,257 B2 | 10/2015 | Starczynowski et al. |
| 9,382,239 B2 | 7/2016 | Gray et al. |

(Continued)

FOREIGN PATENT DOCUMENTS

| WO | 9605309 A2 | 2/1996 |
| WO | 0240680 A2 | 5/2002 |

(Continued)

OTHER PUBLICATIONS

U.S. Appl. No. 16/339,692, filed Apr. 4, 2019.

(Continued)

*Primary Examiner* — Douglas M Willis
(74) *Attorney, Agent, or Firm* — Morgan, Lewis & Bockius LLP

(57) ABSTRACT

Some embodiments of the invention include inventive compounds (e.g., compounds of Formula (I)). Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer or blood disorders). Further embodiments include methods for making the inventive compounds. Additional embodiments of the invention are also discussed herein.

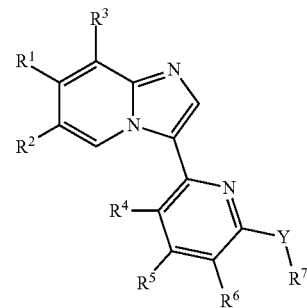

Formula (I)

38 Claims, 24 Drawing Sheets

(56) References Cited

U.S. PATENT DOCUMENTS

| | | | |
|---|---|---|---|
| 9,504,706 | B2 | 11/2016 | Starczynowski et al. |
| 9,708,324 | B2 | 7/2017 | Chen et al. |
| 9,775,844 | B2 | 10/2017 | Kutok et al. |
| 9,815,836 | B2 | 11/2017 | Chen et al. |
| 10,059,708 | B2 | 8/2018 | Shilatifard et al. |
| 10,160,753 | B2 | 12/2018 | Gummadi et al. |
| 10,246,456 | B2 | 4/2019 | Chan et al. |
| 2007/0087392 | A1 | 4/2007 | Somers et al. |
| 2013/0231328 | A1 | 9/2013 | Harriman et al. |
| 2013/0280264 | A1 | 10/2013 | Davila |
| 2014/0309249 | A1 | 10/2014 | Gray et al. |
| 2014/0350070 | A1 | 11/2014 | Starczynowski et al. |
| 2015/0284405 | A1 | 10/2015 | Trzupek et al. |
| 2016/0193216 | A1 | 7/2016 | Harriman et al. |
| 2017/0035881 | A1 | 2/2017 | Lannutti et al. |

FOREIGN PATENT DOCUMENTS

| | | | |
|---|---|---|---|
| WO | 03030902 | A1 | 4/2003 |
| WO | 2007047907 | A2 | 4/2007 |
| WO | 2008030579 | A2 | 3/2008 |
| WO | 2013006443 | A2 | 1/2013 |
| WO | 2013042137 | A1 | 3/2013 |
| WO | 2015076800 | A1 | 5/2015 |
| WO | 2016138473 | A1 | 9/2016 |
| WO | 2017075054 | A1 | 5/2017 |

OTHER PUBLICATIONS

U.S. Appl. No. 14/284,521, filed May 22, 2014.
U.S. Appl. No. 14/842,049, filed Sep. 1, 2015.
U.S. Appl. No. 15/288,402, filed Oct. 7, 2016.
U.S. Appl. No. 15/765,824, filed Apr. 4, 2018.
Kristinsson et al., "Chronic immune stimulation might act as a trigger for the development of acute myeloid leukemia or myelodysplastic syndromes," Journal of Clinical Oncology 29(21):2897-2903, Jul. 20, 2011.
Langer et al., "New methods of drug delivery," Science 249(4976):1527-1533, Sep. 28, 1990.
Martin et al., "Limited engraftment of low-risk myelodysplastic syndrome cells in NOD/SCID gamma-C chain knockout mice," Leukemia 24(9):1662-1664, Sep. 2011.
Marur et al., "Head and Neck Cancer: Changing Epidemiology, Diagnosis, and Treatment," Mayo Clinic Proceedings 83(4):489-501, Apr. 1, 2008.
Matsuoka et al., "Lenalidomide induces cell death in an MDS-derived cell line with deletion of chromosome 5q by inhibition of cytokinesis," Leukemia 24(4):748-755, Apr. 2010.
Miller Keane et al., "Miller-Keane Encyclopedia & Dictionary of Medicine, Nursing & Allied Health," 5th Ed. pp. 1651 and 1708. O'Toole (ed.). W.B. Saunders, Philadephia, PA. 1992.
Mor-Vaknin et al., "DEK in the Synovium of Patients With Juvenile Idiopathic Arthritis: Characterization of DEK Antibodies and Post-translational Modification of the DEK Autoantigen," Arthritis and Rheumatism 63(2):556-567, Feb. 2011.
Mor-Vaknin et al., "The DEK Nuclear Autoantigen Is a Secreted Chemotactic Factor," Molecular and Cellular Biology 26(24):9484-9496, Dec. 15, 2006.
Ngo et al., "Oncogenically Active MYD88 Mutations in Human Lymphoma," Nature 470(7332):115-119, Dec. 10, 2010.
Nimer, "Myelodysplastic syndromes," Blood 111(10):4841-4851, May 15, 2008.
O'Dwyer et al., "STI571 as a targeted therapy for CML," Cancer Investigation 21(3):429-438, Jan. 1, 2003.
Okeyo-Owuor et al., "U2AF1 mutations alter sequence specificity of pre-mRNA binding and splicing," Leukemia 29(4):909-917, Apr. 2015.
Pankevich et al., "Improving and Accelerating Drug Development for Nervous System Disorders," Neuron 84(3):546-553, Nov. 5, 2014.
Park et al., "Hematopoietic Stem Cells Are the Disease-Initiating Cells in the Myelodysplastic Syndromes," Blood 118(21):789, Nov. 18, 2011.
Pellagatti et al., "Deregulated gene expression pathways in myelodysplastic syndrome hematopoietic stem cells," Leukemia 24(4):756-764, Apr. 2010.
Pellagattti et al., "Gene expression profiles of CD34+ cells in myelodysplastic syndromes: involvement of interferon-stimulated genes and correlation to FAB subtype and karyotype," Blood 108(1):337-345, Jul. 1, 2006.
Polley et al., "Statistical and Practical Considerations for Clinical Evaluation of Predictive Biomarkers," Journal of the National Cancer Institute 105(22):1677-1683, Nov. 20, 2013.
Pourbasheer et al., "Quantitative structure-activity relationship (QSAR) study of interleukin-1 receptor associated kinase 4 (IRAK-4) inhibitor activity by the genetic algorithm and multiple linear regression (GA-MLR) method," Journal of Enzyme Inhibition and Medicinal Chemistry 25(6)844-853, Apr. 30, 2010.
Powers et al., "Discovery and initial SAR of inhibitors of interleukin-1 receptor-associated kinase-4," Bioorganic and Medicinal Chemistry Letters 16(11):2842-2845, Jun. 1, 2006.
Privette Vinnedge et al., "The DEK Oncogene Is a Target of Steroid Hormone Receptor Signaling in Breast Cancer," PloS One 7(10):e46985, Oct. 10, 2012.
Privette Vinnedge et al., "The DEK oncogene promotes cellular proliferation through paracrine Wnt signaling in Ron receptor-positive breast cancers," Oncogene 34(18):2325-2336, Apr. 2015.
Privette Vinnedge et al., "The human DEK oncogene stimulates b-catenin signaling, invasion and mammosphere formation in breast cancer," Oncogene 30(24):2741-2752, Jun. 2011.
Rhyasen et al., "IRAK signalling in cancer," British Journal of Cancer 112(2):232-237, Jan. 2015.
Rhyasen et al., "Targeting IRAK1 as a Therapeutic Approach for Myelodysplastic Syndrome," Cancer Cell 24(1):90-104, Jul. 8, 2013.
Sammons et al., "Negative Regulation of the RelA/p65 Transactivation Function by the Product of the DEK Proto-oncogene," Journal of Biological Chemistry 281(37):26802-26812, Sep. 15, 2006.
Sandén et al., "The DEK oncoprotein binds to highly and ubiquitously expressed genes with a dual role in their transcriptional regulation," Molecular Cancer 13(1):215, Dec. 2014.
Sawatsubashi, S., et al., "A histone chaperone, DEK, transcriptionally coactivates a nuclear receptor," Genes and Development 24(2):159-170, Jan. 15, 2010.
Seganish, "Inhibitors of interleukin-1 receptor-associated kinase 4 (IRAK4): a patent review (2012-2015)," Expert Opinion on Therapeutic Patents 26(8):917-32, Aug. 2, 2016.
Sekeres, "Are we nearer to curing patients with MDS?," Best Practice & Research Clinical Haematology 23(4):481-487, Dec. 1, 2010.
Sekeres, "The epidemiology of myelodysplastic syndromes," Hematology/Oncology Clinics of North America 24(2):287-294, Apr. 1, 2010.
Shibata et al., "DEK oncoprotein regulates transcriptional modifiers and sustains tumor initiation activity in high-grade neuroendocrine carcinoma of the lung," Oncogene 29(33):4671-4681, Aug. 19, 2010.
Shirai et al., "Mutant U2AF1 expression alters hematopoiesis and Pre-mRNA splicing in transgenic mice," Blood 124(21):827, Dec. 6, 2014.
Sokol et al., "Identification of a risk dependent microRNA expression signature in myelodysplastic syndromes," British Journal of Haematology, 153(1):24-32, Apr. 2011.
Srivastava et al., "Augmentation of therapeutic responses in melanoma by inhibition of IRAK-1,-4," Cancer Research 72(23):6209-6216, Dec. 2012.
Starczynowski et al., "Genome-wide identification of human microRNAs located in leukemia-associated genomic alterations," Blood 117(5):595-607, Jan. 13, 2011.
Starczynowski et al., "Identification of miR-145 and miR-146a as mediators of the 5q-syndrome phenotype," Nature Medicine 16(1):49-58, Jan. 2010.

(56) References Cited

OTHER PUBLICATIONS

Starczynowski et al., "Innate immune signaling in the myelodysplastic syndromes," Hematology/Oncology Clinics 24(2):343-359, Apr. 1, 2010.
Starczynowski et al., "MicroRNA-I 46a disrupts hematopoietic differentiation and survival," Experimental Hematology 39(2):167-178, Feb. 1, 2011.
Starczynowski et al., "TRAF6 is an amplified oncogene bridging the RAS and NF-kappaB pathways in human lung cancer," Journal of Clinical Investigation 121(10):4095-4105, Oct. 3, 2011.
Subramanian et al., "Gene set enrichment analysis: a knowledge-bases approach for interpreting genome-wide expression profiles," Proceedings of the National Academy of Sciences 102(43):15545-15550, Oct. 25, 2005.
Taganov et al., "NF-kappaB-dependent induction of microRNA miR-146, an inhibitor targeted to signaling proteins of innate immune responses," Proceedings of the National Academy of Sciences 103(33):12481-12486, Aug. 15, 2006.
Tehranchi et al., "Persistent malignant stem cells in del(5q) myelodysplasia in remission," New England Journal of Medicine 363(11):1025-1037, Sep. 9, 2010.
The National Formulary, 14th Ed. American Pharmaceutical Association. Washington, D.C. pp. 1-5. Jul. 1, 1975.
The National Formulary, 14th Ed. American Pharmaceutical Association. Washington, D.C. pp. 6-19. Jul. 1, 1975.
Thomadaki et al., "Molecular profile of the BCL2 family of the apoptosis related genes in breast cancer cells after treatment with cytotoxic/cytostatic drugs," Connect Tissue Research 49(3-4):261-264, Jan. 1, 2008.
Tohyama et al., "A noval factor-dependent human myelodysplastic cell line, MDS92, contains haemopoietic cells of several lineages," British Journal of Haematology 91(4):795-799, Dec. 1995.
Tse et al., "ABT-263: a potent and orally bioavailable Bcl-2 family inhibitor," Cancer Research 68(9):3421-3428, May 1, 2008.
U.S. Appl. No. 62/248,050, filed Oct. 29, 2015.
Valk et al., "Prognostically useful gene-expression profiles in acute myeloid leukemia," New England Journal of Medicine 350(16):1617-1628, Apr. 15, 2004.
Vanderwerf et al., "TLR8-dependent TNF-(alpha) overexpression in Fanconi anemia group C cells," Blood 114(26):5290-5298, Dec. 17, 2009.
Hou et al., "Splicing factor mutations predict poor prognosis in patients with de novo acute myeloid leukemia," Oncotarget 7(8):9084-9101, Feb. 23, 2016.
Ohgmai et al., "Next-generation sequencing of acute myeloid leukemia identifies the significance of TP53, U2AF1, ASXL1, and TET2 mutations," Modern Pathology 28(5):706-714, Nov. 21, 2014.
Smith et al., "U2AF1 mutations induce oncogenic IRAK4 isoforms and activate innate immune pathways in myeloid malignancies," Nature Cellular Biology 21(5): 640-650, Apr. 22, 2019.
Vasikova et al., "A distinct expression of various gene subsets in CD34+ cells from patients with early and advanced myelodysplastic syndrome," Leukemia Research 34(12):1566-1572, Dec. 1, 2010.
Wang et al., "IRAK-4 Inhibitors for Inflammation," Current Topics in Medicinal Chemistry 9(8):727-734, May 1, 2009.
Wei et al., "Deregulation of TLR2-JMJD3 Innate Immunity Signaling, Including a Rare TLR2 SNP As a Potential Somatic Mutation, in Myelodysplastic Syndromes (MDS)," Blood 120(21):1700, Nov. 16, 2012.
Wise-Draper et al., "Apoptosis Inhibition by the Human DEK Oncoprotein Involves Interference with p53 Functions," Molecular and Cellular Biology 26(20):7506-7519, Oct. 2006.
Wunderlich et al., "AML xenograft efficiency is significantly improved in NOD/SCID-IL2RG mice constitutively expressing human SCF, GM-CSF and IL-3," Leukemia 24(10):1785-1788, Oct. 24, 2010.
Xie et al., "Systematic discovery of regulatory motifs in human promoters and 3' UTRs by comparison of several mammals," Nature 434(7031):338-345, Mar. 2005.

Yang et al., "Interleukin-1 receptor associated kinases-1/4 inhibition protects against acute hypoxia/ischemia-induced neuronal injury in vivo and in vitro," Neuroscience 196:25-34, Nov. 24, 2011.
Zhao et al., "NF-kappaB dysregulation in micro-RNA-146a-deficint mice drives the development of myeloid malignancies," Proceedings of the National Academy of Sciences 108(22):9184-9189, May 31, 2011.
Adams et al., "DEK promotes HPV-positive and -negative head and neck cancer cell proliferation," Oncogene34(7):868-877, Feb. 2015.
Adams et al., "Identifying DEK-dependent transcriptional signatures in HPV+ and HPV− head and neck squamous cell carcinoma (HNSCC)," NCBI, https://www.ncbi.nlm.nih.gov/geo/query/acc.cgi?acc=GSE70462, Feb. 5, 2016 [retreived Apr. 9, 2019], 2 pages.
Adams et al., "IRAK1 is a novel DEK transcriptional target and is essential for head and neck cancer cell survival," Oncotarget 6(41):43395-43407, Dec. 22, 2015.
Alexiadis et al., "The protein encoded by the proto-oncogene DEK changes the topology of chromatin and reduces the efficiency of DNA replication in a chromatin-specific manner," Genes and Development 14(11):1308-1312, Jun. 1, 2000.
Anastassiadis et al., "Comprehensive assay of kinase catalytic activity reveals features of kinase inhibitor selectivity," Nature Biotechnology 29(11):1039-1045, Nov. 2011.
Ang et al., "Human Papillomavirus and Survival of Patients with Oropharyngeal Cancer," New England Journal of Medicine 363(1):24-35, Jul. 2010.
Bar et al., "Gene Expression Patterns in Myelodyplasia Underline the Role of Apoptosis and Differentiation in Disease Initiation and Progression," Translational Oncogenomics 3:137-149, May 29, 2008.
Barreyro et al., "Overexpression of IL-1 receptor accessory protein in stem and progenitor cells and outcome correlation in AML and MDS," Blood 120(6):1290-8, Aug. 9, 2012.
Boldin et al., "miR-146a Is a significant brake on autoimmunity, myeloproliferation and cancer in mice," Journal of Experimental Medicine 208(6):1189-201, Jun. 6, 2011.
Breccia et al., "NF-kappaB as a potential therapeutic target in myelodysplastic syndromes and acute myeloid leukemia", Expert Opinion on Therapeutic Targets, 14(11):1157-1176, Nov. 1, 2010.
Buckley et al., "IRAK-4 inhibitors. Part I: A series of amides," Bioorganic and Medicinal Chemistry Letters 18(11):3211-3214, Jun. 1, 2008.
Buckley et al., "IRAK-4 inhibitors. Part II: A structure-based assessment of imidazo [1,2-a] pyridine binding," Bioorganic and Medicinal Chemistry Letters 18(11):3291-3295, Jun. 1, 2008.
Buckley et al., "IRAK-4 inhibitors. Part III: A series of imidazo [1,2-a] pyridines," Bioorganic and Medicinal Chemistry Letters 18(12):3656-3660, Jun. 15, 2008.
Camos et al., "Gene expression profiling of acute myeloid leukemia with translocation t(8; I 6)(p 11;p13) and MYST3-CREBBP rearrangement reveals a distinctive signature with a specific pattern of HOX gene expression," Cancer Research 66(14):6947-6954, Jul. 15, 2006.
Campillos et al., "Transcriptional activation by AP-2a is modulated by the oncogene DEK," Nucleic Acids Research 31(5):1571-1575, Mar. 1, 2003.
Cerami et al., "The eBio Cancer Genomics Portal: An Open Platform for Exploring Multidimensional Cancer Genomics Data," Cancer Discovery 2(5):401-404, May 2012.
Chaturvedi et al., "Human Papillomavirus and Rising Oropharyngeal Cancer Incidence in the United States," Journal of Clinical Oncology 29(32):4294-4301, Nov. 10, 2011.
Chaudhary et al., "Recent advances in the discovery of small molecule inhibitors of interleukin-1 receptor-associated kinase 4 (IRAK4) as a therapeutic target for inflammation and oncology disorders: Miniperspective," Journal of Medicinal Chemistry 58(1):96-110, Dec. 5, 2014.
Chen et al., "Distinctive gene expression profiles of CD34 cells from patients with myelodysplastic syndrome characterized by specific chromosomal abnormalities," Blood 104(13):4210-4218, Dec. 15, 2004.

(56) References Cited

OTHER PUBLICATIONS

Chen et al., "ToppGene Suite for gene list enrichment analysis and candidate gene prioritization," Nucleic Acids Research 37(suppl_2):W305-W311, May 22, 2009.
Conze et al., "Lys63-Linked Polyubiquitination of IRAK-1 Is Required for Interleukin-1 Receptor- and Toll-Like Receptor-Mediated NF-kappaB Activation", Molecular and Cellular Biology 28(10):3538-3547, May 15, 2008.
Corey et al., "Myelodysplastic syndromes: the complexity of stem-cell diseases," Nature Reviews Cancer 7(2):118-129, Feb. 2007.
Database PubChem Compound [Online], NCBI; Mar. 21, 2014 (Mar. 21, 2014), Database accession No. CID 73265219.
Database PubChem Compound [Online], NCBI; Mar. 21, 2014 (Mar. 21, 2014), Database accession No. CID 73265220.
Datta et al., "Oncoprotein DEK as a tissue and urinary biomarker for bladder cancer," BMC Cancer 11(1):234, Dec. 2011.
Ebert, "Preface: The biology and Treatment of Myelodysplastic Syndrome," Hematology/Oncology Clinics of North America 24(2):xiii-xvi, Apr. 1, 2010.
Edgar et al., "Gene Expression Omnibus: NCBI gene expression and hybridization array data repository," Nucleic Acids Research 30(1):207-210, Jan. 1, 2002.
Fang et al., "Cytotoxic effects of bortezomib in myelodysplastic syndrome/acute myeloid leukemia depend on autophagy-mediated lysosomal degradation of TRAF6 and repression of PSMA1," Blood 120(4):858-867, Jul. 26, 2012.
Flannery et al., "The interleukin-1 receptor-associated kinases: critical regulators of innate immune signaling," Biochemical Pharmacology 80(12):1981-1991, Dec. 15, 2011.
Flicek et al., "Ensembl 2012," Nucleic Acids Research 40(Database issue):D84-90, Nov. 15, 2011.
Gao et al., "Integrative Analysis of Complex Cancer Genomics and Clinical Profiles Using the cBioPortal," Science Signaling 6(269):1-19, Apr. 2, 2013.
Gondek et al., "Chromosomal lesions and uniparental disomy detected by SMP arrays in MDS, MDS/MPD, and MDS-derived AML," Blood 111(3):1534-1542, Feb. 1, 2008.
Graubert et al., "Recurrent mutations in the U2AF1 splicing factor in myelodysplastic syndromes," Nature Genetics 44(1):53-57, Jan. 2012.
Greenberg et al., "International scoring system for evaluating prognosis in myelodyplastic syndromes," Blood 89(6):2079-2088, Mar. 15, 1997.
Greenberg, "Current therapeutic approaches for patients with myelodysplastic syndromes," British Journal of Haematology 150(2):131-143, Jul. 2010.
Griner et al., "High-throughput combinatorial screening identifies drugs that cooperate with ibrutinib to kill activated B-cell-like diffuse large B-cell lymphoma cells," Proceedings of the National Academy of Sciences 111(6): 2349-2354, Feb. 11, 2014.
Hofmann et al., "Characteriszation of gene expression of CD34+ cells from normal and myelodyplastic bone marrow," Blood 100(10):3553-3560, Nov. 15, 2002.
Hung et al., "miR-146a Enhances the Oncogenicity of Oral Carcinoma by Concomitant Targeting of the IRAKI, TRAF6 and NUMB Genes," PloS One 8(11):e79926, Nov. 26, 2013.
Hynes et al., "Chapter Nine—Advances in the Discovery of Small-Molecule IRAK4 Inhibitors," Annual Reports in Medicinal Chemistry 49:117-133, Oct. 2014.
International Search Report and Written Opinion dated Feb. 16, 2018, Patent Application No. PCT/US2017/047088, filed Aug. 16, 2017, 14 pages.
International Search Report and Written Opinion dated Jan. 19, 2017, Patent Application No. PCT/US2016/058864, filed Oct. 26, 2016, 11 pages.
International Search Report and Written Opinion dated Jan. 25, 2018, International Patent Application No. PCT/US2017/059091, filed Oct. 30, 2017, 13 pages.
International Search Report and Written Opinion dated Nov. 20, 2014, Patent Application No. PCT/US2014/039156, filed May 22, 2014, 11 pages.
Kavanaugh et al., "The human DEK oncogene regulates DNA damage response signaling and repair," Nucleic Acids Research 39(17):7465-7476, Jun. 7, 2011.
Khodadoust et al., "Melanoma Proliferation and Chemoresistance Controlled by the DEK Oncogene," Cancer Research 69(16):6405-6413, Aug. 15, 2009.
Ko et al., "Regulation of histone acetyltransferase activity of p300 and PCAF by proto-oncogene protein DEK," FEBS Letters 580(13):3217-3222, May 29, 2006.
Koch et al., "MyD88-Dependent Signaling Decreases the Antitumor Efficacy of Epidermal Growth Factor Receptor Inhibition in Head and Neck Cancer Cells," Cancer Research 75(8):1657-1667, Apr. 15, 2015.
Koleva et al., "C/EBPa and DEK coordinately regulate myeloid differentiation," Blood 119(21):4878-4888, May 24, 2012.
Kollewe et al., "Sequential autophosphorylation steps in the interleukin-I receptor-associated kinase-1 regulate its availability as an adapter in interleukin-1 signaling," Journal of Biological Chemistry 279(7):5227-5236, Feb. 13, 2004.
Komurov et al., "NetWalker: a contextual network analysis tool for functional genomics," BMC Genomics 13(1):282, Dec. 2012.
Extended European Search Report dated Apr. 6, 2021 for European Patent Application No. 20211957, 12 pages.

A     CTG

AC220 (nM)

B     Caspase

AC220 (nM)

A

D

F

G

A

B

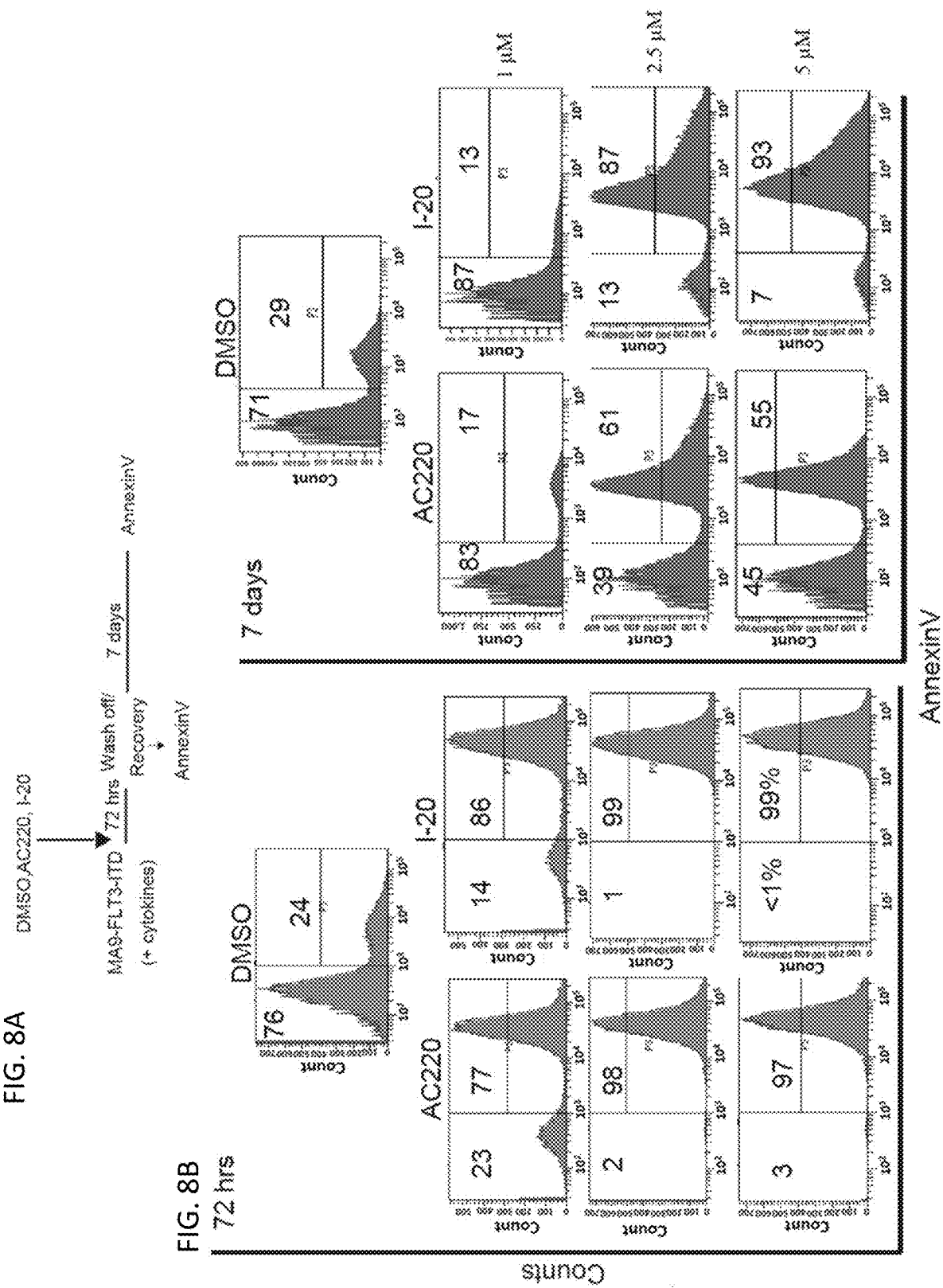

C

D

A

B

C

SUBSTITUTED IMIDAZO[1,2-A]PYRIDINES AS IRAK 1/4 AND FLT3 INHIBITORS

CROSS-REFERENCE TO RELATED APPLICATIONS

The present application is a U.S. National Stage entry under 35 U.S.C. § 371 of International Application No. PCT/US2017/047088, filed on Aug. 16, 2017, designating the United States of America and published in English on Mar. 1, 2018, which in turn claims priority to U.S. Provisional Application No. 62/375,965, filed on Aug. 17, 2016, each of which is hereby incorporated by reference in its entirety.

GOVERNMENT RIGHTS

This invention was made with government support under HL111103 awarded by the National Institutes of Health, and in the performance of a Cooperative Research and Development Agreement with the National Institutes of Health, an Agency of the Department of Health and Human Services. The Government of the United States has certain rights in this invention.

BACKGROUND

Several compounds are known to treat cancer, but do so inadequately. Some known compounds, such as Quizartinib and Cremolanib, can be used to treat Acute Myeloid Leukemia (AML). Some of these treatments do not result in complete remission or partial remission. In some instances, treatment can result in mutations that are resistant to inhibitors. Several compounds are known to treat blood disorders (e.g., Myelodysplastic syndromes (MDS)), but do so inadequately. Certain embodiments of the invention can address one or more of these deficiencies.

Some embodiments of the invention include inventive compounds (e.g., compounds of Formula (I)). Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer or blood disorders). Further embodiments include methods for making the inventive compounds. Additional embodiments of the invention are also discussed herein.

SUMMARY

Some embodiments of the present invention include a compound selected from Formula (I)

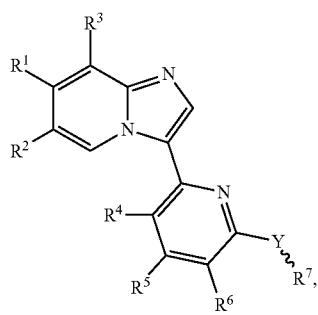

(I)

salts, optical isomers, geometric isomers, salts of isomers, and derivatives thereof. In some embodiments, $R^1$ is H, halogen, hydroxy, $C_1$-$C_7$ alkyl, $C_2$-$C_7$ alkenyl, $C_2$-$C_7$ alkynyl, or $C_1$-$C_6$ alkoxy, which $C_1$-$C_7$ alkyl, $C_2$-$C_7$ alkenyl, $C_2$-$C_7$ alkynyl, or $C_1$-$C_6$ alkoxy is optionally substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, ethyl, or morpholinyl; $R^2$ is H, halogen, hydroxy, —CN, methanoyl (—COH), carboxy (—CO$_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl, which methanoyl (—COH), carboxy (—CO$_2$H), $C_1$-$C_7$ alkyl, $C_2$-$C_7$ alkenyl, $C_2$-$C_7$ alkynyl, $C_2$-$C_6$ alkoxy, cycloalkyl, heterocyclyl, aryl, or heteroaryl is optionally substituted with one or more of halogen, hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, $C_1$-$C_3$ alkyl, $C_1$-$C_3$ perfluorinated alkyl, or $C_1$-$C_3$ alkoxy; $R^3$ is H, halogen, hydroxy, $C_1$-$C_3$ alkyl, $C_2$-$C_3$ alkenyl, $C_2$-$C_3$ alkynyl, or $C_1$-$C_2$ alkoxy, which $C_1$-$C_3$ alkyl, $C_2$-$C_3$ alkenyl, $C_2$-$C_3$ alkynyl, or $C_1$-$C_2$ alkoxy is optionally substituted with one or more of halogen, hydroxy, methanoyl (—COH), carboxy (—CO$_2$H), cyano (—CN), ethynyl (—CCH), sulfo (—SO$_3$H), methyl, or ethyl; $R^4$ is H, halogen, hydroxy, methanoyl (—COH), carboxy (—CO$_2$H), nitro (—NO$_2$), cyano (—CN), sulfo (—SO$_3$H), $C_1$-$C_4$ alkyl, $C_2$-$C_4$ alkenyl, $C_2$-$C_4$ alkynyl, or $C_1$-$C_3$ alkoxy, which $C_1$-$C_4$ alkyl, $C_2$-$C_4$ alkenyl, $C_2$-$C_4$ alkynyl, or $C_1$-$C_3$ alkoxy is optionally substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, or ethyl; $R^5$ is H, halogen, hydroxy, methanoyl (—COH), carboxy (—CO$_2$H), nitro (—NO$_2$), cyano (—CN), sulfo (—SO$_3$H), $C_1$-$C_4$ alkyl, $C_2$-$C_4$ alkenyl, $C_2$-$C_4$ alkynyl, or $C_1$-$C_3$ alkoxy, which $C_1$-$C_4$ alkyl, $C_2$-$C_4$ alkenyl, $C_2$-$C_4$ alkynyl, or $C_1$-$C_3$ alkoxy is optionally substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, or ethyl; $R^6$ is H, halogen, hydroxy, methanoyl (—COH), carboxy (—CO$_2$H), nitro (—NO$_2$), cyano (—CN), sulfo (—SO$_3$H), $C_1$-$C_4$ alkyl, $C_2$-$C_4$ alkenyl, $C_2$-$C_4$ alkynyl, or $C_1$-$C_3$ alkoxy, which $C_1$-$C_4$ alkyl, $C_2$-$C_4$ alkenyl, $C_2$-$C_4$ alkynyl, or $C_1$-$C_3$ alkoxy is optionally substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, or ethyl; Y is

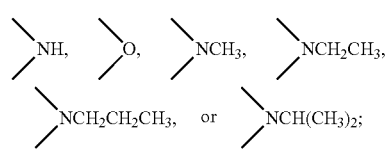

$R^7$ is

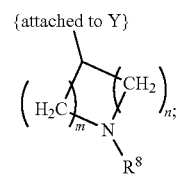

$R^8$; $R^8$ is H, $C_1$-$C_4$ alkyl, $C_2$-$C_4$ alkenyl, $C_2$-$C_4$ alkynyl, methanoyl (—COH), ethanoyl (—COCH$_3$), benzoyl (—COC$_6$H$_5$), toluoyl, carboxy (—CO$_2$H), nitro (—NO$_2$), cyano (—CN), or —COCH$_2$CN; n is 0, 1, 2, 3, 4, or 5; m is 0, 1, 2, 3, 4, or 5; and n+m is at least 1. In some embodiments, $R^1$ is H, halogen, hydroxy, $C_1$-$C_7$ alkyl, or $C_1$-$C_6$ alkoxy, which $C_1$-$C_7$ alkyl or $C_1$-$C_6$ alkoxy is optionally substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, or ethyl, or morpholinyl. In other embodiments, $R^1$ is Cl, methyl, 2-(morpholinyl)ethoxy, or —OCH$_3$. In yet other embodiments, $R^1$ is not H. In some embodiments, $R^2$ is H, halogen, hydroxy, —CN, methanoyl (—COH), carboxy (—CO$_2$H), $C_1$-$C_7$ alkyl, $C_1$-$C_6$ alkoxy, cycloalkyl, heterocyclyl, aryl, or heteroaryl, which methanoyl (—COH), carboxy (—CO$_2$H), $C_1$-$C_7$ alkyl, $C_2$-$C_6$ alkoxy, cycloalkyl, heterocyclyl, aryl, or heteroaryl is optionally substituted with one or more of halogen, hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, $C_1$-$C_3$ alkyl, $C_1$-$C_3$ perfluoronated alkyl, or $C_1$-$C_3$ alkoxy. In certain embodiments, $R^2$ is —CO-morpholin-4-yl, —CON(CH$_3$)$_2$, Cl, methyl, —CN, ethynyl, —CONH$_2$, —CON(CH$_3$)$_2$, 2-(morpholinyl)ethoxy, ethoxy, methoxy, 1H-pyrazol-4-yl, 1-methyl-pyrazol-4-yl, 1-(morpholin-4-yl)-pyrazol-4-yl, pyridin-3-yl, 2-methoxy-pyridin-5-yl, pyridin-4-yl, 3,5-dimethylisoxazol-4-yl, 1H-pyrrol-3-yl, 3,5-(di-methyl)-pyrazolyl, pyrazol-3-yl, 5-tetrazolyl, 1H-pyrazol-4-yl, 4-ethyl-piperazin-1-yl, perfluorinated methyl, or perfluorinated ethyl. In still other embodiments, $R^2$ is not H. In certain embodiments, $R^3$ is H, halogen, hydroxy, $C_1$-$C_3$ alkyl, or $C_1$-$C_2$ alkoxy, which $C_1$-$C_3$ alkyl or $C_1$-$C_2$ alkoxy can optionally be substituted with one or more of halogen, hydroxy, methanoyl (—COH), carboxy (—CO$_2$H), cyano (—CN), ethynyl (—CCH), sulfo (—SO$_3$H), methyl, or ethyl. In other embodiments, $R^3$ is H, methoxy, which methoxy is optional substituted with one, two, or three halogen. In still other embodiments, $R^3$ is H or methoxy. In some embodiments, $R^4$ is H, halogen, hydroxy, methanoyl (—COH), carboxy (—CO$_2$H), nitro (—NO$_2$), cyano (—CN), sulfo (—SO$_3$H), $C_1$-$C_4$ alkyl, or $C_1$-$C_3$ alkoxy, which $C_1$-$C_4$ alkyl or $C_1$-$C_3$ alkoxy is optionally substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, or ethyl. In other embodiments, $R^4$ is F, Cl, Br, methyl, perfluorinated methyl, or methoxy. In some embodiments, $R^5$ is H, halogen, hydroxy, methanoyl (—COH), carboxy (—CO$_2$H), nitro (—NO$_2$), cyano (—CN), sulfo (—SO$_3$H), $C_1$-$C_4$ alkyl, or $C_1$-$C_3$ alkoxy, which $C_1$-$C_4$ alkyl or $C_1$-$C_3$ alkoxy is optionally substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, or ethyl. In other embodiments, $R^5$ is F, Cl, Br, methyl, ethyl, or methoxy. In some embodiments, $R^6$ is H, halogen, hydroxy, methanoyl (—COH), carboxy (—CO$_2$H), nitro (—NO$_2$), cyano (—CN), sulfo (—SO$_3$H), $C_1$-$C_4$ alkyl, or $C_1$-$C_3$ alkoxy, which $C_1$-$C_4$ alkyl or $C_1$-$C_3$ alkoxy can optionally be substituted with one or more of halogen, hydroxy, methanoyl (—COH), carboxy (—CO$_2$H), nitro (—NO$_2$), cyano (—CN), ethynyl (—CCH), sulfo (—SO$_3$H), methyl, or ethyl. In other embodiments, $R^6$ is F, Cl, Br, methyl, perfluorinated methyl, or methoxy. In some embodiments, Y is

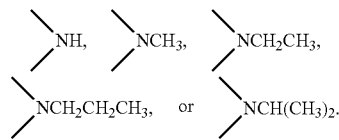

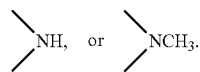

In other embodiments, Y is

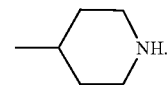

In some embodiments, $R^7$ is piperid-2-yl, piperid-3-yl, piperid-4-yl, pyrrolidin-2-yl, pyrrolidin-3-yl, or azetidyl. In certain embodiments, $R^8$ is H, ethanoyl (—COCH$_3$), benzoyl (—COC$_6$H$_5$), ethynyl (—CCH), or —COCH$_2$CN. In some instances, n is 1, 2, or 3. In other instances, m is 1, 2, or 3.

In some embodiments, the compound is I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, or I-68. In other embodiments, the compound is I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, or I-68. In yet other embodiments, the compound is I-2, I-15, I-20, I-22, I-24, I-26, I-27, I-42, I-53, or I-54. In still other embodiments, the compound is I-2, I-15, I-20, I-22, I-24, I-26, I-27, I-42, I-43, I-44, I-53, or I-54. In some instances, the compound is I-20, I-22, I-24, I-26, I-27, I-42, I-53, or I-54. In yet other instances, the compound is I-20, I-22, I-24, I-26, I-27, I-42, I-43, I-44, I-53, or I-54.

In some embodiments, if Y is —NH—; $R^1$ is H; $R^3$ is H; $R^4$ is H; $R^5$ is H; $R^6$ is H; and $R^8$ is H, then (a) $R^2$ is not H, Cl, methoxy, or CN, and (b) $R^7$ is not

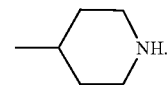

In other embodiments, if Y is —NH—; $R^1$ is H; $R^3$ is H; $R^4$ is H; $R^5$ is H; $R^6$ is H; and $R^8$ is H, then (a) $R^2$ is not H, Cl, F, Br, I, methoxy, ethoxy, or CN, and (b) $R^7$ is not

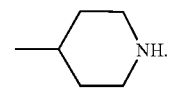

In still other embodiments, if Y is —NH—; $R^1$ is H; $R^3$ is H; $R^4$ is H; $R^5$ is H; $R^6$ is H; and $R^8$ is H, then (a) $R^2$ can be hydroxy, methanoyl (—COH), carboxy (—CO$_2$H), $C_1$-$C_7$ alkyl, $C_2$-$C_7$ alkenyl, $C_2$-$C_7$ alkynyl, $C_3$-$C_6$ alkoxy, cycloalkyl, heterocyclyl, aryl, or heteroaryl, which methanoyl (—COH), carboxy (—CO$_2$H), $C_1$-$C_7$ alkyl, $C_2$-$C_7$ alkenyl, $C_2$-$C_7$ alkynyl, $C_3$-$C_6$ alkoxy, cycloalkyl, heterocyclyl, aryl, or heteroaryl can optionally be substituted with one or more of halogen, hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, C$_1$-C$_3$ alkyl, C$_1$-C$_3$ perfluoronated alkyl, or C$_1$-C$_3$ alkoxy, and (b) R$^7$ is not

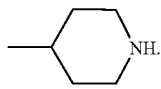

In yet other embodiments, if Y is —NH—; R$^1$ is H; R$^3$ is H; R$^4$ is H; R$^5$ is H; R$^6$ is H; and R$^8$ is H, then (a) R$^2$ can be hydroxy, methanoyl (—COH), carboxy (—CO$_2$H), C$_1$-C$_7$ alkyl, C$_2$-C$_7$ alkenyl, C$_2$-C$_7$ alkynyl, C$_5$-C$_6$ alkoxy, cycloalkyl, heterocyclyl, aryl, or heteroaryl, which methanoyl (—COH), carboxy (—CO$_2$H), C$_1$-C$_7$ alkyl, C$_2$-C$_7$ alkenyl, C$_2$-C$_7$ alkynyl, C$_5$-C$_6$ alkoxy, cycloalkyl, heterocyclyl, aryl, or heteroaryl can optionally be substituted with one or more of halogen, hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, C$_1$-C$_3$ alkyl, C$_1$-C$_3$ perfluoronated alkyl, or C$_1$-C$_3$ alkoxy, and (b) R$^7$ is not

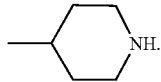

In certain embodiments, one or more of compounds I-1, I-2, I-3, I-4, I-5, I-6, I-7, I-8, I-9, I-10, I-11, I-12, I-13, I-14, I-15, I-16, I-17, I-18, or I-19 are not included in Formula (I). In still other embodiments, compounds I-1, I-2, I-3, I-4, I-5, I-6, I-7, I-8, I-9, I-10, I-11, I-12, I-13, I-14, I-15, I-16, I-17, I-18, and I-19 are not included in Formula (I).

Some embodiments of the invention include a composition comprising a compound, as disclosed herein (e.g., Formula (I)). In certain embodiments, the amount of the compound is from about 0.0001% (by weight total composition) to about 99%. In other embodiments, the composition further comprises a formulary ingredient, an adjuvant, or a carrier.

Some embodiments of the invention include a pharmaceutical composition comprising a compound, as disclosed herein (e.g., Formula (I)). In certain embodiments, the amount of the compound is from about 0.0001% (by weight total composition) to about 50%. In other embodiments, the pharmaceutical composition further comprises a formulary ingredient, an adjuvant, or a carrier.

Some embodiments of the invention include a method for providing an animal with a compound comprising one or more administrations of one or more compositions comprising a compound as disclosed here (e.g., Formula (I)), where the compositions may be the same or different if there is more than one administration. In other embodiments, at least one of the one or more compositions further comprises a formulary ingredient. In certain embodiments, at least one of the one or more compositions comprises any composition disclosed herein or any pharmaceutical composition disclosed herein. In still other embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In some embodiments, if there is more than one administration at least one composition used for at least one administration is different from the composition of at least one other administration. In other embodiments, the compound of at least one of the one or more compositions is administered to the animal in an amount of from about 0.01 mg/kg animal body weight to about 15 mg/kg animal body weight. In certain embodiments, the animal is a human, a rodent, or a primate.

Some embodiments, of the invention include a method for treating an animal for a disease, comprising one or more administrations of one or more compositions comprising any compound disclosed herein (e.g., Formula (I)), wherein the compositions may be the same or different if there is more than one administration. In some instances, at least one of the one or more compositions further comprises a formulary ingredient. In other embodiments, at least one of the one or more compositions comprises any composition disclosed herein or any pharmaceutical composition disclosed herein. In certain embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In other embodiments, if there is more than one administration at least one composition used for at least one administration is different from the composition of at least one other administration. In still other embodiments, the compound of at least one of the one or more compositions is administered to the animal in an amount of from about 0.005 mg/kg animal body weight to about 50 mg/kg animal body weight. In yet other embodiments, the animal is a human, a rodent, or a primate. In certain embodiments, the animal is in need of the treatment. In some embodiments, the method is for treating a blood disorder, MDS, cancer, or AML. In other embodiments, the method is for treating acute myeloid leukemia, lymphoma, leukemia, bone marrow cancer, non-Hodgkin lymphoma, or Waldenstrom's macroglobulinemia. In yet other embodiments, the method is for treating MDS, MDS with a splicing factor mutation, MDS with a mutation in isocitrate dehydrogenase 1, or MDS with a mutation in isocitrate dehydrogenase 2. In certain embodiments, the animal is susceptible to ADL or MDS. In other embodiments, the method prevents or ameliorates future ADL or MDS. In some embodiments, the method occurs after one or more of having a blood disorder, having myelodysplastic syndrome, having myeloproliferative disease, an occurrence of chemical exposure, an exposure to ionizing radiation, or a treatment for cancer.

Some embodiments of the invention include a method for preparing any compound disclosed herein (e.g., Formula (I)) comprising, (a) reacting a compound of Formula (II) with a compound of Formula (III) to result in a mixture comprising a compound of Formula (IV);

(b) reacting a compound of Formula (IV) with a compound of Formula (V) to result in a mixture comprising a compound of Formula (VI);

(c) optionally reacting a compound of Formula (VI) with a compound of Formula (VII) to result in a mixture comprising a compound of Formula (VIII);

(d) removing one or more protecting groups from a compound of Formula (VI) or from a compound of Formula (VIII); and (e) recovering Formula (I),
where Formula (II) is

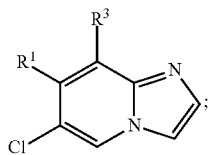

Formula (III) is

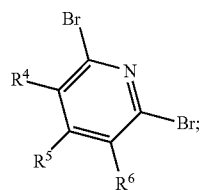

Formula (IV) is

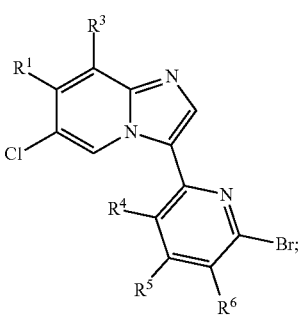

Formula (IV) is

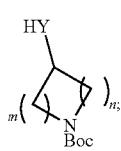

Formula (IV) is

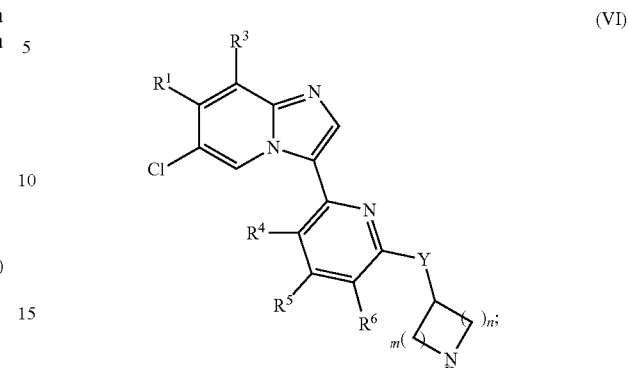

Formula (VII) is $R^2Bpin$ (VII); and
Formula (VIII) is

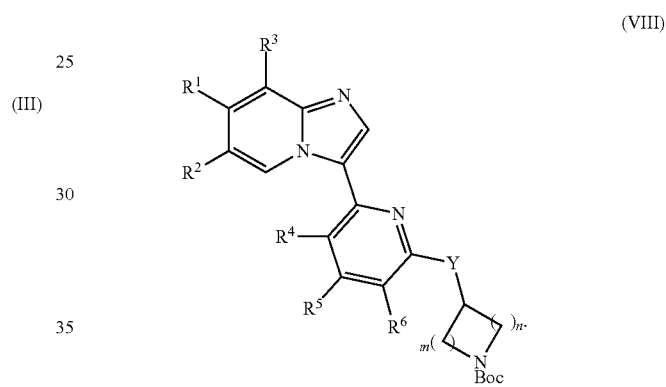

In some embodiments, $R^1$ is an $C_1$-$C_6$ alkoxy and the method further comprises (i) the step of reacting Formula (IV) to convert the $C_1$-$C_6$ alkoxy at $R^1$ to hydroxy and (ii) the step of reacting the product of (i) to convert the hydroxy at $R^1$ to a morpholino-$C_1$-$C_6$-alkoxy; and steps (i) and (ii) occur after step (a) and before step (b). In other embodiments, in step (b), Y is not O. In yet other embodiments, in step (b), Y is O. In some embodiments, during step (d), at least one of the one or more protecting groups removed is -Boc. In still other embodiments, $R^2$ is a halogen and the method further comprises the step of reacting Formula (I) to convert the halogen at $R^2$ to $C_2$-$C_7$ alkynyl, after step (d).

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 2A: Immunoblot analysis of MV4;

11 cells treated with AC220 (50 nM), compound I-20 (50 nM), or compound I-24 (50 nM) for 12 or 24 hours. FIG. 2B: Immunoblot analysis of MDSL cells treated with the indicated concentrations of I-24 or IRAK-Inh (Amgen) for 24 hours. FIG. 2C: Phospho (P)—STAT5 activity was measured by AlphaLISA assay in MV4; eleven cells treated with the indicated concentrations of I-15, I-20, I-43, or AC220 for 5 hours.

FIG. 3A: Immunoblot analysis of MA9-FLT3-ITD treated with AC220 (50 nM) for the indicated times. FIG. 3B: Immunoblot analysis of MV4; eleven cells treated with AC220 (1 or 50 nM) for the indicated times. FIG. 3C: Immunoblot analysis MA9-FLT3-ITD treated with AC220 (50 nM), AC220 (50 nM) and IRAK-Inh (10 μM), I-20 (50 nM), or IRAK-Inh alone (10 μM). FIG. 3D: Immunoblot analysis of human cord blood CD34+ cells transduced with MLL-AF9 and Nras (MA9-NRas) treated with AC220 (50 nM), AC220 (50 nM) and IRAK-Inh (10 μM), I-20 (50 nM), or IRAK-Inh alone (10 μM).

FIGS. 4A-4B: Heatmap response profile (left panel) and Delta Bliss analysis (right panel) for AC220 and IRAK-Inh (Amgen) combination treatment of MA9-FLT3-ITD cells. FIG. 4A: Cell-titer glow (CTG) percent response values represent normalized growth, relative to controls based on SybrGreen fluorescence intensities. FIG. 4B: Caspase activation values, relative to controls based on caspase-glo fluorescence intensities. FIG. 4C: The IC10 of AC220 was established in MA9-FLT3-ITD cells after 48 hour treatment using cell-titer glow relative response values normalized to growth compared to control cells (DMSO). FIG. 4D: MA9-FLT3-ITD cells were treated with IRAK-Inh (Amgen) alone or in combination with 0.3 nM of AC220 (IC10) for 72 hours. Cell-titer glow relative response values represent normalized growth compared to control cells (DMSO).

FIG. 5A: Generation of two independent clones (#3 and #6) derived from human cord blood CD34+ cells transduced with MLL-AF9 and then either FLT3-ITD (MA9-FLT3-ITD) or NRas (MA9-NRas). FIGS. 5B-G: MA9.3 or MA9.6 clones expressing FLT3-ITD or NRas were treated with the indicated compounds for 72 hours. Cell-titer glow relative response values represent normalized growth compared to control cells (DMSO) based on luminescence intensities. Cellular IC50 values (nM) are shown for each experiment.

FIGS. 7A-B: cells were treated with the indicated compounds for 72 hours. Cell-titer glow relative response values represent normalized growth compared to control cells (DMSO) based on luminescence intensities. Cellular IC50 values (nM) are shown for each experiment. FIG. 7C: Cell viability was determined in MA9-FLT3-ITD cells treated with 1 μM of the indicated compounds for 72 hours by flow cytometric analysis of AnnexinV. FIG. 7D: Leukemic colony formation of MA9-FLT3-ITD cells was determined in methylcellulose supplemented with 1 μM of the indicated compounds. Colony formation was determined after 10 days. FIG. 7E: Colony formation of normal cord blood CD34+ cells was determined in methylcellulose supplemented with 1 μM of the indicated compounds. Colony formation was determined after 10 days.

FIG. 8A: Overview of experimental design: MA9-FLT3-ITD cells were cultured in cytokines and then treated with AC220 or compound I-20 (1, 2.5, or 5 μM) for 72 hours. Cell viability was assessed by AnnexinV staining. Remaining cells were washed and replated in fresh media with cytokines. Recovery of MA9-FLT3-ITD cell growth was determined after 7 days by AnnexinV staining or Trypan Blue exclusion. FIG. 8B: Cell viability was determined in MA9-FLT3-ITD cells after 72 hours following treatment with the indicated compounds, or after 7 days of recovery. FIG. 8C: Overview of experimental design: MA9-FLT3-ITD cells were cultured in cytokines and then treated with AC220, compound I-20, or compound I-24 (5 μM) for 72 hours. Cell viability was assessed by AnnexinV staining. Remaining cells were washed and replated in fresh media with cytokines. Recovery of MA9-FLT3-ITD cell growth was monitored every 2 days by AnnexinV staining. FIG. 8D: Cell viability was determined in MA9-FLT3-ITD cells after 72 hours following treatment (Day 0) with the indicated compounds, or every 2 days post recovery by AnnexinV staining. Compound I-24 treated cells were not monitored past Day 2 as no viable cells remained. FIG. 8E: Overview of experimental design: MA9-FLT3-ITD cells were cultured in cytokines and then treated with AC220 or compound I-24 (5 μM) for 72 hours. Cell viability was assessed by AnnexinV staining. Remaining cells were washed and replated in fresh media with cytokines. After AC220-treated cells recovered (Day 7), they were subsequently treated with AC220 (5 μM) or I-24 (5 μM) ("i") and monitored every 2 days by AnnexinV staining. This step was repeated once more at Day 16 ("ii"). FIGS. 8F-G: Cell viability was determined in MA9-FLT3-ITD cells after 72 hours following treatment (Day 0) with the indicated compounds, or every 2 days post recovery by AnnexinV staining FIG. 8F: or Trypan Blue exclusion FIG. 8G.

FIG. 9A: Overview of in vivo experimental design: NRGS mice were injected i.v. with MA9-FLT3-ITD cells (2×105 cells/mouse). After 10 days, PBS or compound I-24 (30 mg/kg) was injected i.p. for 5 daily treatments, followed by a 2 day rest. After the 2nd treatment, one mouse from each group was sacrificed and MA9-FLT3-ITD (GFP+) cells were isolated from the BM by flow sorting for immunoblotting of FLT3 and IRAK4. A second cycle of daily injections of PBS or compound I-24 for 5 days, followed by daily monitoring of morbidity. FIG. 9B: Immunoblot analysis of sorted (GFP+) MA9-FLT3-ITD BM cells from xenografted mice after 2 doses of compound I-24. FIG. 9C: Overall survival of NRGS mice xenografted with MA9-FLT3-ITD treated with compound I-24 or PBS.

FIG. 10A: Colony formation of MDSL cells was determined in methylcellulose supplemented with 1 μM or 10 μM of the indicated compounds. Colony formation was determined after 10 days. FIG. 10B: MDSL cells were treated with the indicated compounds for 72 hours. Cell-titer glow relative response values represent normalized growth compared to control cells (DMSO) based on luminescence intensities.

DETAILED DESCRIPTION

Figure 1:
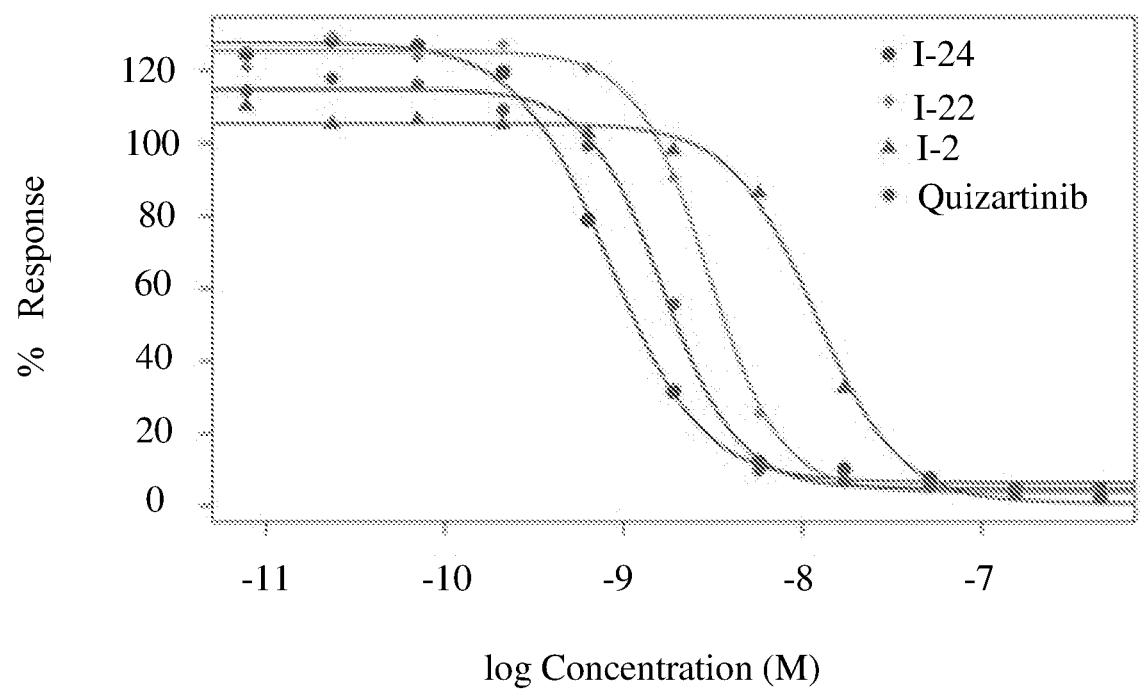
FIG. 1: Inhibitory activities of compounds I-2, I-22, I-24, and quizartinib were determined by measuring the $IC_{50}$ against human cord blood CD34+ cells transduced with MLL-AF9 and FLT3-ITD (designated as MA9-FLT3-ITD and also referred to as MLL-AF9/FLT3 ITD).

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive compounds (e.g., compounds of Formula (I)). Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound.

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, or 12 member aromatic hydrocarbon group which, when unsubstituted. Examples of aryl groups include, but are not limited to, phenyl, naphthyl, tolyl, and xylyl. For an aryl that is bicyclic, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds). For a monocyclic cycloalkyl, the ring is not aromatic. For a bicyclic cycloalkyl, if one ring is aromatic, then the other is not aromatic. For a bicyclic cycloalkyl, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl, tetrazolyl, 1H-pyrazol-4-yl, 1-Me-pyrazol-4-yl, pyridin-3-yl, pyridin-4-yl, 3,5-dimethylisoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl, one or both rings can be substituted.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, tetrahydropyran, pyrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), and morpholinyl (e.g., morpholin-1-yl, morpholin-2-yl, morpholin-3-yl, or morpholin-4-yl,). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl, one or both rings can be substituted.

As used herein (unless otherwise specified), the term "hetero atom" means an atom selected from nitrogen atom, oxygen atom, or sulfur atom.

As used herein (unless otherwise specified), the terms "hydroxy" or "hydroxyl" means a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

Some compounds of the invention can have one or more chiral centers and can exist in and be isolated in optically active and racemic forms, for any of the one or more chiral centers. Some compounds can exhibit polymorphism. The compounds of the present invention (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

Compounds and Compositions Including Pharmaceutical Compositions

Some embodiments of the invention include compounds of Formula (I):

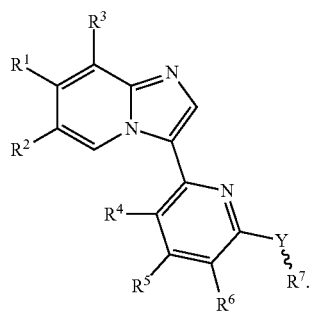

(I)

In other embodiments, $R^1$ can be a monovalent H, halogen (e.g., F, Cl, Br, or I), hydroxy, $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, $C_6$, or $C_7$ alkoxy), which $C_1$-$C_7$ alkyl, $C_2$-$C_7$ alkenyl, $C_2$-$C_7$ alkynyl, or $C_1$-$C_6$ alkoxy can optionally be substituted with one or more (e.g., 0, 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, ethyl, or morpholinyl. In certain embodiments, $R^1$ can be a monovalent H, halogen (e.g., F, Cl, Br, or I), hydroxy, $C_1$-$C_7$ alkyl (e.g., $C_1$, $C_2$, $C_3$, $C_4$, $C_5$, $C_6$, or $C_7$ alkyl), or $C_1$-$C_6$ alkoxy ($C_1$, $C_2$, $C_3$, $C_4$, $C_5$, $C_6$, or $C_7$ alkoxy), which $C_1$-$C_7$ alkyl or $C_1$-$C_6$ alkoxy can optionally be substituted with one or more (e.g., 0, 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, ethyl, or morpholinyl. In some embodiments, $R^1$ is Cl, methyl, 2-(morpholinyl)ethoxy, or —OCH$_3$. In other embodiments, $R^1$ is not H.

In some embodiments, $R^2$ can be monovalent H, halogen (e.g., F, Cl, Br, or I), hydroxy, —CN, methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_2$-$C_7$ alkenyl, $C_2$-$C_7$ alkynyl, $C_2$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, $C_1$-$C_3$ alkyl, $C_1$-$C_3$ perfluoronated alkyl, or $C_1$-$C_3$ alkoxy. In other embodiments, $R^2$ can be monovalent H, halogen (e.g., F, Cl, Br, or I), hydroxy, —CN, methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_2$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, $C_1$-$C_3$ alkyl, $C_1$-$C_3$ perfluoronated alkyl, or $C_1$-$C_3$ alkoxy. In some embodiments, $R^2$ can be —CO-morpholin-4-yl, —CON(CH$_3$)$_2$, Cl, methyl, —CN, ethynyl, —CONH$_2$, —CON(CH$_3$)$_2$, 2-(morpholinyl)ethoxy, ethoxy, methoxy, 1H-pyrazol-4-yl, 1-methyl-pyrazol-4-yl, 1-(morpholin-4-yl)-pyrazol-4-yl, pyridin-3-yl, 2-methoxy-pyridin-5-yl, pyridin-4-yl, 3,5-dimethylisoxazol-4-yl, 1H-pyrrol-3-yl, 3,5-(dimethyl)-pyrazolyl, pyrazol-3-yl, 5-tetrazolyl, 1H-pyrazol-4-yl, 4-ethyl-piperazin-1-yl, perfluorinated methyl, or perfluorinated ethyl. In some embodiments, $R^2$ can be —CO-morpholin-4-yl, —CON(CH$_3$)$_2$, Cl, methyl, —CN, ethynyl, 2-(morpholinyl)ethoxy, ethoxy, or methoxy. In certain embodiments, $R^2$ can be 1H-pyrazol-4-yl, 1-methyl-pyrazol-4-yl, 1-(morpholin-4-yl)-pyrazol-4-yl, pyridin-3-yl, 2-methoxy-pyridin-5-yl, pyridin-4-yl, 3,5-dimethylisoxazol-4-yl, 1H-pyrrol-3-yl, 3,5-(di-methyl)-pyrazolyl, pyrazol-3-yl, 5-tetrazolyl, 1H-pyrazol-4-yl, or 4-ethyl-piperazin-1-yl. In some embodiments, $R^2$ can be perfluorinated methyl or perfluorinated ethyl. In other embodiments, $R^2$ is not H.

In some embodiments, $R^2$ can be isochromanyl (e.g., 3-isochromanyl), chromanyl (e.g., 7-chromanyl), pyrrolidinyl (e.g., 2-pyrrolidinyl), pyrrolinyl (e.g., 2-pyrroline-3-yl), imidazolidinyl (e.g., 2-imidazolidinyl), imidazolinyl (e.g., 2-imidazolin-4-yl), pyrazolidinyl (e.g., 2-pyrazolidinyl), pyrazolinyl (e.g., 3-pyrazoline-2-yl), piperidyl (e.g., 2-piperidyl), piperazinyl (e.g., 1-piperazinyl), indolinyl (e.g., 1-indolinyl), isoindolinyl (e.g., 1-isoindolinyl), quinuclidinyl (e.g., 2-quinuclidinyl), or morpholinyl (e.g., 3-morpholinyl), where each can be optionally substituted as described for $R^2$ (e.g., optionally substituted with one or more (e.g., 0, 1, 2, 3, 4, 5, or 6) of halogen (e.g., F, Cl, Br, or I), hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, $C_1$-$C_3$ alkyl, $C_1$-$C_3$ perfluoronated alkyl, or $C_1$-$C_3$ alkoxy). In other embodiments, $R^2$ can be thienyl (e.g., 2-thienyl), thianthrenyl (e.g., 2-thianthrenyl), furyl (e.g., 3-furyl), pyranyl (e.g., 2H-pyran-3-yl), isobenzofuranyl (e.g., 1-isobenzofuranyl), chromenyl (e.g., 2H-cromen-3-yl), xanthenyl (e.g., 2-xanthenyl), phenoxathiinyl (e.g., 2-phenoxathiinyl), 2H-pyrrolyl (e.g., 2H-pyrrol-3-yl), pyrrolyl (e.g., 3-pyrrolyl), imidazolyl (e.g., 2-imidazolyl), pyrazolyl (e.g., 1-pyrazolyl), isothiazolyl (e.g., 3-isothiazolyl), isoxazolyl (e.g., 3-isoxazolyl), pyridyl (e.g., 3-pyridyl), pyrazinyl, pyrimidinyl (e.g., 2-pyrimidinyl), pyridazinyl (e.g., 3-pyridazinyl), indolizinyl (e.g., 2-indolizinyl), isoindolyl (e.g., 2-isoindolyl), 3H-indolyl (e.g., 3H-indol-2-yl), indolyl (e.g., 1-indolyl), indazolyl (e.g., 1H-indazol-3-yl), purinyl (e.g., 8-purinyl), 4H-quinolizinyl (e.g., 4H-quinolizin-2-yl), isoquinolyl (e.g., 3-isoquinolyl), quinolyl (e.g., 2-quinolyl), phthalazinyl (e.g., 1-phthalazinyl), naphthyridinyl (e.g., 1,8-naphthyridin-2-yl), quinoxalinyl (e.g., 2-quinoxalinyl), quinazolinyl (2-quinazolinyl), cinnolinyl (e.g., 3-cinnolinyl), pteridinyl (e.g., 2-pteridinyl), 4aH-carbazolyl (e.g., 4aH-Carbazol-2-yl), carbazolyl (e.g., 2-carbazolyl), carbolinyl (e.g., carbolin-3-yl), phenanthridinyl (e.g., 3-phenanthridinyl), acridinyl (2-acridinyl), perimidinyl (e.g., 2-perimidinyl), phenanthrolinyl (e.g., 1,7-phenanthrolin-3-yl), phenazinyl (1-phenazinyl), phenasazinyl (e.g., 2-phenarsazinyl), phenothiazinyl (2-phenothiazinyl), furazanyl (e.g., 3-furazanyl), or phenoxazinyl (e.g., 2-phenoxazinyl), where each can be optionally substituted as described for $R^2$ (e.g., optionally substituted with one or more (e.g., 0, 1, 2, 3, 4, 5, or 6) of halogen (e.g., F, Cl, Br, or I), hydroxy, methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), heterocyclyl, aryl, heteroaryl, pyrrolyl, piperidyl, piperazinyl, morpholinyl, —CO-morpholin-4-yl, —CONH$_2$, —CON(CH$_3$)$_2$, $C_1$-$C_3$ alkyl, $C_1$-$C_3$ perfluorinated alkyl, or $C_1$-$C_3$ alkoxy).

In some embodiments, $R^3$ can be monovalent H, halogen (e.g., F, Cl, Br, or I), hydroxy, $C_1$-$C_3$ alkyl (e.g., $C_1$, $C_2$, or $C_3$ alkyl), $C_2$-$C_3$ alkenyl (e.g., $C_2$ or $C_3$ alkenyl), $C_2$-$C_3$ alkynyl (e.g., $C_2$ or $C_3$ alkynyl), or $C_1$-$C_2$ alkoxy (e.g., $C_1$ or $C_2$ alkoxy), which $C_1$-$C_3$ alkyl, $C_2$-$C_3$ alkenyl, $C_2$-$C_3$ alkynyl, or $C_1$-$C_2$ alkoxy can optionally be substituted with one or more (e.g., 0, 1, 2, 3, 4, 5, or 6) of halogen (e.g., F, Cl, Br, or I), hydroxy, methanoyl (—COH), carboxy (—CO$_2$H), cyano (—CN), ethynyl (—CCH), sulfo (—SO$_3$H), methyl, or ethyl. In other embodiments, $R^3$ can be monovalent H, halogen (e.g., F, Cl, Br, or I), hydroxy, $C_1$-$C_3$ alkyl (e.g., $C_1$, $C_2$, or $C_3$ alkyl), or $C_1$-$C_2$ alkoxy (e.g., $C_1$ or $C_2$ alkoxy), which $C_1$-$C_3$ alkyl or $C_1$-$C_2$ alkoxy can optionally be substituted with one or more (e.g., 0, 1, 2, 3, 4, 5, or 6) of halogen (e.g., F, Cl, Br, or I), hydroxy, methanoyl (—COH), carboxy (—CO$_2$H), cyano (—CN), ethynyl (—CCH), sulfo (—SO$_3$H), methyl, or ethyl. In some embodiments, $R^3$ can be perfluorinated methyl or perfluorinated ethyl. In some embodiments, $R^3$ can be H, methoxy, which methoxy is optional substituted with one, two, or three halogen (e.g., Cl, F, Br, or I). In some embodiments, $R^3$ can be H or methoxy.

In some embodiments, $R^4$ can be monovalent H, halogen (e.g., F, Cl, Br, or I), hydroxy, methanoyl (—COH), carboxy (—CO$_2$H), nitro (—NO$_2$), cyano (—CN), sulfo (—SO$_3$H), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), or $C_1$-$C_3$ alkoxy (e.g., $C_1$, $C_2$, or $C_3$ alkoxy), which $C_1$-$C_4$ alkyl, $C_2$-$C_4$ alkenyl, $C_2$-$C_4$ alkynyl, or $C_1$-$C_3$ alkoxy can optionally be substituted with one or more (e.g., 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, or ethyl. In other embodiments, $R^4$ can be monovalent H, halogen (e.g., F, Cl, Br, or I), hydroxy, methanoyl (—COH), carboxy (—CO$_2$H), nitro (—NO$_2$), cyano (—CN), sulfo (—SO$_3$H), $C_1$-$C_4$ alkyl (e.g., $C_1$, $C_2$, $C_3$, or $C_4$ alkyl), or $C_1$-$C_3$ alkoxy (e.g., $C_1$, $C_2$, or $C_3$ alkoxy), which $C_1$-$C_4$ alkyl or $C_1$-$C_3$ alkoxy can optionally be substituted with one or more (e.g., 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, or ethyl. In some embodiments, $R^4$ can be F, Cl, Br, methyl, perfluorinated methyl, or methoxy.

In some embodiments, $R^5$ can be monovalent H, halogen (e.g., F, Cl, Br, or I), hydroxy, methanoyl (—COH), carboxy (—CO$_2$H), nitro (—NO$_2$), cyano (—CN), sulfo (—SO$_3$H), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), or $C_1$-$C_3$ alkoxy (e.g., $C_1$, $C_2$, or $C_3$ alkoxy), which $C_1$-$C_4$ alkyl, $C_2$-$C_4$ alkenyl, $C_2$-$C_4$ alkynyl, or $C_1$-$C_3$ alkoxy can optionally be substituted with one or more (e.g., 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, or ethyl. In other embodiments, $R^5$ can be monovalent H, halogen (e.g., F, Cl, Br, or I), hydroxy, methanoyl (—COH), carboxy (—CO$_2$H), nitro (—NO$_2$), cyano (—CN), sulfo (—SO$_3$H), $C_1$-$C_4$ alkyl (e.g., $C_1$, $C_2$, $C_3$, or $C_4$ alkyl), or $C_1$-$C_3$ alkoxy (e.g., $C_1$, $C_2$, or $C_3$ alkoxy), which $C_1$-$C_4$ alkyl or $C_1$-$C_3$ alkoxy can optionally be substituted with one or more (e.g., 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, or ethyl. In some embodiments, $R^5$ can be F, Cl, Br, methyl, ethyl, or methoxy. In some embodiments, $R^5$ is not F, Cl, Br, or perfluorinated methyl, or is not substituted with halogen (e.g., F, Cl, Br, or I), hydroxy, methanoyl (—COH), carboxy (—CO$_2$H), nitro (—NO$_2$), cyano (—CN), ethynyl (—CCH), or sulfo (—SO$_3$H).

In some embodiments, $R^6$ can be monovalent H, halogen (e.g., F, Cl, Br, or I), hydroxy, methanoyl (—COH), carboxy (—CO$_2$H), nitro (—NO$_2$), cyano (—CN), sulfo (—SO$_3$H), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), or $C_1$-$C_3$ alkoxy (e.g., $C_1$, $C_2$, or $C_3$ alkoxy), which $C_1$-$C_4$ alkyl, $C_2$-$C_4$ alkenyl, $C_2$-$C_4$ alkynyl, or $C_1$-$C_3$ alkoxy can optionally be substituted with one or more (e.g., 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, or ethyl. In other embodiments, $R^6$ can be monovalent H, halogen (e.g., F, Cl, Br, or I), hydroxy, methanoyl (—COH), carboxy (—CO$_2$H), nitro (—NO$_2$), cyano (—CN), sulfo (—SO$_3$H), $C_1$-$C_4$ alkyl (e.g., $C_1$, $C_2$, $C_3$, or $C_4$ alkyl), or $C_1$-$C_3$ alkoxy (e.g., $C_1$, $C_2$, or $C_3$ alkoxy), which $C_1$-$C_4$ alkyl or $C_1$-$C_3$ alkoxy can optionally be substituted with one or more (e.g., 1, 2, 3, 4, 5, or 6) of halogen (e.g., F, Cl, Br, or I), hydroxy, methanoyl (—COH), carboxy (—CO$_2$H), nitro (—NO$_2$), cyano (—CN), ethynyl (—CCH), sulfo (—SO$_3$H), methyl, or ethyl. In some embodiments, $R^6$ can be F, Cl, Br, methyl, perfluorinated methyl, or methoxy.

In certain embodiments, Y can be a bivalent

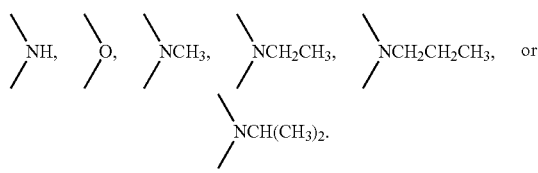

In some embodiments, Y can be

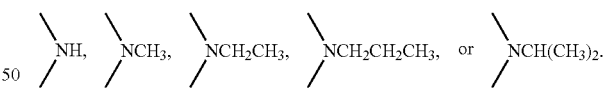

In other embodiments, Y can be

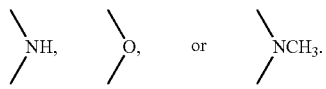

In other embodiments, Y can be

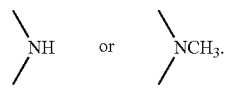

The wavy bond from Y to R⁷ (i.e., ⌇ ) indicates that, in some instances, there is a chiral center at the R⁷ attachment carbon. In some embodiments, where there is a chiral center at the R⁷ attachment carbon, the wavy bond can indicate an R chiral center, an S chiral center, or a racemate (e.g., compounds I-43, I-44, and I-54). In certain embodiments, ⌇, can be ▱, ◤, ▰, ◣, or ——.

In some embodiments, R⁷ can be

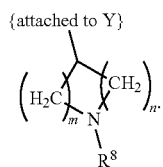

In other embodiments R⁷ can be piperid-2-yl, piperid-3-yl, piperid-4-yl, pyrrolidin-2-yl, pyrrolidin-3-yl, or azetidyl. In some embodiments, R⁸ can be H, $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), methanoyl (—COH), ethanoyl (—COCH₃), benzoyl (—COC₆H₅), toluoyl, carboxy (—CO₂H), nitro (—NO₂), cyano (—CN), or —COCH₂CN. In some embodiments, R⁸ can be H, ethanoyl (—COCH₃), benzoyl (—COC₆H₅), ethynyl (—CCH), or —COCH₂CN.

In certain embodiments, n can be 0, 1, 2, 3, 4, or 5. In some embodiments, n can be 1, 2, or 3. In other embodiments, m can be 0, 1, 2, 3, 4, or 5. In some embodiments, m can be 1, 2, or 3. In some instances, n+m can be at least 1.

In some embodiments, the compounds of Formula (I) can be those specified in Table 1.

TABLE 1

| Compound Number | Structure | NCGC ID |
|---|---|---|
| I-1 | 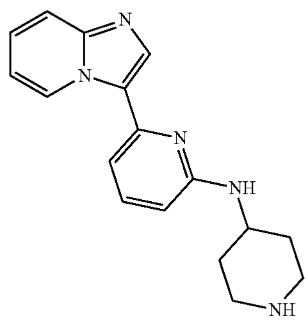 [SMILES: c1cc(NC2CCNCC2)nc(-c2cnc3ccccn23)c1] | None |
| I-2 | 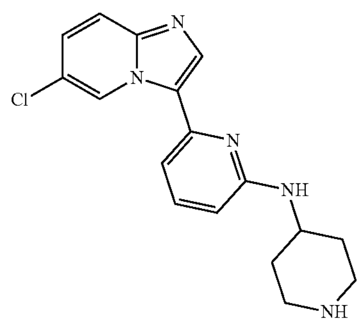 [SMILES: Clc1ccc2ncc(-c3cccc(NC4CCNCC4)n3)n2c1] | NCGC00249350 |
| I-3 | 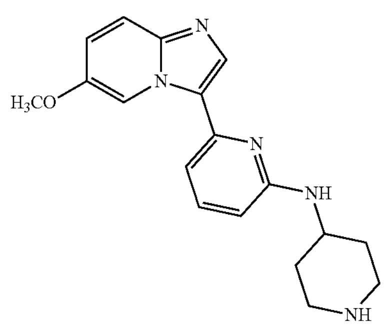 [SMILES: COc1ccc2ncc(-c3cccc(NC4CCNCC4)n3)n2c1] | None |

TABLE 1-continued

| Compound Number | Structure | NCGC ID |
|---|---|---|
| I-4 | 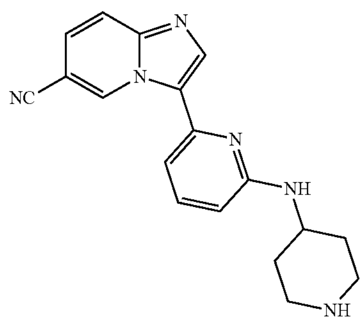 [SMILES: N#Cc1ccc2ncc(-c3cccc(NC4CCNCC4)n3)n2c1] | None |
| I-5 | 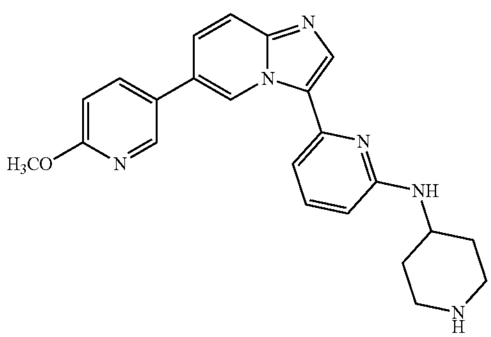 [SMILES: COc1ccc(-c2ccc3ncc(-c4cccc(NC5CCNCC5)n4)n3c2)cn1] | None |
| I-6 | 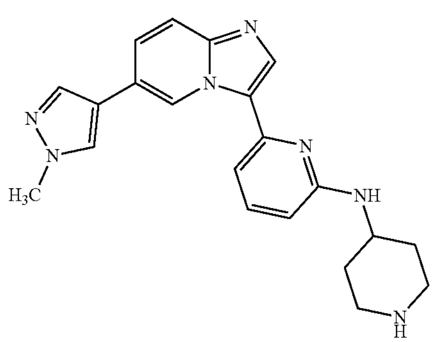 [SMILES: Cn1cc(-c2ccc3ncc(-c4cccc(NC5CCNCC5)n4)n3c2)cn1] | None |
| I-7 | 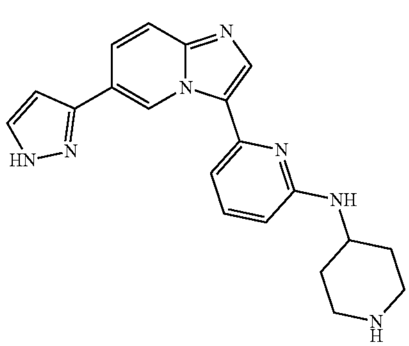 [SMILES: c1cc(NC2CCNCC2)nc(-c2cnc3ccc(-c4cc[nH]n4)cn23)c1] | None |

TABLE 1-continued

| Compound Number | Structure | NCGC ID |
|---|---|---|
| I-8 | 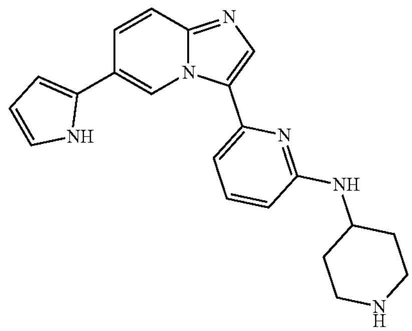 [SMILES: c1cc(NC2CCNCC2)nc(-c2cnc3ccc(-c4ccc[nH]4)cn23)c1] | None |
| I-9 | 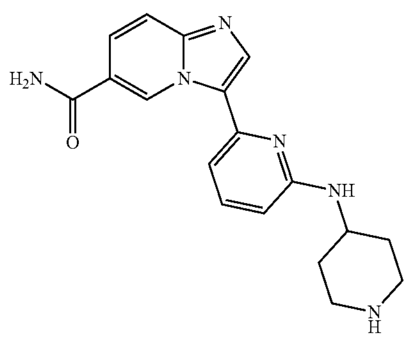 [SMILES: NC(=O)c1ccc2ncc(-c3cccc(NC4CCNCC4)n3)n2c1] | None |
| I-10 | 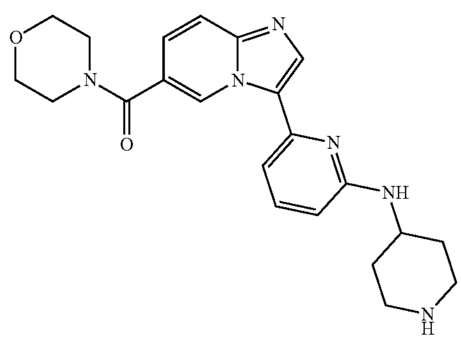 [SMILES: O=C(c1ccc2ncc(-c3cccc(NC4CCNCC4)n3)n2c1)N1CCOCC1] | None |
| I-11 | 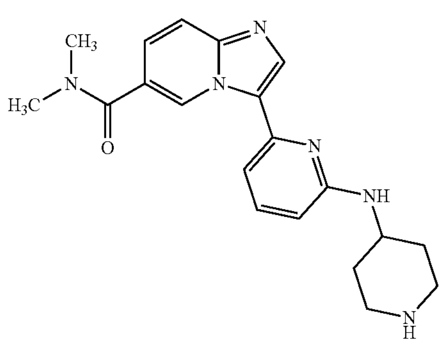 [SMILES: CN(C)C(=O)c1ccc2ncc(-c3cccc(NC4CCNCC4)n3)n2c1] | None |

TABLE 1-continued

| Compound Number | Structure | NCGC ID |
|---|---|---|
| I-12 | 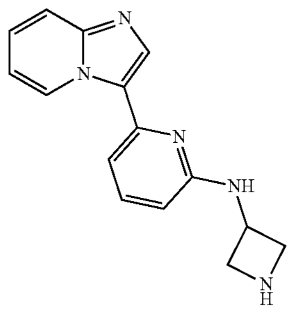 [SMILES: c1cc(NC2CNC2)nc(-c2cnc3ccccn23)c1] | NCGC00262328 |
| I-13 | 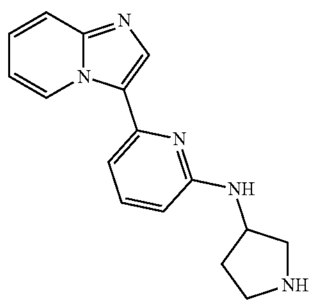 [SMILES: c1cc(NC2CCNC2)nc(-c2cnc3ccccn23)c1] | None |
| I-14 | 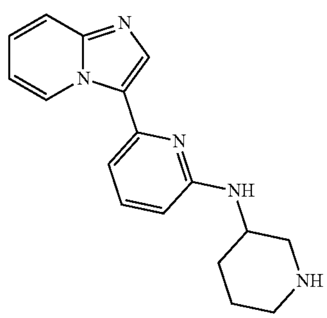 [SMILES: c1cc(NC2CCCNC2)nc(-c2cnc3ccccn23)c1] | None |
| I-15 | 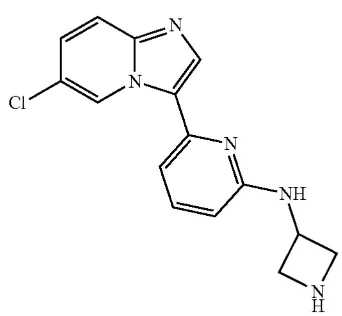 [SMILES: Clc1ccc2ncc(-c3cccc(NC4CNC4)n3)n2c1] | NCGC00241410 |
| I-16 | 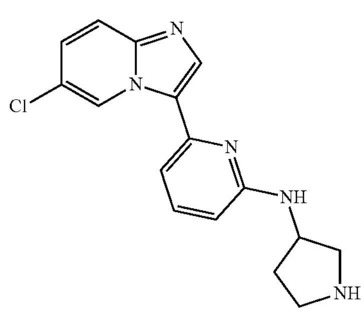 [SMILES: Clc1ccc2ncc(-c3cccc(NC4CCNC4)n3)n2c1] | NCGC00249372 |

TABLE 1-continued

| Compound Number | Structure | NCGC ID |
|---|---|---|
| I-17 | 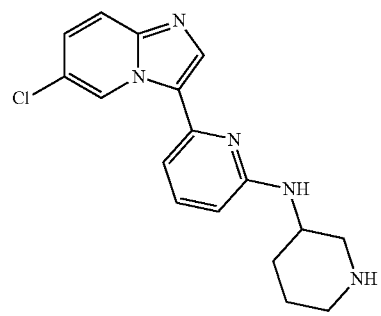 [SMILES: Clc1ccc2ncc(-c3cccc(NC4CCCNC4)n3)n2c1] | NCGC00249373 |
| I-18 | 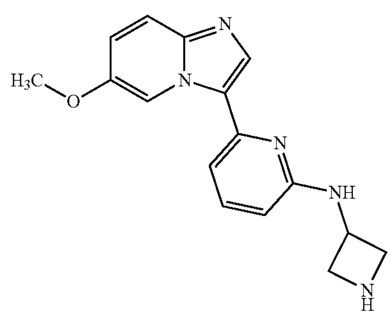 [SMILES: COc1ccc2ncc(-c3cccc(NC4CNC4)n3)n2c1] | None |
| I-19 | 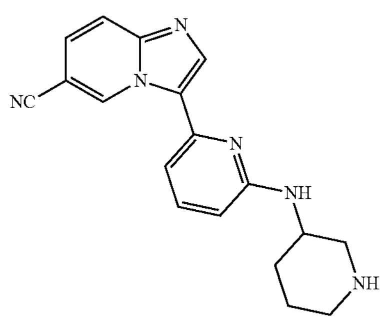 [SMILES: N#Cc1ccc2ncc(-c3cccc(NC4CCCNC4)n3)n2c1] | None |
| I-20 | 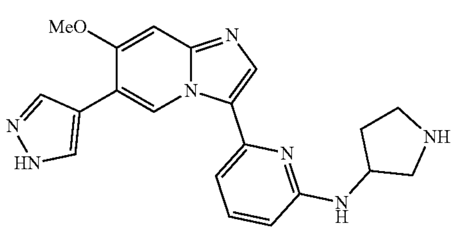 [SMILES: COc1cc2ncc(-c3cccc(NC4CCNC4)n3)n2cc1-c1cn[nH]c1] | NCGC00262327 |
| I-21 | 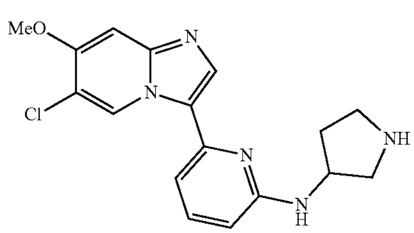 [SMILES: COc1cc2ncc(-c3cccc(NC4CCNC4)n3)n2cc1Cl] | NCGC00262326 |

TABLE 1-continued
| Compound Number | Structure | NCGC ID |
|---|---|---|
| I-22 | 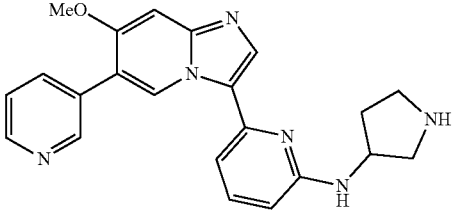 [SMILES: COc1cc2ncc(-c3cccc(NC4CCNC4)n3)n2cc1-c1cccnc1] | NCGC00371479 |
| I-23 | 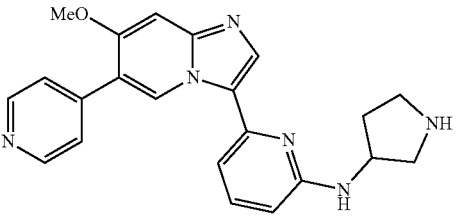 [SMILES: COc1cc2ncc(-c3cccc(NC4CCNC4)n3)n2cc1-c1ccncc1] | NCGC00371480 |
| I-24 | 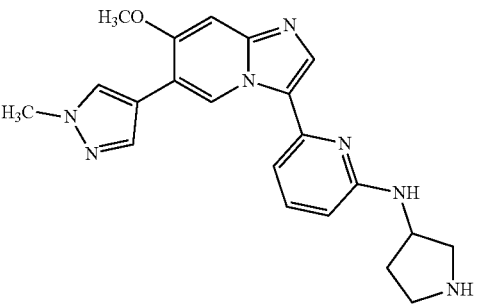 [SMILES: COc1cc2ncc(-c3cccc(NC4CCNC4)n3)n2cc1-c1cnn(C)c1] | NCGC00371481 |
| I-25 | 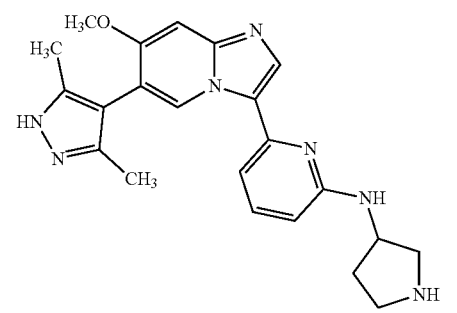 [SMILES: COc1cc2ncc(-c3cccc(NC4CCNC4)n3)n2cc1-c1c(C)n[nH]c1C] | NCGC00371482 |
| I-26 | 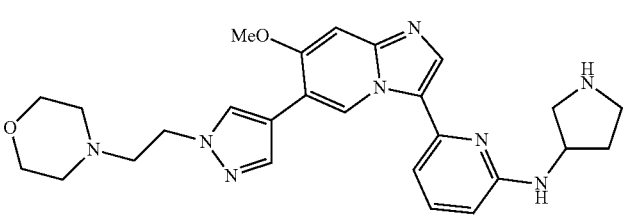 [SMILES: COc1cc2ncc(-c3cccc(NC4CCNC4)n3)n2cc1-c1cnn(CCN2CCOCC2)c1] | NCGC00371483 |
| I-27 | 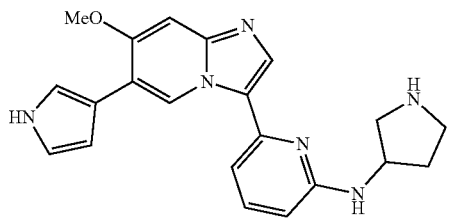 [SMILES: COc1cc2ncc(-c3cccc(NC4CCNC4)n3)n2cc1-c1cc[nH]c1] | NCGC00371484 |

TABLE 1-continued
| Compound Number | Structure | NCGC ID |
|---|---|---|
| I-28 | 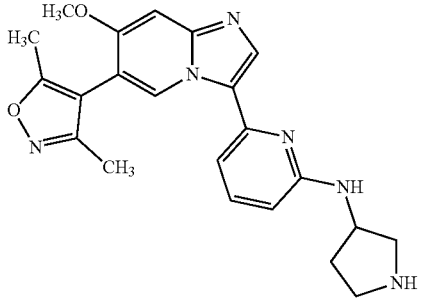 [SMILES: COc1cc2ncc(-c3cccc(NC4CCNC4)n3)n2cc1-c1c(C)noc1C] | NCGC00371488 |
| I-29 | 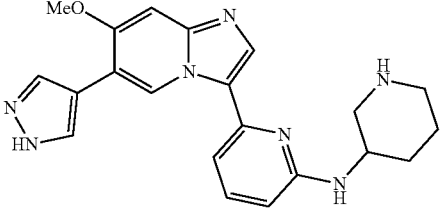 [SMILES: COc1cc2ncc(-c3cccc(NC4CCCNC4)n3)n2cc1-c1cn[nH]c1] | NCGC00371485 |
| I-30 | 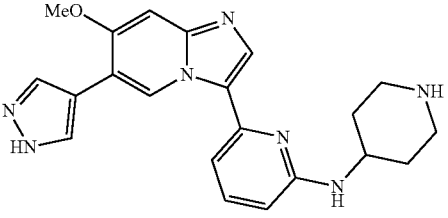 [SMILES: COc1cc2ncc(-c3cccc(NC4CCNCC4)n3)n2cc1-c1cn[nH]c1] | NCGC00371486 |
| I-31 | 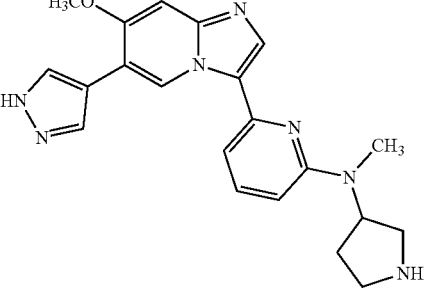 | NCGC00371487 |
| I-32 | 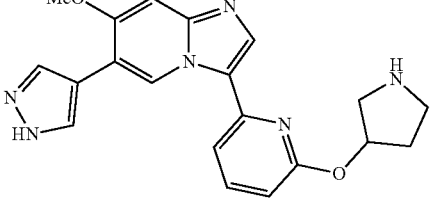 | NCGC00371852 |
| I-33 | 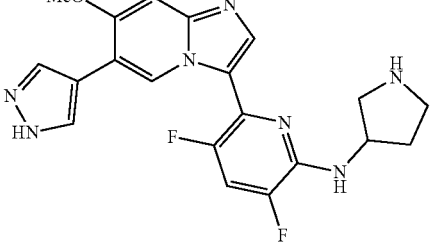 | NCGC00371853 |

TABLE 1-continued

| Compound Number | Structure | NCGC ID |
|---|---|---|
| I-34 | 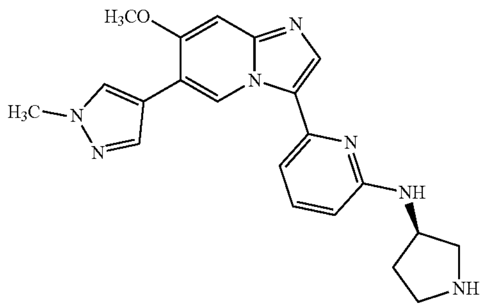 [SMILES: COc1cc2ncc(-c3cccc(N[C@@H]4CCNC4)n3)n2cc1-c1cnn(C)c1] | See I-24 |
| I-35 | 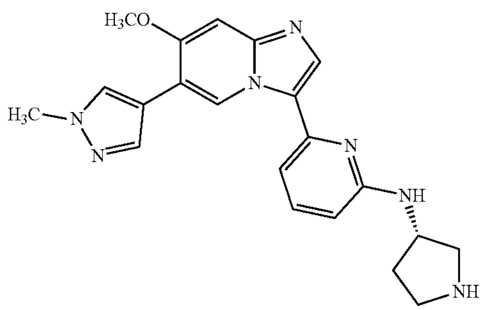 [SMILES: COc1cc2ncc(-c3cccc(N[C@H]4CCNC4)n3)n2cc1-c1cnn(C)c1] | See I-24 |
| I-36 | 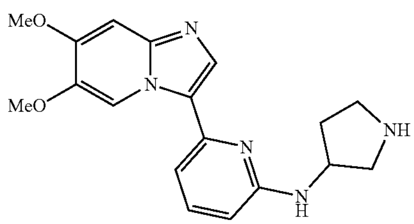 [SMILES: COc1cc2ncc(-c3cccc(NC4CCNC4)n3)n2cc1OC] | NCGC00371850 |
| I-37 | 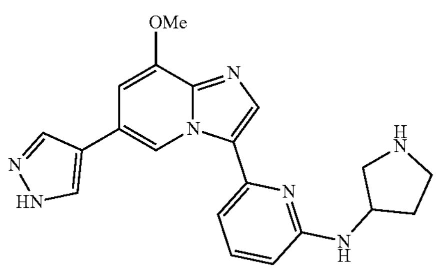 [SMILES: COc1cc(-c2cn[nH]c2)cn2c(-c3cccc(NC4CCNC4)n3)cnc12] | NCGC00371857 |
| I-38 | 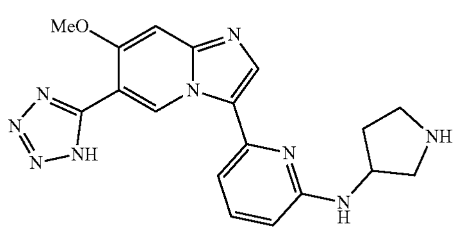 [SMILES: COc1cc2ncc(-c3cccc(NC4CCNC4)n3)n2cc1-c1nnn[nH]1] | NCGC00371858 |
| I-39 | 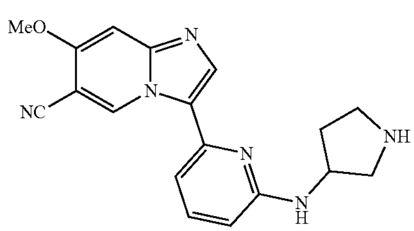 [SMILES: COc1cc2ncc(-c3cccc(NC4CCNC4)n3)n2cc1C#N] | NCGC00371859 |

TABLE 1-continued

| Compound Number | Structure | NCGC ID |
|---|---|---|
| I-40 | 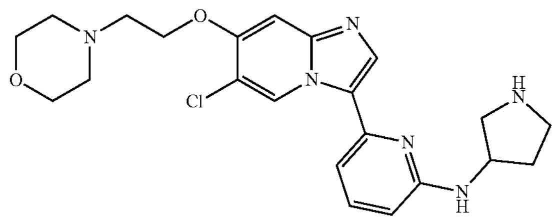 [SMILES: Clc1cn2c(-c3cccc(NC4CCNC4)n3)cnc2cc1OCCN1CCOCC1] | NCGC00371957 |
| I-41 | 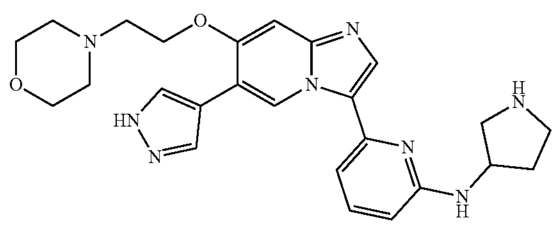 [SMILES: c1cc(NC2CCNC2)nc(-c2cnc3cc(OCCN4CCOCC4)c(-c4cn[nH]c4)cn23)c1] | NCGC00371958 |
| I-42 | 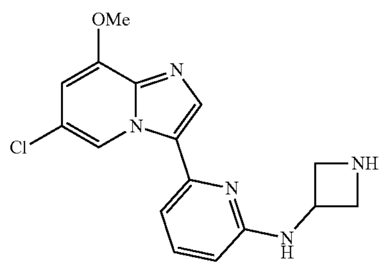 [SMILES: COc1cc(Cl)cn2c(-c3cccc(NC4CNC4)n3)cnc12] | NCGC00262331 |
| I-43 | 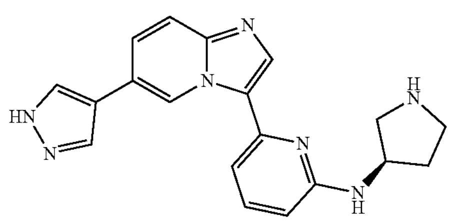 [SMILES: c1cc(N[C@@H]2CCNC2)nc(-c2cnc3ccc(-c4cn[nH]c4)cn23)c1] | NCGC00262376 |
| I-44 | 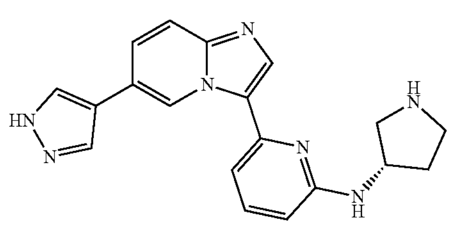 [SMILES: c1cc(N[C@H]2CCNC2)nc(-c2cnc3ccc(-c4cn[nH]c4)cn23)c1] | NCGC00262377 |
| I-45 | 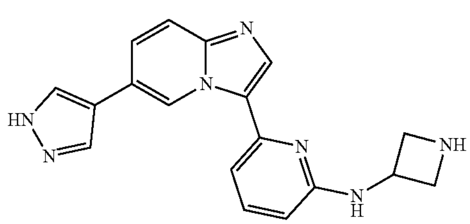 [SMILES: c1cc(NC2CNC2)nc(-c2cnc3ccc(-c4cn[nH]c4)cn23)c1] | NCGC00249356 |

TABLE 1-continued

| Compound Number | Structure | NCGC ID |
|---|---|---|
| I-46 | 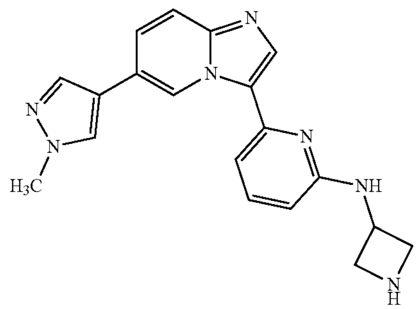 [SMILES: Cn1cc(-c2ccc3ncc(-c4cccc(NC5CNC5)n4)n3c2)cn1] | NCGC00249357 |
| I-47 | 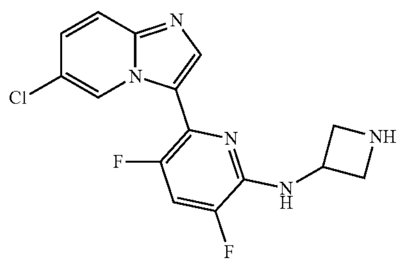 [SMILES: Fc1cc(F)c(-c2cnc3ccc(Cl)cn23)nc1NC1CNC1] | NCGC00249846 |
| I-48 | 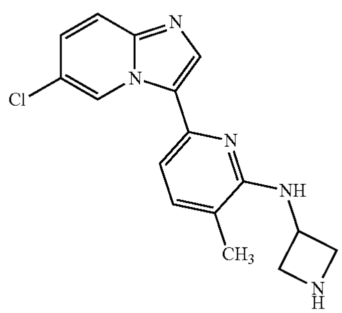 [SMILES: Cc1ccc(-c2cnc3ccc(Cl)cn23)nc1NC1CNC1] | NCGC00262329 |
| I-49 | 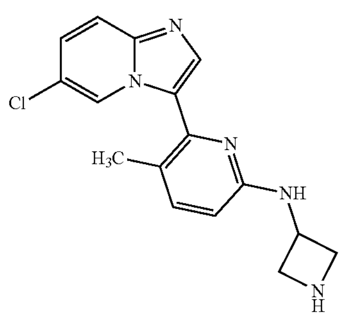 [SMILES: Cc1ccc(NC2CNC2)nc1-c1cnc2ccc(Cl)cn12] | NCGC00262330 |
| I-50 | 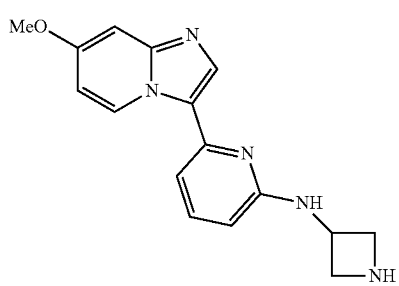 [SMILES: COc1ccn2c(-c3cccc(NC4CNC4)n3)cnc2c1] | NCGC00249829 |

TABLE 1-continued

| Compound Number | Structure | NCGC ID |
|---|---|---|
| I-51 | 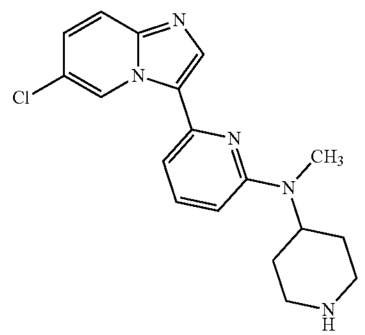 [SMILES: CN(c1cccc(-c2cnc3ccc(Cl)cn23)n1)C1CCNCC1] | NCGC00249832 |
| I-52 | 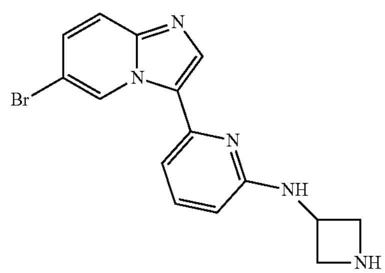 [SMILES: Brc1ccc2ncc(-c3cccc(NC4CNC4)n3)n2c1] | NCGC00249354 |
| I-53 | 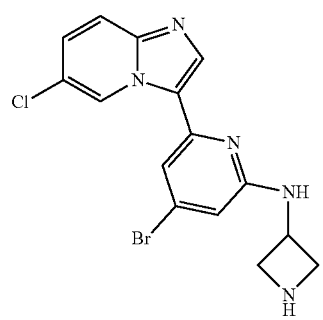 [SMILES: Clc1ccc2ncc(-c3cc(Br)cc(NC4CNC4)n3)n2c1] | NCGC00249838 |
| I-54 | 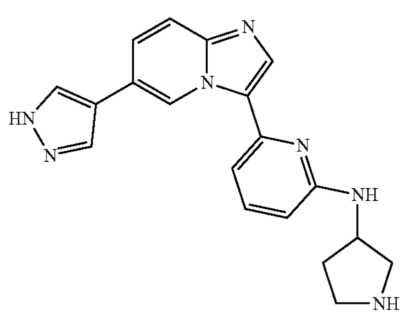 [SMILES: c1cc(NC2CCNC2)nc(-c2cnc3ccc(-c4cn[nH]c4)cn23)c1] | NCGC00249841 |
| I-55 | 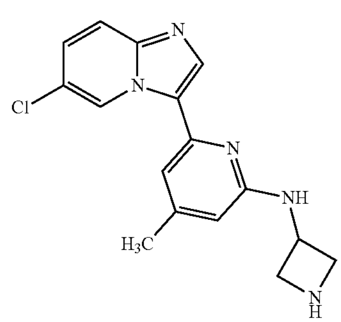 [SMILES: Cc1cc(NC2CNC2)nc(-c2cnc3ccc(Cl)cn23)c1] | NCGC00249842 |

TABLE 1-continued

| Compound Number | Structure | NCGC ID |
|---|---|---|
| I-56 | 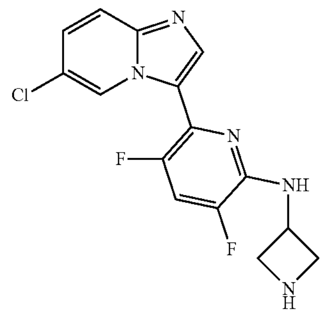 [SMILES: Fc1cc(F)c(-c2cnc3ccc(Cl)cn23)nc1NC1CNC1] | NCGC00249846 |
| I-57 | 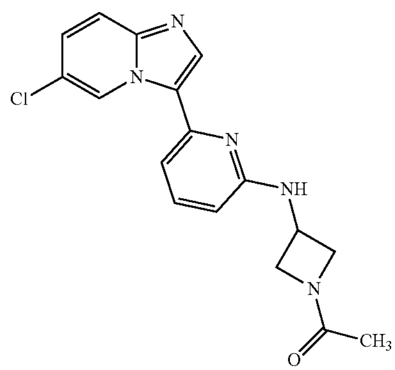 [SMILES: CC(=O)N1CC(Nc2cccc(-c3cnc4ccc(Cl)cn34)n2)C1] | NCGC00249371 |
| I-58 | 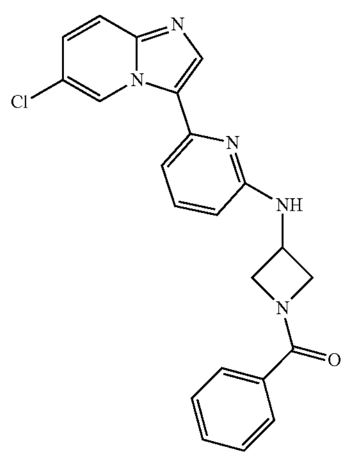 [SMILES: O=C(c1ccccc1)N1CC(Nc2cccc(-c3cnc4ccc(Cl)cn34)n2)C1] | NCGC00249374 |
| I-59 | 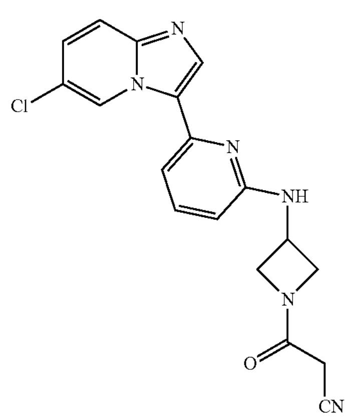 [SMILES: N#CCC(=O)N1CC(Nc2cccc(-c3cnc4ccc(Cl)cn34)n2)C1] | NCGC00249370 |

TABLE 1-continued

| Compound Number | Structure | NCGC ID |
| --- | --- | --- |
| I-60 | 6-cyano-imidazo[1,2-a]pyridin-3-yl connected to pyridin-2-yl with 6-(azetidin-3-ylamino) substituent | NCGC00249366 |
| I-61 | 7-methyl-imidazo[1,2-a]pyridin-3-yl connected to pyridin-2-yl with 6-(azetidin-3-ylamino) substituent | NCGC00249375 |
| I-62 | 6,7-dichloro-imidazo[1,2-a]pyridin-3-yl connected to pyridin-2-yl with 6-(azetidin-3-ylamino) substituent | NCGC00249368 |
| I-63 | 7-chloro-imidazo[1,2-a]pyridin-3-yl connected to pyridin-2-yl with 6-(azetidin-3-ylamino) substituent | NCGC00249362 |
| I-64 | 6-(4-ethylpiperazin-1-yl)-imidazo[1,2-a]pyridin-3-yl connected to pyridin-2-yl with 6-(azetidin-3-ylamino) substituent | NCGC00249363 |

TABLE 1-continued

| Compound Number | Structure | NCGC ID |
|---|---|---|
| I-65 | 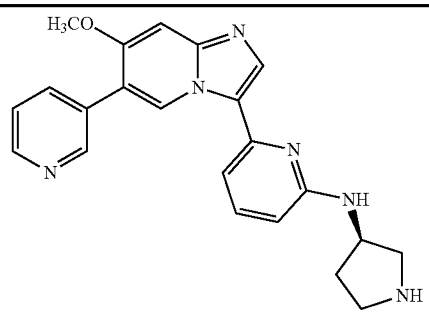 | See I-22 |
| I-66 | 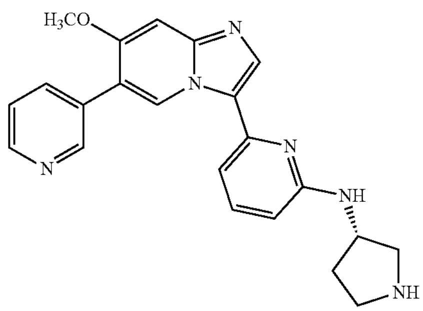 [SMILES: COc1cc2ncc(-c3cccc(N[C@H]4CCNC4)n3)n2cc1-c1cccnc1] | See I-22 |
| I-67 | 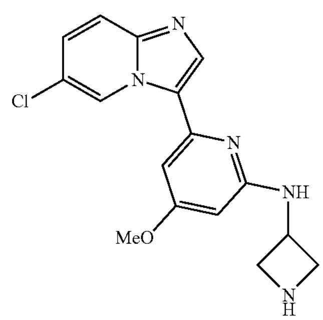 [SMILES: COc1cc(NC2CNC2)nc(-c2cnc3ccc(Cl)cn23)c1] | NCGC00249349 |
| I-68 | 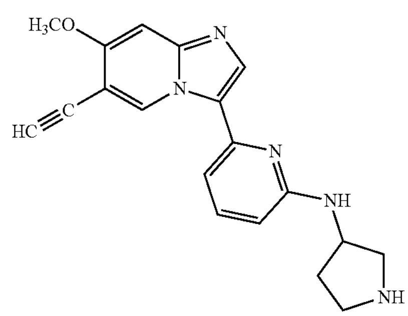 [SMILES: C#Cc1cn2c(-c3cccc(NC4CCNC4)n3)cnc2cc1OC] | NCGC00378320 |

In some embodiments, one or more of compounds I-1, I-2, I-3, I-4, I-5, I-6, I-7, I-8, I-9, I-10, I-11, I-12, I-13, I-14, I-15, I-16, I-17, I-18, or I-19 are excluded from the compounds of the invention. In other embodiments, all of compounds I-1, I-2, I-3, I-4, I-5, I-6, I-7, I-8, I-9, I-10, I-11, I-12, I-13, I-14, I-15, I-16, I-17, I-18, and I-19 are excluded from the compounds of the invention. In certain embodiments, compounds I-2 and I-15 are excluded from the compounds of the invention.

In some embodiments, the compounds of the invention include one or more of I-2, I-15, I-20, I-22, I-24, I-26, I-27, I-42, I-53, and I-54. In some embodiments, the compounds of the invention include one or more of I-2, I-15, I-20, I-22, I-24, I-26, I-27, I-42, I-43, I-44, I-53, and I-54. In some embodiments, the compounds of the invention include one or more of I-20, I-22, I-24, I-26, I-27, I-42, I-53, and I-54. In some embodiments, the compounds of the invention include one or more of I-20, I-22, I-24, I-26, I-27, I-42, I-43, I-44, I-53, and I-54. In other embodiments, the compounds of the invention include one or more of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, and I-68. In other embodiments, the compounds of the invention include one or more of I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, I-54, I-55, I-56, I-57, I-58, I-59, I-60, I-61, I-62, I-63, I-64, I-65, I-66, I-67, and I-68.

In some embodiments, if Y is —NH—; $R^1$ is H; $R^3$ is H; $R^4$ is H; $R^5$ is H; $R^6$ is H; and $R^8$ is H, then
(a) $R^2$ is not H, Cl, methoxy, or CN, and
(b) $R^7$ is not

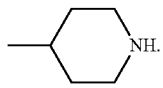

In some embodiments, if Y is —NH—; $R^1$ is H; $R^3$ is H; $R^4$ is H; $R^5$ is H; $R^6$ is H; and $R^8$ is H, then
(a) $R^2$ is not H, Cl, F, Br, I, methoxy, ethoxy, or CN, and
(b) $R^7$ is not

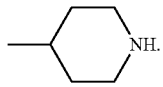

In some embodiments, if Y is —NH—; $R^1$ is H; $R^3$ is H; $R^4$ is H; $R^5$ is H; $R^6$ is H; and $R^8$ is H, then
(a) $R^2$ can be hydroxy, methanoyl (—COH), carboxy (—$CO_2$H), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), $C_3$-$C_6$ alkoxy (e.g., $C_3$, $C_4$, $C_5$, or $C_6$ alkoxy), cycloalkyl, heterocyclyl, aryl, or heteroaryl, which methanoyl (—COH), carboxy (—$CO_2$H), $C_1$-$C_7$ alkyl, $C_2$-$C_7$ alkenyl, $C_2$-$C_7$ alkynyl, $C_3$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), hydroxy, methanoyl (—COH), carboxy (—$CO_2$H), nitro (—$NO_2$), —$NH_2$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CON(CH_3)_2$, $C_1$-$C_3$ alkyl, $C_1$-$C_3$ perfluoronated alkyl, or $C_1$-$C_3$ alkoxy,
and
(b) $R^7$ is not

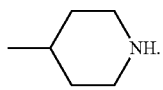

In some embodiments, if Y is —NH—; $R^1$ is H; $R^3$ is H; $R^4$ is H; $R^5$ is H; $R^6$ is H; and $R^8$ is H, then
(a) $R^2$ can be hydroxy, methanoyl (—COH), carboxy (—$CO_2$H), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), $C_5$-$C_6$ alkoxy (e.g., $C_5$ or $C_6$ alkoxy), cycloalkyl, heterocyclyl, aryl, or heteroaryl, which methanoyl (—COH), carboxy (—$CO_2$H), $C_1$-$C_7$ alkyl, $C_2$-$C_7$ alkenyl, $C_2$-$C_7$ alkynyl, $C_5$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), hydroxy, methanoyl (—COH), carboxy (—$CO_2$H), nitro (—$NO_2$), —$NH_2$, —$N(CH_3)_2$, cyano (—CN), ethynyl (—CCH), propynyl, sulfo (—$SO_3$H), heterocyclyl, aryl, heteroaryl, pyrrolyl, piperidyl, piperazinyl, morpholinyl, —CO-morpholin-4-yl, —$CONH_2$, —$CON(CH_3)_2$, $C_1$-$C_3$ alkyl, $C_1$-$C_3$ perfluoronated alkyl, or $C_1$-$C_3$ alkoxy,
and
(b) $R^7$ is not

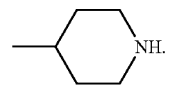

In some embodiments, the compounds of Formula (I) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, simple derivatives of the compounds (e.g., ethers, esters, or amides) which have desirable retention and release characteristics but which are easily hydrolyzed by body pH, enzymes, or other suitable means, can be employed.

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In some embodiments, the compounds of the invention can inhibit the activity of one or more of FLT3 (FMS-Like Tyrosine kinase 3), mutations of FLT3 (e.g., mutations in the juxamembranal region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation), IRAK4 (Interleukin-1 Receptor Associated Kinase 4), mutations of IRAK4, IRAK1 (Interleukin-1 Receptor Associated Kinase 1), or mutations of IRAK1. In some embodiments, the compounds of the invention can inhibit the activity of one or both of FLT3 and mutations of FLT3 (e.g., mutations in the juxamembranal region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation) and optionally inhibits one or more of IRAK4, mutations of IRAK4, IRAK1, or mutations of IRAK1. In some embodiments, the compounds of the invention can inhibit the activity of one or both of FLT3 and mutations of FLT3 (e.g., mutations in the juxamembranal region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation) and optionally inhibits one or both of IRAK4 and IRAK1.

In certain embodiments, one or more compounds of the invention (e.g., Formula (I)) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds of the invention (e.g., Formula (I)) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more compounds of the invention (e.g., Formula (I)). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size or blood cell count.

In some embodiments, one or more compounds of the invention (e.g., Formula (I)) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more compounds of the invention such as Formula (I)) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of administering or treating an organism, which can involve treatment with an amount of at least one compound of the invention (e.g., Formula (I)) that is effective to treat the disease, condition, or disorder that the organism has, or is suspected of having, or is susceptible to, or to bring about a desired physiological effect. In some embodiments, the composition or pharmaceutical composition comprises at least one compound of the invention (e.g., Formula (I)) which can be administered to an animal (e.g., mammals, primates, monkeys, or humans) in an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention (e.g., Formula (I)) can be administered in combination with one or more other therapeutic agents for a given disease, condition, or disorder.

In some embodiments, the compositions can include a unit dose of one or more compounds of the invention (e.g., Formula (I)) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Administration Routes and Treatments of Disease

The compounds of the invention (e.g., Formula (I)) can be administered to animals by any number of suitable administration routes or formulations. The compounds of the invention (e.g., Formula (I)) of the invention can also be used to treat animals for a variety of diseases. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of the compounds of the invention (e.g., Formula (I)) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal, the particular disease (e.g., cancer or MDS), and the severity of the disease (e.g., stage or severity of cancer or MDS). Of course, combinations of administration routes can be administered, as desired.

Some embodiments of the invention include a method for providing a subject with a composition comprising one or more compounds of the invention (e.g., Formula (I)) described herein (e.g., a pharmaceutical composition) which comprises one or more administrations of one or more such compositions; the compositions may be the same or different if there is more than one administration.

Diseases that can be treated in an animal (e.g., mammals, porcine, canine, avian (e.g., chicken), bovine, feline, primates, rodents, monkeys, rabbits, mice, rats, and humans) using a compound of the invention (e.g., Formula (I)) include, but are not limited to cancers, blood disorders (e.g., disorders of hematopoietic stem cells in the bone marrow or disorders related to myeloid lineage), myelodysplastic syndromes ("MDS"), myeloproliferative disease, and diseases (e.g., cancers) related to mutations in FLT3 (e.g., mutations in the juxamembranal region of FLT3, mutations in the kinase domain of FLT3, FLT3 point mutations, FLT3 internal tandem duplication mutations, the FLT3-ITD mutation, the D835Y FLT3 mutation, the D835V FLT3 mutation, the F691L FLT3 mutation, or the R834Q FLT3 mutation).

In certain embodiments, MDS that can be treated in an animal (e.g., mammals, porcine, canine, avian (e.g., chicken), bovine, feline, primates, rodents, monkeys, rabbits, mice, rats, and humans) using a compound of the invention (e.g., Formula (I)) include but are not limited to MDS with a splicing factor mutation, MDS with a mutation in isocitrate dehydrogenase 1, MDS with a mutation in isocitrate dehydrogenase 2, refractory cytopenia with unilineage dysplasia (e.g., refractory anemia, refractory neutropenia, and refractory thrombocytopenia), refractory anemia with ring sideroblasts, refractory cytopenia with multilineage dysplasia (e.g., refractory cytopenia with multilineage dysplasia and ring sideroblasts and animals with pathological changes not restricted to red cells such as prominent white cell precursor and platelet precursor (megakaryocyte) dysplasia), refractory anemias with excess blasts I and II, 5q-syndrome, megakaryocyte dysplasia with fibrosis, and refractory cytopenia of childhood. In some embodiments, MDS that can be treated include, but are not limited to, MDS that is inherited, MDS with an increased risk of occurrence due to an inherited predisposition, MDS with an increased risk of occurrence due to other blood disorders, MDS with an increased risk of occurrence due to chemical exposure, MDS with an increased risk of occurrence due to ionizing radiation, MDS with an increased risk of occurrence due to cancer treatment (e.g., a combination of radiation and the radiomimetic alkylating agents such as busulfan, nitrosourea, or procarbazine (with a latent period of 5 to 7 years) or DNA topoisomerase inhibitors), MDS evolving from acquired aplastic anemia following immunosuppressive treatment and Fanconi's anemia, MDS with an increased risk due to an mutation in splicing factors, MDS with an increased risk due to a mutation in isocitrate dehydrogenase 1, and MDS with an increased risk due to a mutation in isocitrate dehydrogenase 2. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or MDS, or by having a low blood cell count).

In some embodiments, MDS that can be treated in an animal (e.g., mammals, porcine, canine, avian (e.g., chicken), bovine, feline, primates, rodents, monkeys, rabbits, mice, rats, and humans) using a compound of the invention (e.g., Formula (I)) include, but are not limited to MDS that can be treated by inhibiting one or more of FLT3 (e.g., using FLT3 inhibitors), mutations of FLT3 (e.g., using inhibitors of FLT3 mutants), IRAK4 (e.g., using IRAK4 inhibitors), mutations of IRAK4 (e.g., using inhibitors of IRAK4 mutants), IRAK1 (e.g., using IRAK 1 inhibitors), or mutations of IRAK1 (e.g., using inhibitors of IRAK1 mutant). In certain embodiments, MDS that can be treated include, but are not limited to MDS that can be treated by inhibiting IRAK4 (or its mutations), MDS that can be treated by inhibiting and IRAK1 (or its mutations), or MDS that can be treated by inhibiting IRAK4 (or its mutations) and IRAK1 (or its mutations).

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I)) include, but are not limited to cancers of the myeloid line of blood cells, cancerous tumors (e.g., chloroma which can be found on any tissue or organ outside the bone marrow, such but not limited to skin, gums, lymph nodes, small intestine, mediastinum, lungs, epidural sites, uterus, ovaries, and the orbits of the eyes), cancers that are inherited, cancers with an increased risk of occurrence due to an inherited predisposition (e.g., Down syndrome), cancers with an increased risk of occurrence due to other blood disorders, cancers with an increased risk of occurrence due to chemical exposure (e.g., anti-cancer therapies or occupational chemical exposure), cancers with an increased risk of occurrence due to ionizing radiation (e.g., anti-cancer therapies), cancers evolving from myelodysplastic syndromes, cancers evolving from myeloproliferative disease, and cancers of the B cells.

In some embodiments, cancers that can be treated include, but are not limited to, acute myeloid leukemia (AML), lymphoma, leukemia, bone marrow cancer, non-Hodgkin lymphoma (e.g., diffuse large B-cell lymphoma), Waldenstrom's macroglobulinemia, glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, chronic lymphocytic leukemia (CLL), acute lymphoblastic leukemia, rhabdomyosarcoma, meningioma, gastric cancer, Glioma, oral cancer, nasopharyngeal carcinoma, rectal cancer, stomach cancer, and uterine cancer. In some embodiments, cancers that can be treated include, but are not limited to, acute myeloid leukemia, lymphoma, leukemia, bone marrow cancer, non-Hodgkin lymphoma (e.g., diffuse large B-cell lymphoma), and Waldenstrom's macroglobulinemia.

In some embodiments, cancers that can be treated include, but are not limited to, acute myeloid leukemia (AML), AML that is inherited, AML with an increased risk of occurrence due to an inherited predisposition, AML with a recurrent genetic abnormality (e.g., with inversions or translocations, such as MLLT3/MLL which is a translocation between chromosome 9 and 11 ("MLL")), AML with an increased risk of occurrence due to other blood disorders, AML with an increased risk of occurrence due to chemical exposure, AML with an increased risk of occurrence due to ionizing radiation, AML evolving from myelodysplastic syndromes, AML evolving from myeloproliferative disease, AML with an increased risk due to an FLT3 mutation, AML with an increased risk due to an FLT3 mutation in the juxamembranal region of FLT3, AML with an increased risk due to an FLT3 mutation of an internal tandem duplication in the juxamembranal region of FLT3, AML with an increased risk due to an FLT3 mutation in the kinase domain of FLT3, AML with an increased risk due to the FLT3 mutation D835Y, AML with an increased risk due to the FLT3 mutation D835V, AML with an increased risk due to the FLT3 mutation F691L, and AML with an increased risk due to the FLT3 mutation R834Q. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I)) include, but are not limited to cancers that can be treated by inhibiting (e.g., reducing the activity or expression of) one or more of FLT3 (e.g., using FLT3 inhibitors), mutations of FLT3 (e.g., using inhibitors of FLT3 mutants), IRAK4 (e.g., using IRAK4 inhibitors), mutations of IRAK4 (e.g., using inhibitors of IRAK4 mutants), IRAK1 (e.g., using IRAK 1 inhibitors), or mutations of IRAK1 (e.g., using inhibitors of IRAK1 mutants). In certain embodiments, cancers that can be treated include, but are not limited to cancers that can be treated by inhibiting (e.g., reducing the activity or expression of) FLT3 (or its mutations) and IRAK4 (or its mutations), cancers that can be treated by inhibiting (e.g., reducing the activity or expression of) FLT3 (or its mutations) and IRAK1 (or its mutations), or cancers that can be treated by inhibiting (e.g., reducing the activity or expression of) FLT3 (or its mutations), IRAK4 (or its mutations), and IRAK1 (or its mutations).

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating MDS (e.g., MDS with a splicing factor mutation, MDS with a mutation in isocitrate dehydrogenase 1, or MDS with a mutation in isocitrate dehydrogenase 2), treating can include but is not limited to prophylactic treatment and therapeutic treatment. As such, treatment can include, but is not limited to: preventing MDS (e.g., MDS with a splicing factor mutation, MDS with a mutation in isocitrate dehydrogenase 1, or MDS with a mutation in isocitrate dehydrogenase 2); reducing the risk of MDS (e.g., MDS with a splicing factor mutation, MDS with a mutation in isocitrate dehydrogenase 1, or MDS with a mutation in isocitrate dehydrogenase 2); ameliorating or relieving symptoms of MDS (e.g., MDS with a splicing factor mutation, MDS with a mutation in isocitrate dehydrogenase 1, or MDS with a mutation in isocitrate dehydrogenase 2); eliciting a bodily response against MDS (e.g., MDS with a splicing factor mutation, MDS with a mutation in isocitrate dehydrogenase 1, or MDS with a mutation in isocitrate dehydrogenase 2); inhibiting the development or progression of MDS (e.g., MDS with a splicing factor mutation, MDS with a mutation in isocitrate dehydrogenase 1, or MDS with a mutation in isocitrate dehydrogenase 2); inhibiting or preventing the onset of symptoms associated with MDS (e.g., MDS with a splicing factor mutation, MDS with a mutation in isocitrate dehydrogenase 1, or MDS with a mutation in isocitrate dehydrogenase 2); reducing the severity of MDS (e.g., MDS with a splicing factor mutation, MDS with a mutation in isocitrate dehydrogenase 1, or MDS with a mutation in isocitrate dehydrogenase 2); causing a regression of MDS (e.g., MDS with a splicing factor mutation, MDS with a mutation in isocitrate dehydrogenase 1, or MDS with a mutation in isocitrate dehydrogenase 2) or one or more of the symptoms associated with MDS (e.g., an increase in blood cell count); causing remission of MDS (e.g., MDS with a splicing factor mutation, MDS with a mutation in isocitrate dehydrogenase 1, or MDS with a mutation in isocitrate dehydrogenase 2); causing remission of MDS (e.g., MDS with a splicing factor mutation, MDS with a mutation in isocitrate dehydrogenase 1, or MDS with a mutation in isocitrate dehydrogenase 2) by preventing or minimizing FLT3 mutations (e.g., internal tandem duplication mutations or the D835Y mutation); preventing relapse of MDS (e.g., MDS with a splicing factor mutation, MDS with a mutation in isocitrate dehydrogenase 1, or MDS with a mutation in isocitrate dehydrogenase 2); or preventing relapse of MDS (e.g., MDS with a splicing factor mutation, MDS with a mutation in isocitrate dehydrogenase 1, or MDS with a mutation in isocitrate dehydrogenase 2) in animals that have intrinsic or acquired resistance to other MDS treatments. In some embodiments, treating does not include prophylactic treatment of MDS (e.g., preventing or ameliorating future MDS).

As related to treating cancer (e.g., acute myeloid leukemia, lymphoma, leukemia, bone marrow cancer, non-Hodgkin lymphoma, or Waldenstrom's macroglobulinemia), treating can include but is not limited to prophylactic treatment and therapeutic treatment. As such, treatment can include, but is not limited to: preventing cancer (e.g., acute myeloid leukemia, lymphoma, leukemia, bone marrow cancer, non-Hodgkin lymphoma, or Waldenstrom's macroglobulinemia); reducing the risk of cancer (e.g., acute myeloid leukemia, lymphoma, leukemia, bone marrow cancer, non-Hodgkin lymphoma, or Waldenstrom's macroglobulinemia); ameliorating or relieving symptoms of cancer (e.g., acute myeloid leukemia, lymphoma, leukemia, bone marrow cancer, non-Hodgkin lymphoma, or Waldenstrom's macroglobulinemia); eliciting a bodily response against cancer (e.g., acute myeloid leukemia, lymphoma, leukemia, bone marrow cancer, non-Hodgkin lymphoma, or Waldenstrom's macroglobulinemia); inhibiting the development or progression of cancer (e.g., acute myeloid leukemia, lymphoma, leukemia, bone marrow cancer, non-Hodgkin lymphoma, or Waldenstrom's macroglobulinemia); inhibiting or preventing the onset of symptoms associated with cancer (e.g., acute myeloid leukemia, lymphoma, leukemia, bone marrow cancer, non-Hodgkin lymphoma, or Waldenstrom's macroglobulinemia); reducing the severity of cancer (e.g., acute myeloid leukemia, lymphoma, leukemia, bone marrow cancer, non-Hodgkin lymphoma, or Waldenstrom's macroglobulinemia); causing a regression of cancer (e.g., acute myeloid leukemia, lymphoma, leukemia, bone marrow cancer, non-Hodgkin lymphoma, or Waldenstrom's macroglobulinemia) or one or more of the symptoms associated with cancer (e.g., a decrease in tumor size); causing remission of cancer (e.g., acute myeloid leukemia, lymphoma, leukemia, bone marrow cancer, non-Hodgkin lymphoma, or Waldenstrom's macroglobulinemia); causing remission of cancer (e.g., acute myeloid leukemia, lymphoma, leukemia, bone marrow cancer, non-Hodgkin lymphoma, or Waldenstrom's macroglobulinemia) by preventing or minimizing FLT3 mutations (e.g., internal tandem duplication mutations or the D835Y mutation); causing remission of acute myeloid leukemia by preventing or minimizing FLT3 mutations (e.g., internal tandem duplication mutations or the D835Y mutation); preventing relapse of cancer (e.g., acute myeloid leukemia, lymphoma, leukemia, bone marrow cancer, non-Hodgkin lymphoma, or Waldenstrom's macroglobulinemia); preventing relapse of cancer (e.g., acute myeloid leukemia, lymphoma, leukemia, bone marrow cancer, non-Hodgkin lymphoma, or Waldenstrom's macroglobulinemia) in animals that have intrinsic or acquired resistance to other cancer treatments (e.g., from some FLT3 inhibitors or from MLL); or preventing relapse of acute myeloid leukemia in animals that have intrinsic or acquired resistance to other cancer treatments (e.g., from some FLT3 inhibitors or from MLL). In some embodiments, treating does not include prophylactic treatment of cancer (e.g., preventing or ameliorating future cancer).

Treatment of an animal can occur using any suitable administration method (such as those disclosed herein) and using any suitable amount of a compound of the invention (e.g., Formula (I)). In some embodiments, methods of treatment comprise treating an animal for MDS (e.g., MDS with a splicing factor mutation, MDS with a mutation in isocitrate dehydrogenase 1, or MDS with a mutation in isocitrate dehydrogenase 2). In some embodiments, methods of treatment comprise treating an animal for cancer (e.g., acute myeloid leukemia, lymphoma, leukemia, bone marrow cancer, non-Hodgkin lymphoma, or Waldenstrom's macroglobulinemia). Other embodiments include treatment after one or more of having a blood disorder, having myelodysplastic syndrome, having myeloproliferative disease, an occurrence of chemical exposure, an exposure to ionizing radiation, or a treatment for cancer (e.g., with chemotherapy, ionizing radiation, or both). Some embodiments of the invention include a method for treating a subject (e.g., an animal such as a human or primate) with a composition comprising a compound of the invention (e.g., Formula (I)) (e.g., a pharmaceutical composition) which comprises one or more administrations of one or more such compositions; the compositions may be the same or different if there is more than one administration.

In some embodiments, the method of treatment includes administering an effective amount of a composition comprising a compound of the invention (e.g., Formula (I)). As used herein, the term "effective amount" refers to a dosage or a series of dosages sufficient to affect treatment (e.g., to treat MDS such as but not limited to MDS (e.g., MDS with a splicing factor mutation, MDS with a mutation in isocitrate dehydrogenase 1, or MDS with a mutation in isocitrate dehydrogenase 2); or to treat cancer, such as but not limited to acute myeloid leukemia, lymphoma, leukemia, bone marrow cancer, non-Hodgkin lymphoma, or Waldenstrom's macroglobulinemia) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of the invention (e.g., Formula (I) such as but not limited to compounds I-2, I-15, I-20, I-22, I-24, I-26, I-27, I-42, I-53, or I-54) (which can be administered to an animal such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg human body weight or about 6.5 mg/kg human body weight. In some instances, an effective amount of at least one compound of the invention (e.g., Formula (I) such as but not limited to compounds I-2, I-15, I-20, I-22, I-24, I-26, I-27, I-42, I-53, or I-54) (which can be administered to an animal such as mammals, rodents, mice, rabbits, feline, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of at least one compound of the invention (e.g., Formula (I) such as but not limited to compounds I-2, I-15, I-20, I-22, I-24, I-26, I-27, I-42, I-53, or I-54) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 20 mg/kg human body weight or about 100 mg/kg human body weight. In some instances, an effective amount of at least one compound of the invention (e.g., Formula (I) such as but not limited to compounds I-2, I-15, I-20, I-22, I-24, I-26, I-27, I-42, I-53, or I-54) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., decreasing tumor size or increasing blood cell count). A therapeutically effective amount can be administered in one or more administrations. For some purposes of this invention, a therapeutically effective amount is an amount appropriate to treat an indication (e.g., to treat cancer, ADL, or MDS). By treating an indication is meant achieving any desirable effect, such as one or more of palliate, ameliorate, stabilize, reverse, slow, or delay disease (e.g., cancer, ADL, or MDS) progression, increase the quality of life, or to prolong life. Such achievement can be measured by any suitable method, such as but not limited to measurement of tumor size or blood cell count.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the administration of at least one compound of the invention (e.g., Formula (I)) is an adjuvant cancer therapy or part of an adjuvant cancer therapy. Adjuvant treatments include treatments by the mechanisms disclosed herein and of cancers as disclosed herein, including, but not limited to tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In still other embodiments, a compound of the invention (e.g., Formula (I)) can be used as adjuvant with other chemotherapeutic agents. The use of a compound of the invention (e.g., Formula (I)) may, in some instances, reduce the duration of the dose of both drugs and drug combinations reducing the side effects.

In some embodiments, the treatments disclosed herein can include use of other drugs (e.g., antibiotics) or therapies for treating disease. For example, antibiotics can be used to treat infections and can be combined with a compound of the invention to treat disease (e.g., infections). In other embodiments, intravenous immunoglobulin (IVIG) therapy can be used as part of the treatment regime (i.e., in addition to administration of the compound(s) of the invention).

Methods for Preparing Compounds of Formula (I)

Some embodiments of the present invention include methods for the preparation of compounds of Formula (I). In certain embodiments, a compound of Formula (I) can be prepared comprising the step of reacting a compound of Formula (II) with a compound of Formula (III) to result in Formula (IV), which is later made into Formula (I) (e.g., using one or more synthetic steps).

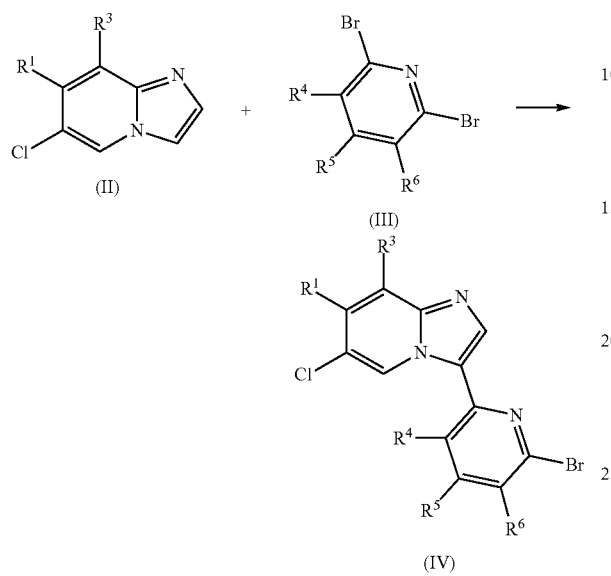

$R^1$ and $R^3$ of Formula (II) are the same as that defined in Formula (I). Formula (II) can be prepared using any suitable method or can be purchase where available (e.g., from Aldrich). $R^4$, $R^5$, and $R^6$ of Formula (III) are the same as that defined in Formula (I). Formula (III) can be prepared using any suitable method or can be purchase where available (e.g., from Aldrich). $R^1$, $R^3$, $R^4$, $R^5$, and $R^6$ of Formula (IV) are the same as that defined in Formula (I). In certain embodiments, the reaction of Formula (II) with Formula (III) can be performed using direct arylation through C—H bond activation. In some embodiments, the reaction can be carried out under an atmosphere of dry nitrogen in dried glassware. In other embodiments, solvents used are of anhydrous quality (e.g., purchased from Aldrich Chemical Co.) and/or can be used as received.

In some embodiments, Formula (II) can be reacted with Formula (III) under the following conditions: Formula (II) and Formula (III) are in a mixture comprising triphenylphosphine, diacetoxypalladium, potassium carbonate, ethanol, and 1,4-dioxane, and is heated (e.g., with a microwave) at a certain temperature (e.g., at about 130° C.) for a certain amount of time (e.g., about 1 hour).

In certain embodiments, a microwave vial can be equipped with a magnetic stir bar and can be charged with Formula (II) (e.g., about 46 mg or about 0.25 mmol), Formula (III) (e.g., about 89 mg or about 0.38 mmol), diacetoxypalladium (e.g., about 3 mg or about 0.01 mmol), potassium carbonate (e.g., about 69 mg or about 0.50 mmol), and triphenylphosphine (e.g., about 7 mg or about 0.025 mmol). To this 1,4-dioxane (e.g., about 0.4 mL) and ethanol (e.g., about 0.2 mL) can be added, in some instances. The mixture can then be subjected to heating (e.g., microwave irradiation), such as, for example, from about 90° C. to about 180° C. (e.g., about 130° C.) for from about 30 minutes to about 1.5 hours (e.g., about 1 h). The mixture can then be diluted with, for example, dichloromethane (DCM) (e.g., about 10 mL) and $H_2O$ (e.g. about 10 mL). The layers can then be separated and the aqueous layer extracted with, for example, (3×10 mL) DCM. The organic extracts can be combined and can then be washed (e.g., with brine (1×10 mL)), dried (e.g., over sodium sulfate), filtered and concentrated (e.g., in vacuo). The product can then be purified (e.g., via ISCO chromatography (0-5% methanol/DCM)).

In some embodiments, where $R^1$ is alkoxy (e.g., methoxy) in Formula (IV), a morpholino-alkoxy (e.g., morpholino-ethoxy) can be substituted for the alkoxy (e.g., methoxy) as a step to preparing Formula (I). This can occur in two steps: (a) by converting the alkoxy to —OH and (b) by converting the —OH to the morpholino-alkoxy. The synthesis below is exemplary for methoxy-to-morphilinoethoxy, but can be used to convert any alkoxy-to-morpholinoalkoxy, where that starting alkoxy can be the same or different as the alkoxy in the morpholinoalkoxy.

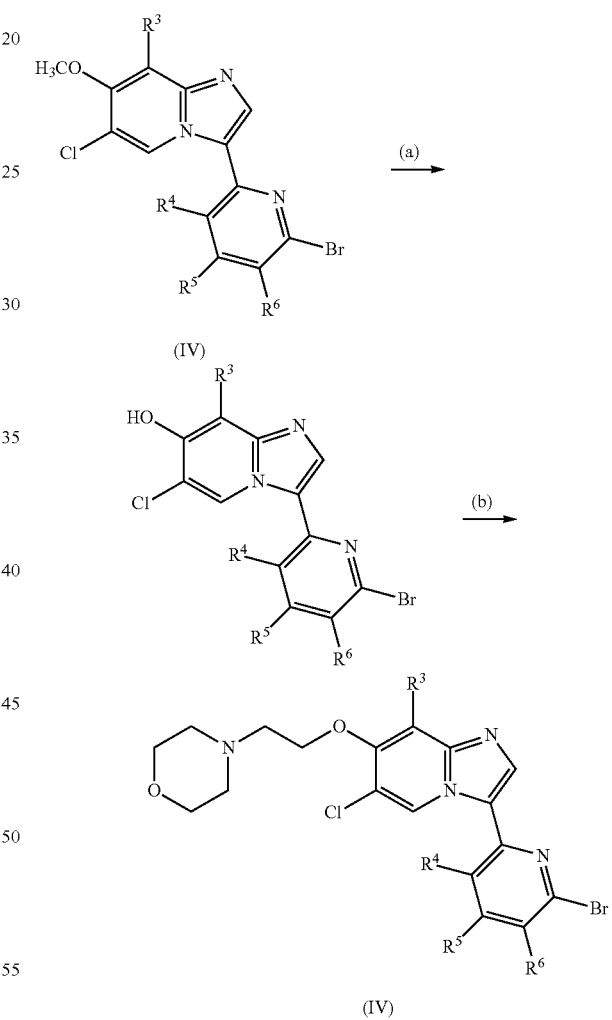

$R^3$, $R^4$, $R^5$, and $R^6$ of Formula (IV) are the same as that defined in Formula (I). In some embodiments, the reaction can be carried out under an atmosphere of dry nitrogen in dried glassware. In other embodiments, solvents used are of anhydrous quality (e.g., purchased from Aldrich Chemical Co.) and/or can be used as received.

For step (a), in some embodiments, Formula (IV) (e.g., with $R^1$ as a $C_1$-$C_6$ alkoxy) can be reacted under the following conditions: Formula (IV) (e.g., with $R^1$ as a $C_1$-$C_6$ alkoxy) is in a mixture comprising 4-methylbenzenesulfonic acid hydrate, lithium chloride, and DMF, and can be then heated (e.g., with a microwave) at a certain temperature (e.g., about 120° C.) for a certain amount of time (e.g., for about 2 h).

In other embodiments for step (a), a microwave vial equipped with a stir bar can be charged with Formula (IV) (e.g., with $R^1$ as a $C_1$-$C_6$ alkoxy) (e.g., about 85 mg or about 0.25 mmol), 4-methylbenzenesulfonic acid hydrate (e.g., about 239 mg or about 1.3 mmol) and lithium chloride (e.g., about 53 mg or about 1.3 mmol). DMF (e.g., about 1.3 mL) can then be added and the vial can be subjected to microwave irradiation at from about 90° C. to about 150° C. (e.g., about 120° C.) for from about 1 h to about 3 h (e.g., about 2 h). In some instances, the resulting product can be purified (e.g., by reverse phase ISCO chromatography (1-100% acetonitrile/$H_2O$)).

In some embodiments for step (b), the product of step (a) can be reacted under the following conditions: the product of step (a) can be in a mixture comprising di-tert-butyl azodicarboxylate, morpholinoalkanol (e.g., 2-morpholinoethanol), THF, and triphenylphosphine, and can be then heated (e.g., with a microwave) or cooled at a certain temperature (e.g., from about 20° C. to about 30° C.) or can be room temperature (about 25° C.) for a certain amount of time (e.g., about 1.5 h).

In some embodiments for step (b), a 25 mL round bottomed flask, equipped with a stir bar, can be charged with the product of step (a) (e.g., about 70 mg or about 0.22 mmol), di-tert-butyl azodicarboxylate (e.g., about 89 mg or about 0.39 mmol), morpholinoalkanol (e.g., 2-morpholinoethanol) (e.g., about 51 mg or about 0.39 mmol), THF (e.g., from about 2 mL to about 50 mL or from about 10 mL to about 15 mL), and triphenylphosphine (e.g., about 102 mg or about 0.39 mmol). The reaction mixture can be stirred at from about 20° C. to about 30° C. (e.g., room temperature or about 25° C.) for from about 1 h to about 2 h (e.g., about 1.5 h). The THF can then be removed (e.g., in vacuo) and the resulting product can then be purified (e.g., by ISCO chromatography (1-10% methanol/DCM)) to provide Formula (IV) with an alkoxy-morpholino (e.g., ethoxy-morpholino).

In certain embodiments, a compound of Formula (I) can be prepared comprising the step of reacting a compound of Formula (IV) with a compound of Formula (V) to result in Formula (VI), which is later made into Formula (I) (e.g., using one or more synthetic steps).

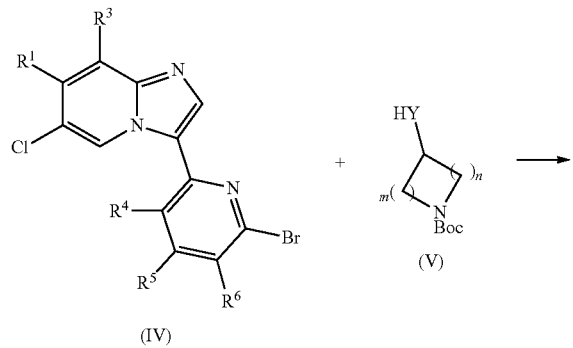

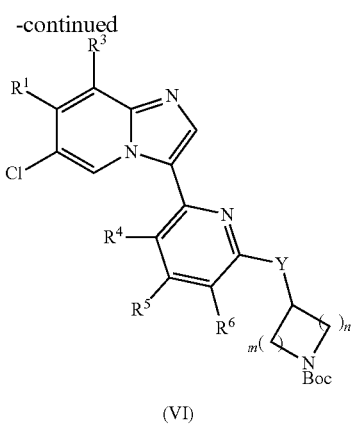

$R^1$, $R^3$, $R^4$, $R^5$, and $R^6$ of Formula (IV) are the same as that defined in Formula (I). Formula (IV) can be prepared using any suitable method (e.g., see above) or can be purchase where available. Y (e.g., Y is not 0), n, and m of Formula (V) are the same as that defined in Formula (I). Formula (V) can be prepared using any suitable method or can be purchase where available (e.g., from Aldrich). $R^1$, $R^3$, $R^4$, $R^5$, $R^6$, Y (e.g., Y is not 0), n, and m of Formula (VI) are the same as that defined in Formula (I). In certain embodiments, the reaction of Formula (IV) with Formula (V) can be performed via $S_NAr$ displacement, such as, for example, by a Buchwald-Hartwig amination. In some embodiments, the reaction can be carried out under an atmosphere of dry nitrogen in dried glassware. In other embodiments, solvents used are of anhydrous quality (e.g., purchased from Aldrich Chemical Co.) and/or can be used as received.

In some embodiments, Formula (IV) can be reacted with Formula (V) under the following conditions: Formula (IV) and Formula (V) are in a mixture comprising 2-dicyclohexylphosphino-2',4',6'-triisopropylbiphenyl (XPhos), diacetoxypalladium, potassium carbonate, and t-butanol, and heated (e.g., with a microwave) at a certain temperature (e.g., at about 110° C.) for a certain amount of time (e.g., about 3 h).

In other embodiments, Formula (IV) (e.g., about 40 mg or about 0.12 mmol) in tert-butanol (e.g., about 1 mL) in a flame dried microwave vial equipped with a magnetic stir bar can be added to tert-butyl 3-aminopyrrolidine-1-carboxylate (e.g., about 51 mg or about 0.27 mmol), diacetoxypalladium (e.g., about 5 mg or about 0.02 mmol), 2-dicyclohexylphosphino-2',4',6'-triisopropylbiphenyl (e.g., about 28 mg or about 0.06 mmol) and potassium carbonate (e.g., about 57 mg or about 0.41 mmol). The mixture can then be purged with nitrogen, sealed and subjected to microwave irradiation at, for example, from about 80° C. to about 140° C. (e.g., about 110° C.) for from about 1 h to about 5 h (e.g., about 3 h). The mixture can then, in some instances, be diluted with DCM (e.g., about 10 mL) and $H_2O$ (e.g., about 10 mL). The layers can be separated and the aqueous layer can be extracted (e.g., with (e.g., 3×10 mL) DCM). The organic extracts can be combined and washed (e.g., with brine (1×10 mL)), dried (e.g., over sodium sulfate), filtered and concentrated (e.g., in vacuo). In some instances, further purification can be accomplished, for example via ISCO chromatography (0-3% methanol/DCM).

When Y is O, in some embodiments, a compound of Formula (I) can be prepared comprising the step of reacting a compound of Formula (IV) with a compound of Formula (V) to result in Formula (VI), which is later made into Formula (I) (e.g., using one or more synthetic steps).

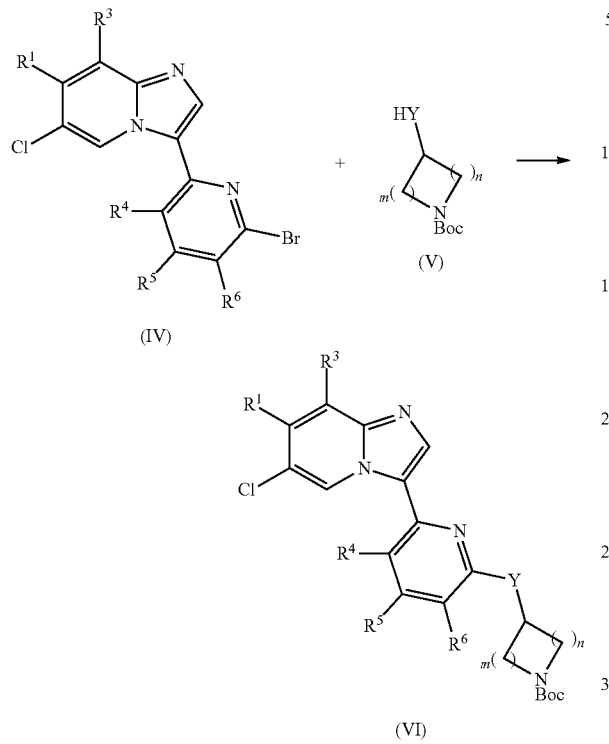

R$^1$, R$^3$, R$^4$, R$^5$, and R$^6$ of Formula (IV) are the same as that defined in Formula (I). Formula (IV) can be prepared using any suitable method (e.g., see above) or can be purchase where available. For Formula (V), n and m are the same as that defined in Formula (I); Y is O in Formula (V). Formula (V) can be prepared using any suitable method or can be purchase where available (e.g., from Aldrich). R$^1$, R$^3$, R$^4$, R$^5$, R$^6$, n, and m of Formula (VI) are the same as that defined in Formula (I); Y is O. In certain embodiments, the reaction can be carried out under an atmosphere of dry nitrogen in dried glassware. In other embodiments, solvents used are of anhydrous quality (e.g., purchased from Aldrich Chemical Co.) and/or can be used as received.

In some embodiments, Formula (IV) is reacted with Formula (V) under the following conditions: Formula (IV) and Formula (V) are in a mixture comprising copper(I) iodide, cesium carbonate, 3,4,7,8-tetramethyl-1,10-phenanthroline, and toluene, and sonicated, and then heated (e.g., with a microwave) at a certain temperature (e.g., at about 120° C.) for a certain amount of time (e.g., about 3 h).

In other embodiments, an oven dried microwave vial can be charged with Formula (IV) (e.g., about 100 mg or about 0.30 mmol), Formula (V) (e.g., about 332 mg or about 1.77 mmol), copper(I) iodide (e.g., about 14 mg or about 0.07 mmol), cesium carbonate (e.g., about 722 mg or about 2.22 mmol) and 3,4,7,8-tetramethyl-1,10-phenanthroline (e.g., about 35 mg or about 0.15 mmol). Toluene (e.g., about 0.83 mL) can be added and the vial purged with nitrogen. The vial can then be sonicated before subjecting to heating (e.g., microwave irradiation) at from about 90° C. to about 150° C. (e.g., about 120° C.) for from about 1 h to about 5 h (e.g., about 3 h). The mixture can then be diluted with DCM (e.g., about 20 mL) and H$_2$O (e.g., about 20 mL). The layers can then be separated and the aqueous layer extracted (e.g., with (3×20 mL) DCM). The organic extracts can be combined and washed (e.g., with brine (1×20 mL)), dried (e.g., over sodium sulfate), filtered and concentrated (e.g., in vacuo). The residue can then be purified (e.g., via ISCO chromatography (70-100% EtOAc/hexanes)).

In certain embodiments, a compound of Formula (I) can be prepared comprising the step of reacting a compound of Formula (VI) with a compound of Formula (VII) to result in Formula (VIII), which is later made into Formula (I) (e.g., using one or more synthetic steps).

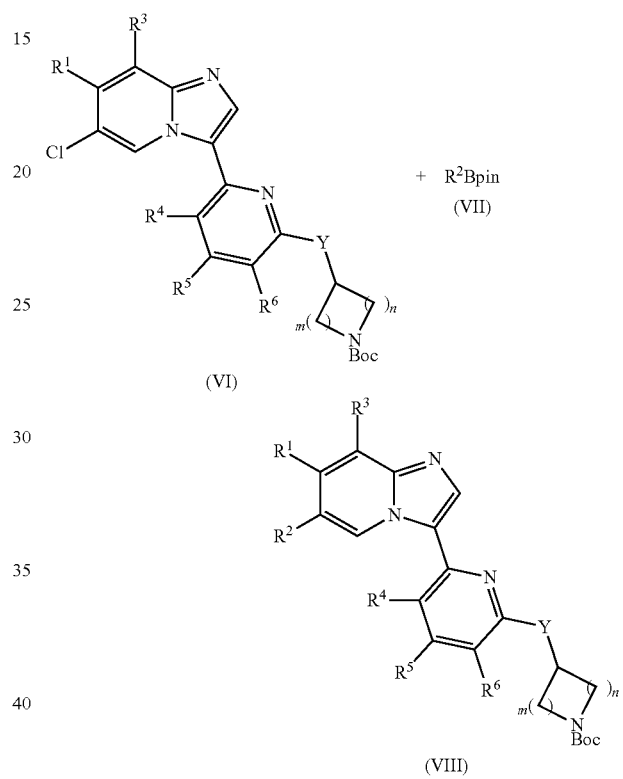

R$^1$, R$^3$, R$^4$, R$^5$, R$^6$, Y, n, and m of Formula (VI) are the same as that defined in Formula (I). Formula (VI) can be prepared using any suitable method (e.g., see above) or can be purchase where available. R$^2$ of Formula (VII) is the same as that defined in Formula (I), and in some instances R$^2$ can have a group protected (e.g., via Boc) during the reaction step. Formula (VII) can be prepared using any suitable method or can be purchase where available (e.g., from Aldrich). R$^1$, R$^2$, R$^3$, R$^4$, R$^5$, R$^6$, Y, n, and m of Formula (VIII) are the same as that defined in Formula (I). In certain embodiments, the reaction of Formula (VI) with Formula (VII) can be performed via a Suzuki-Miyaura coupling strategy (e.g., for heterocyclic boronic derivatives). In some embodiments, the reaction can be carried out under an atmosphere of dry nitrogen in dried glassware. In other embodiments, solvents used are of anhydrous quality (e.g., purchased from Aldrich Chemical Co.) and/or can be used as received.

In some embodiments, Formula (VI) can be reacted with Formula (VII) under the following conditions: Formula (VI) and Formula (VII) (e.g., with or without a group on R$^2$ being protected, such as with a Boc) are in a mixture comprising tricyclohexylphosphine (PCy$_3$), tris(dibenzylideneacetone)

dipalladium(0) (Pd$_2$(dba)$_3$), potassium carbonate, water and 1,4 dioxane, and heated (e.g., with a microwave) at a certain temperature (e.g., at about 110° C.) for a certain amount of time (e.g., about 3 h).

In other embodiments, to an oven dried microwave vial equipped with a stir bar can be added Formula (VI) (e.g., about 150 mg or about 0.34 mmol), Formula (VII) (e.g., 4,4,5,5-tetramethyl-1,3,2-dioxaborolan-2-yl)-R$_2$ or 4,4,5,5-tetramethyl-1,3,2-dioxaborolan-2-yl)-R$_2$ with a group on R$_2$ protected, such as with Boc) (e.g., about 298 mg or about 1.01 mmol), tricyclohexylphosphine (e.g., about 131 μL or about 0.08 mmol, about 20 wt. % in toluene), tris(dibenzylideneacetone)dipalladium(0) (e.g., about 31 mg or about 0.034 mmol) and aqueous potassium phosphate (e.g., about 0.7 mL of about 1.3 M). 1,4-dioxane (e.g., about 2.5 mL) can then added and the microwave vial can be purged with nitrogen and sealed. The mixture can then be subjected to heat (e.g., microwave irradiation) at, for example, from about 80° C. to about 140° C. (e.g., about 110° C.) for from about 1 h to about 5 h (e.g., about 3 h). The mixture can then be diluted with ethyl acetate (EtOAc) (e.g., about 20 mL) and H$_2$O (e.g., about 20 mL). The layers can then be separated and the aqueous layer can be extracted (e.g., 3×20 mL) with, for example, EtOAc. The organic extracts can then be combined and washed, for example with brine (e.g., 1×20 mL), dried (e.g., over sodium sulfate), filtered, and concentrated (e.g., in vacuo). The product can then be purified (e.g., via ISCO chromatography (e.g., 0-10% methanol/DCM)).

In some embodiments, a compound of Formula (I) can be prepared comprising the step of reacting a compound of Formula (VIII) to result in Formula (I).

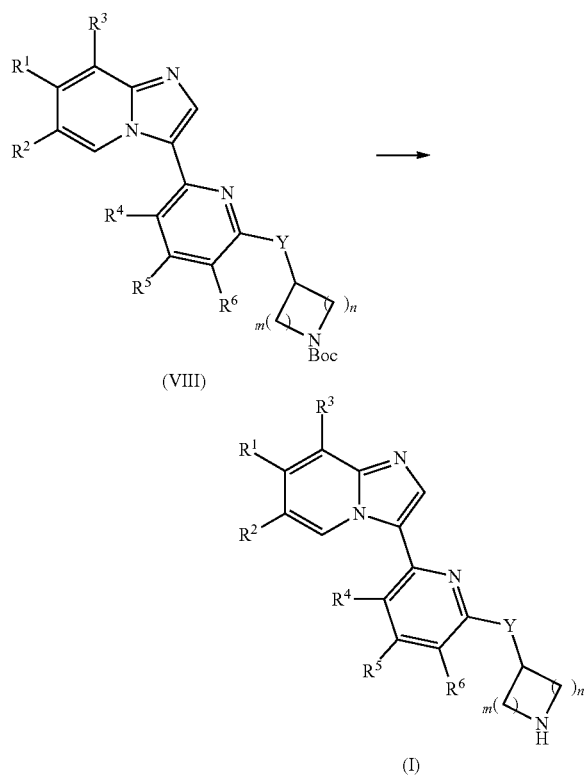

R$^1$, R$^2$, R$^3$, R$^4$, R$^5$, R$^6$, Y, n, and m of Formula (VIII) are the same as that defined in Formula (I). In certain embodiments, the reaction of Formula (VIII) can be performed via a deprotection strategy (e.g., for removing one or more protecting groups, such as one or more Boc protecting groups or one or more of a combination of different protecting groups). In some embodiments, the reaction can be carried out under an atmosphere of dry nitrogen in dried glassware. In other embodiments, solvents used are of anhydrous quality (e.g., purchased from Aldrich Chemical Co.) and/or can be used as received.

In some embodiments, Formula (VIII) can be reacted under the following conditions: Formula (VIII) is in a mixture comprising trifluoroacetic acid (TFA) and dichloromethane (DCM), and is optionally heated (e.g., with a microwave) or cooled at a certain temperature (e.g., from about 20° C. to about 30° C.) or can be at room temperature (e.g., about 25° C.). The product can then be purified (e.g., via ISCO chromatography (50-100% EtOAc/hexanes)).

In some embodiments, when R$^2$ is a halogen (e.g., Cl) in Formula (I), R$^2$ can be altered to a C$_2$-C$_7$ alkynyl (e.g., ethynyl or a C$_2$-C$_7$ alkynyl where a triple bond is at an end-carbon position (e.g., a 1-alkynyl)). For example, an oven dried microwave vial can be charged with Formula (I) (e.g., about 30 mg or about 0.068 mmol), tert-butyl(ethynyl)dimethylsilane (e.g., about 0.03 mL or about 0.17 mmol), tri-tert-butylphosphine (e.g., about 0.135 mL or about 0.14 mmol, about 1 M solution in toluene), 1,8-diazabicyclo[5.4.0]undec-7-ene (e.g., about 2 μL or about 0.014 mmol), cesium carbonate (e.g., about 44 mg or about 0.14 mmol) and dichlorobis(triphenylphosphine)palladium(II) (e.g., about 5 mg or about 0.007 mmol). DMF (e.g., about 0.5 mL) can then be added and the microwave vial can be purged with nitrogen and sealed. The mixture can then be subjected to heat (e.g., microwave irradiation) at, for example, from about 100° C. to about 200° C. (e.g., about 150° C.) for from about 0.5 h to about 2 h (e.g., about 1 h). The product can then be purified (e.g., via ISCO chromatography (50-100% EtOAc/hexanes)).

In some embodiments, Formula (I) (or any other formula recited above) can be recovered. Recovery can occur using any suitable method including but not limited to HPLC (e.g., reverse phase), LC, precipitation, centrifugation, column chromatography (e.g., size exclusion chromatography or ion exchange chromatography), use of silica gel, or combinations thereof. In some embodiments, a method for the preparation of a compound of Formula (I) can comprise one or more of the above-mentioned steps. In certain embodiments, a method for preparing a compound of Formula (I) comprises (a) reacting a compound of Formula (II) with a compound of Formula (III) to result in a mixture comprising a compound of Formula (IV);

(b) reacting a compound of Formula (IV) with a compound of Formula (V) to result in a mixture comprising a compound of Formula (VI);

(c) optionally reacting a compound of Formula (VI) with a compound of Formula (VII) to result in a mixture comprising a compound of Formula (VIII);

(d) removing one or more protecting groups from a compound of Formula (VI) or from a compound of Formula (VIII); and (e) recovering Formula (I).

The presently-disclosed subject matter is further illustrated by the following specific but non-limiting examples. The following examples may include compilations of data that are representative of data gathered at various times during the course of development and experimentation related to the present invention.

Examples

Example Set A—Synthetic Methods and Compound Characterization

Synthesis of compound C was performed using direct arylation through C—H bond activation (Scheme 1). With compound C in hand, the $S_NAr$ displacement was accomplished through a Buchwald-Hartwig amination to give compound E and the installation of aryl group at 6-position of imidazo[1,2-a]pyridine ring used a Suzuki-Miyaura coupling strategy for heterocyclic boronic derivatives to give compound F. For compounds not encompassed by this general scheme, preparation procedures and spectral characterizations are further depicted below.

Scheme 1.

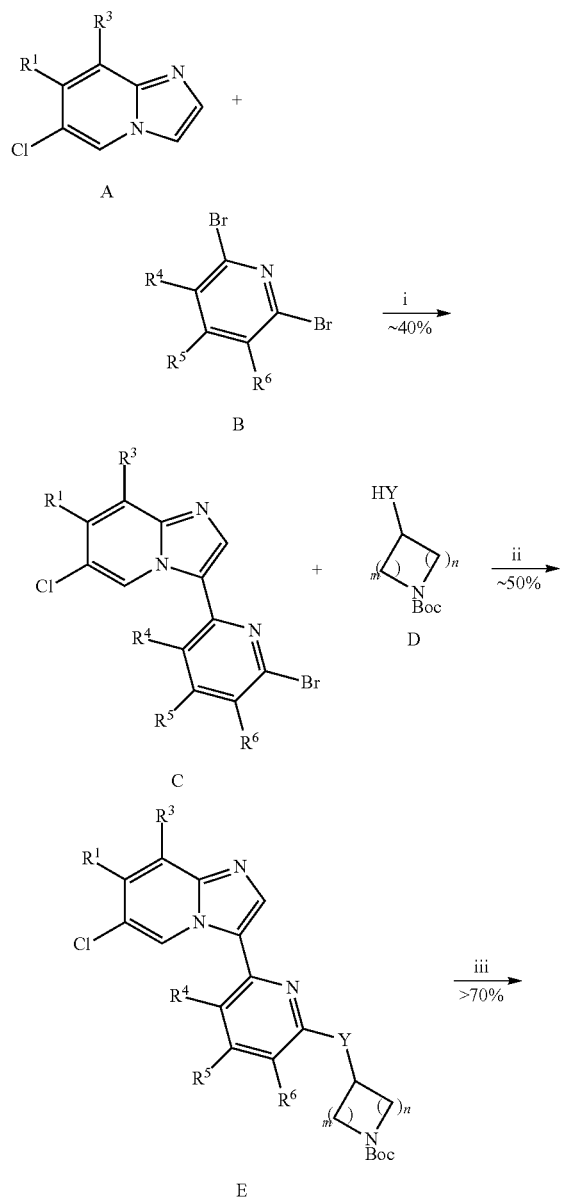

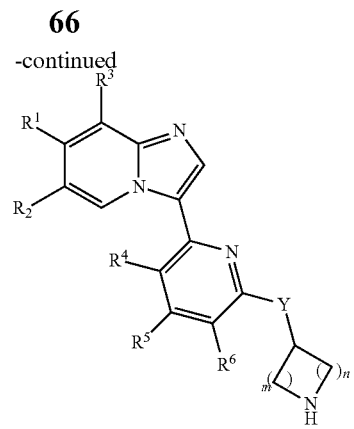

F (i) $PPh_3$, $Pd(OAc)_2$, $K_2CO_3$, EtOH, 1-4-dioxane, MW, 130° C.;
(ii) XPhos, $Pd(OAc)_2$, $K_2CO_3$, $^tBuOH$, MW, 110° C.;
(iii) a. $R^2Bpin$, $PCy_3$, $Pd_2(dba)_3$, $K_3PO_4$, $H_2O$, 1,4-dioxane, MW, 110° C., b. TFA, DCM, rt.

General Methods

Unless otherwise stated, all reactions were carried out under an atmosphere of dry nitrogen in dried glassware. Indicated reaction temperatures refer to those of the reaction bath, while room temperature (rt) is noted as 25° C. All solvents were of anhydrous quality purchased from Aldrich Chemical Co. and used as received. Commercially available starting materials and reagents were purchased from Aldrich and were used as received.

Analytical thin layer chromatography (TLC) was performed with Sigma Aldrich TLC plates (5×20 cm, 60 Å, 250 μm). Visualization was accomplished by irradiation under a 254 nm UV lamp. Chromatography on silica gel was performed using forced flow (liquid) of the indicated solvent system on Biotage KP-Sil pre-packed cartridges and using the Biotage SP-1 automated chromatography system. $^1$HNMR spectra were recorded on a Varian Inova 400 MHz spectrometer. Chemical shifts are reported in ppm with the solvent resonance as the internal standard (DMSO-d6 2.50 ppm for $^1$H). Data are reported as follows: chemical shift, multiplicity (s=singlet, d=doublet, t=triplet, q=quartet, br=broad, m=multiplet), coupling constants, and number of protons. Low resolution mass spectra (electrospray ionization) were acquired on an Agilent Technologies 6130 quadrupole spectrometer coupled to the HPLC system. High resolution mass spectral data was collected using and Agilent 6210 time-of-flight (TOF) mass spectrometer, also coupled to an Agilent Technologies 1200 series HPLC system. If needed, products were purified via a Waters semi-preparative HPLC equipped with a Phenomenex Luna® C18 reverse phase (5 micron, 30×75 mm) column having a flow rate of 45 mL/min. The mobile phase was a mixture of acetonitrile and $H_2O$ each containing 0.1% trifluoroacetic acid. Samples were analyzed for purity on an Agilent 1200 series LC/MS equipped with a Luna® C18 reverse phase (3 micron, 3×75 mm) column having a flow rate of 0.8-1.0 mL/min over a 7-minute gradient and an 8.5 minute run time (Method 1). The mobile phase was a mixture of acetonitrile (0.025% TFA) and $H_2O$ (0.05% TFA), with temperature maintained at 50° C. Purity of final compounds was determined to be >95%, using a 3 μL injection with quantitation by AUC at 220 and 254 nm (Agilent Diode Array Detector).

Method A.

Used for the synthesis of many of the compounds. This procedure is exemplified below for compound I-20.

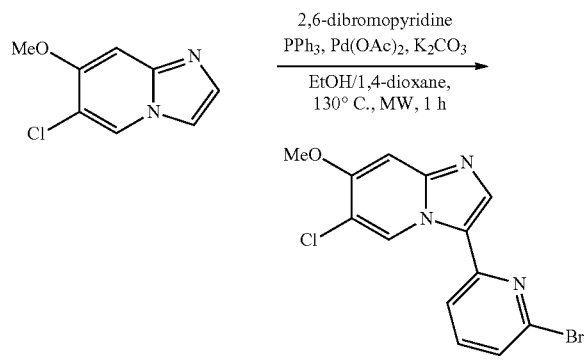

A microwave vial equipped with a magnetic stir bar was charged with 6-chloro-7-methoxyimidazo[1,2-a]pyridine (46 mg, 0.25 mmol), 2,6-dibromopyridine (89 mg, 0.38 mmol), diacetoxypalladium (3 mg, 0.01 mmol), potassium carbonate (69 mg, 0.50 mmol), and triphenylphosphine (7 mg, 0.025 mmol). To this was added 0.4 mL of 1,4-dioxane and 0.2 mL of ethanol. The mixture was subjected to microwave irradiation at 130° C. for 1 h. The mixture was diluted with dichloromethane (DCM) (10 mL) and H$_2$O (10 mL). The layers were separated and the aqueous layer was extracted with (3×10 mL) DCM. The organic extracts were combined and washed with brine (1×10 mL), dried over sodium sulfate, filtered and concentrated in vacuo. The crude residue was then purified via ISCO chromatography (0-5% methanol/DCM) to deliver product (85 mg, 70%) as an off-white solid.

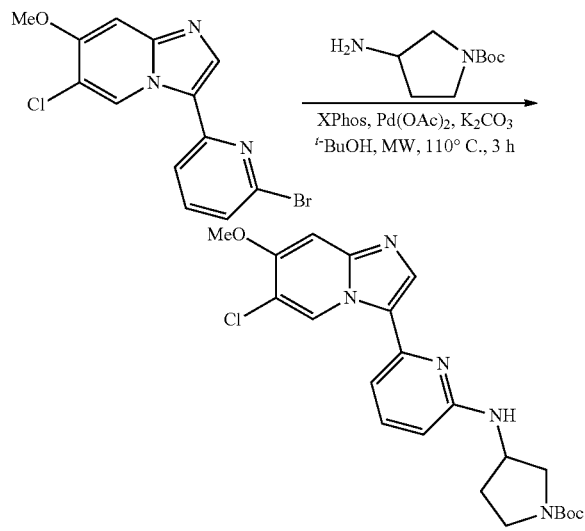

To a suspension of 3-(6-bromopyridin-2-yl)-6-chloro-7-methoxyimidazo[1,2-a]pyridine (40 mg, 0.12 mmol) in tert-butanol (1 mL) in a flame dried microwave vial equipped with a magnetic stir bar was added tert-butyl 3-aminopyrrolidine-1-carboxylate (51 mg, 0.27 mmol), diacetoxypalladium (5 mg, 0.02 mmol), 2-dicyclohexylphosphino-2',4',6'-triisopropylbiphenyl (28 mg, 0.06 mmol) and potassium carbonate (57 mg, 0.41 mmol). The mixture was purged with nitrogen then sealed and subjected to microwave irradiation at 110° C. for 3 h. The mixture was diluted with DCM (10 mL) and H$_2$O (10 mL). The layers were separated and the aqueous layer was extracted with (3×10 mL) DCM. The organic extracts were combined and washed with brine (1×10 mL), dried over sodium sulfate, filtered and concentrated in vacuo. The crude residue was then purified via ISCO chromatography (0-3% methanol/DCM) to deliver product (52 mg, 53%) as an off-white solid.

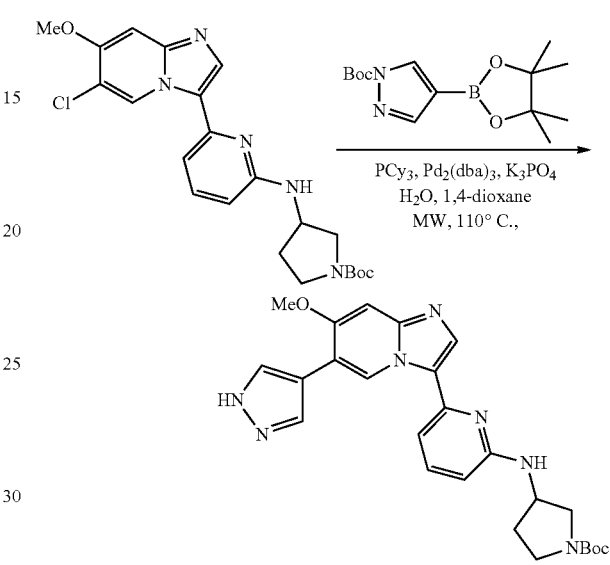

To an oven dried microwave vial equipped with a stir bar was added 6-(6-chloro-7-methoxyimidazo[1,2-a]pyridin-3-yl)-N-(pyrrolidin-3-yl)pyridin-2-amine (150 mg, 0.34 mmol), tert-butyl 4-(4,4,5,5-tetramethyl-1,3,2-dioxaborolan-2-yl)-1H-pyrazole-1-carboxylate (298 mg, 1.01 mmol), tricyclohexylphosphine (131 µL, 0.08 mmol, 20 wt. % in toluene), tris(dibenzylideneacetone)dipalladium(0) (31 mg, 0.034 mmol) and aqueous potassium phosphate (0.7 mL, 1.3 M). 1,4-dioxane (2.5 mL) was then added and the microwave vial was purged with nitrogen and sealed. The mixture was subjected to microwave irradiation at 110° C. for 3 h. The mixture was diluted with ethyl acetate (EtOAc) (20 mL) and H$_2$O (20 mL). The layers were separated and the aqueous layer was extracted (3×20 mL) EtOAc. The organic extracts were combined and washed with brine (1×20 mL), dried over sodium sulfate, filtered and concentrated in vacuo. The crude residue was then purified via ISCO chromatography (0-10% methanol/DCM) to deliver product (161 mg, 69%) as an off-white solid.

I-15

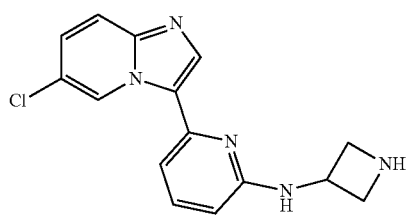

N-(azetidin-3-yl)-6-(6-chloroimidazo[1,2-a]pyridin-3-yl)pyridin-2-amine (I-15):

Method A. $^1$H NMR (400 MHz, DMSO-d$_6$) δ 8.80-8.60 (br.s, 2H), 8.43 (d, J=0.8 Hz, 1H), 8.34 (dd, J=9.6, 1.2 Hz, 1H), 7.73 (d, J=8.0 Hz, 1H), 7.66 (t, J=8.0 Hz, 1H), 7.50-7.44 (m, 2H), 6.57 (d, J=8.0 Hz, 1H), 4.86-4.76 (m, 1H), 4.37-4.26 (m, 2H), 4.06-3.96 (m, 2H); LC/MS: Method 1, retention time: 1.534 min; HRMS: m/z (M+H)$^+$=299.0938 (Calculated for C$_{15}$H$_{14}$ClN$_5$=299.0938).

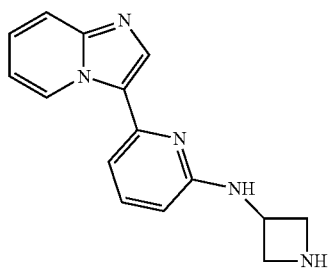

I-12

N-(azetidin-3-yl)-6-(imidazo[1,2-a]pyridin-3-yl)pyridin-2-amine (I-12):

Method A. $^1$H NMR (400 MHz, DMSO-d$_6$) δ 9.83 (dt, J=7.1, 1.2 Hz, 1H), 8.90-8.70 (br.s, 2H), 8.52 (s, 1H), 7.88 (dt, J=9.1, 1.2 Hz, 1H), 7.71 (ddd, J=8.9, 6.9, 1.3 Hz, 1H), 7.67-7.58 (m, 2H), 7.32 (td, J=7.0, 1.3 Hz, 1H), 7.24 (dd, J=7.5, 0.7 Hz, 1H), 6.53 (dd, J=8.3, 0.7 Hz, 1H), 4.90-4.77 (m, 1H), 4.30-4.16 (m, 2H), 3.96-3.86 (m, 2H); LC/MS: Method 1, retention time: 1.476 min; HRMS: m/z (M+H)$^+$=265.1327 (Calculated for C$_{15}$H$_{15}$N$_5$=265.1327).

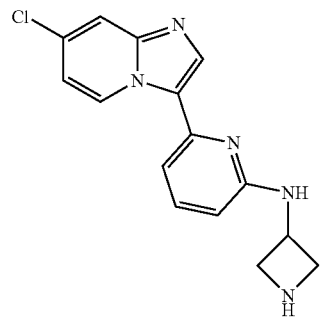

I-63

N-(azetidin-3-yl)-6-(7-chloroimidazo[1,2-a]pyridin-3-yl)pyridin-2-amine (I-63):

Method A. 1H NMR (400 MHz, DMSO-d6) □ □ 9.79 (dd, J=7.6, 0.8 Hz, 1H), 9.00-8.85 (br.s, 1H), 8.85-8.75 (br.s, 1H), 8.39 (s, 1H), 7.97 (dd, J=2.4, 0.8 Hz, 1H), 7.64-7.58 (m, 2H), 7.27-7.20 (m, 2H), 6.50 (dd, J=8.0, 0.8 Hz, 1H), 4.92-4.80 (m, 1H), 4.33-4.22 (m, 2H), 4.00-3.90 (m, 2H); LC/MS: Method 1, retention time: 1.303 min; HRMS: m/z (M+H)$^+$=299.0938 (Calculated for C$_{15}$H$_{14}$ClN$_5$=299.0938).

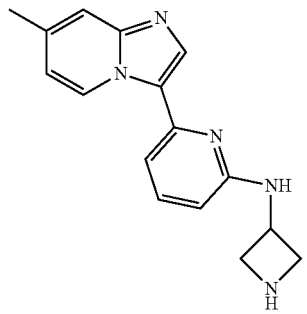

I-61

N-(azetidin-3-yl)-6-(7-methylimidazo[1,2-a]pyridin-3-yl)pyridin-2-amine (I-61):

Method A. $^1$H NMR (400 MHz, DMSO-d$_6$) δ 9.81 (d, J=7.2 Hz, 1H), 9.15-9.00 (br.s, 1H), 8.95-8.80 (br.s, 1H), 8.69 (s, 1H), 7.84-7.82 (m, 1H), 7.74 (d, J=6.0 Hz, 1H), 7.67 (dd, J=8.4, 7.6 Hz, 1H), 7.41 (dd, J=7.2, 0.4 Hz, 1H), 7.26 (dd, J=7.6, 0.4 Hz, 1H), 6.61 (dd, J=8.4, 0.4 Hz, 1H), 4.95-4.80 (m, 1H), 4.30-4.20 (m, 2H), 4.00-3.90 (m, 2H), 2.57 (s, 3H); LC/MS: Method 1, retention time: 1.634 min; HRMS: m/z (M+H)$^+$=279.1484 (Calculated for C$_{16}$H$_{17}$N$_5$=279.1484).

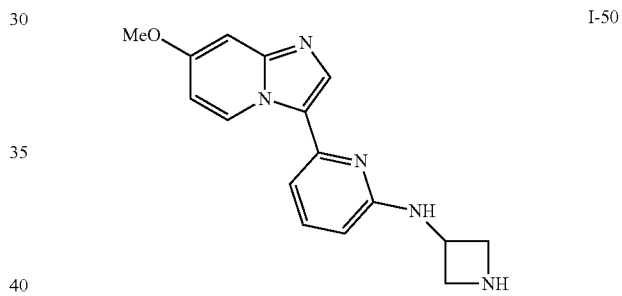

I-50

N-(azetidin-3-yl)-6-(7-methoxyimidazo[1,2-a]pyridin-3-yl)pyridin-2-amine (I-50):

Method A. $^1$H NMR (400 MHz, DMSO-d$_6$) δ 9.77 (d, J=8.0 Hz, 1H), 9.20-9.05 (br.s, 1H), 8.95-8.70 (br.s, 1H), 8.55 (s, 1H), 7.71 (d, J=6.0 Hz, 1H), 7.65 (dd, J=8.4, 7.6 Hz, 1H), 7.35 (d, J=2.4 Hz, 1H), 7.23 (dd, J=8.0, 0.8 Hz), 7.19 (dd, J=8.0, 2.4 Hz, 1H), 6.58 (dd, J=8.0, 0.8 Hz, 1H), 4.92-4.82 (m, 1H), 4.32-4.22 (m, 2H), 4.01 (s, 3H), 3.98-3.90 (m, 2H); LC/MS: Method 1, retention time: 1.627 min; HRMS: m/z (M+H)$^+$=295.1433 (Calculated for C$_{16}$H$_{17}$N$_5$O=295.1433).

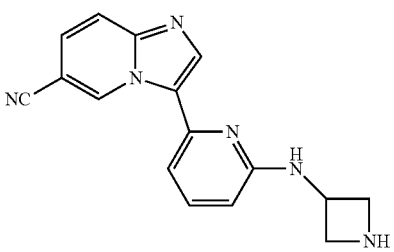

I-60

3-(6-(azetidin-3-ylamino)pyridin-2-yl)imidazo[1,2-a]pyridine-6-carbonitrile (I-60):

Method A. ¹H NMR (400 MHz, DMSO-d₆) δ 10.22 (d, J=0.8 Hz, 1H), 9.00-8.80 (br.s, 2H), 8.42 (s, 1H), 7.87 (dd, J=9.6, 0.8 Hz, 1H), 7.66-7.60 (m, 3H), 7.27 (d, J=8.0 Hz, 1H), 6.51 (d, J=8.0 Hz, 1H), 4.82-4.70 (m, 1H), 4.37-4.26 (m, 2H), 4.06-3.90 (m, 2H); LC/MS: Method 1, retention time: 1.772 min; HRMS: m/z (M+H)⁺=290.1280 (Calculated for $C_{16}H_{14}N_6$=290.1280).

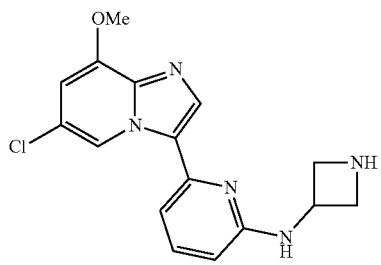

I-42

N-(azetidin-3-yl)-6-(6-chloro-8-methoxyimidazo[1,2-a]pyridin-3-yl)pyridin-2-amine (I-42):

Method A. ¹H NMR (400 MHz, DMSO-d₆) δ 9.45 (s, 1H), 8.90-8.75 (br.s, 2H), 8.36 (s, 1H), 7.65-7.55 (m, 2H), 7.25 (d, J=8.0 Hz, 1H), 6.84 (s, 1H), 6.52 (d, J=8.0 Hz, 1H), 4.83-4.70 (m, 1H), 4.37-4.25 (m, 2H), 4.02 (s, 3H), 4.01-3.94 (m, 2H); LC/MS: Method 1, retention time: 1.058 min; HRMS: m/z (M+H)⁺=330.1105 (Calculated for $C_{16}H_{17}ClN_5O$=330.1122).

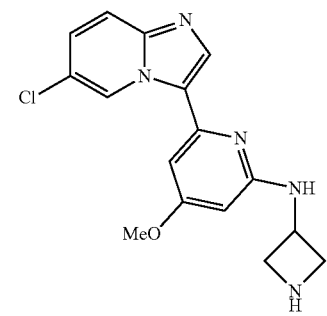

I-67

N-(azetidin-3-yl)-6-(6-chloroimidazo[1,2-a]pyridin-3-yl)-4-methoxypyridin-2-amine (I-67):

Method A. ¹H NMR (400 MHz, DMSO-d₆) δ 9.96 (dd, J=2.4, 0.8 Hz, 1H), 9.00-8.80 (br.s, 2H), 8.48 (s, 1H), 7.83 (dd, J=9.6, 0.8 Hz, 1H), 7.58 (dd, J=9.6, 2.4 Hz, 1H), 7.55 (d, J=4.4 Hz, 1H), 6.95 (d, J=2.4 Hz, 1H), 6.02 (d, J=2.4 Hz, 1H), 4.80-4.70 (m, 1H), 4.36-4.26 (m, 2H), 4.03-3.92 (m, 2H), 3.84 (s, 3H); LC/MS: Method 1, retention time: 1.821 min; HRMS: m/z (M+H)⁺=329.1043 (Calculated for $C_{16}H_{16}ClN_5O$=329.1043).

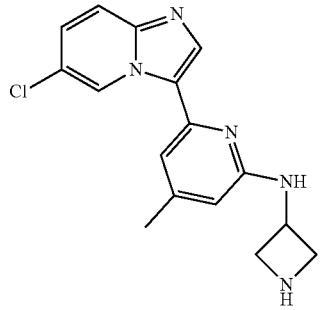

I-55

N-(azetidin-3-yl)-6-(6-chloroimidazo[1,2-a]pyridin-3-yl)-4-methylpyridin-2-amine (I-55):

Method A. ¹H NMR (400 MHz, DMSO-d₆) δ 9.92 (d, J=1.0 Hz, 1H), 8.90-8.70 (br.s, 2H), 8.35 (s, 1H), 7.78 (dd, J=9.6, 0.8 Hz, 1H), 7.50 (dd, J=9.6, 2.0 Hz, 1H), 7.44 (dd, J=9.6, 2.0 Hz, 1H), 7.15 (t, J=1.0 Hz, 1H), 6.32 (t, J=1.0 Hz, 1H), 4.80-4.70 (m, 1H), 4.37-4.25 (m, 2H), 4.05-3.92 (m, 2H), 2.27 (s, 3H); LC/MS: Method 1, retention time: 1.816 min; HRMS: m/z (M+H)⁺=313.1094 (Calculated for $C_{16}H_{16}ClN_5$=313.1094).

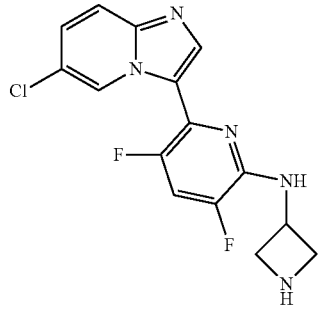

I-56

N-(azetidin-3-yl)-6-(6-chloroimidazo[1,2-a]pyridin-3-yl)-3,5-difluoropyridin-2-amine (I-56):

Method A. ¹H NMR (400 MHz, DMSO-d₆) δ 9.58 (dd, J=2.0, 0.8 Hz, 1H), 9.00-8.80 (br.s, 2H), 8.16 (d, J=3.6 Hz, 1H), 7.99 (t, J$_{HF}$=10.0 Hz, 1H), 7.83 (dd, J=9.6, 0.8 Hz, 1H), 7.71 (d, J=5.6 Hz, 1H), 7.56 (dd, J=9.6, 2.0 Hz, 1H), 4.90-4.82 (m, 1H), 4.34-4.24 (m, 2H), 4.18-4.08 (m, 2H); LC/MS: Method 1, retention time: 1.739 min; HRMS: m/z (M+H)⁺=335.0749 (Calculated for $C_{15}H_{12}ClF_2N_5$=335.0749).

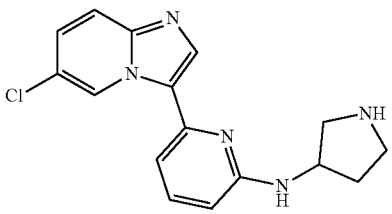

I-16

6-(6-chloroimidazo[1,2-a]pyridin-3-yl)-N-(pyrrolidin-3-yl)pyridin-2-amine (I-16):

Method A. ¹H NMR (400 MHz, DMSO-d₆) δ 10.04 (s, 1H), 9.00-8.80 (br.s, 2H), 8.38 (s, 1H), 7.77 (dd, J=9.6, 0.8

Hz, 1H), 7.56 (dd, J=8.3, 7.5 Hz, 1H), 7.48 (dd, J=9.6, 2.1 Hz, 1H), 7.22 (dd, J=7.5, 0.7 Hz, 1H), 7.11 (d, J=5.1 Hz, 1H), 6.47 (dd, J=8.3, 0.7 Hz, 1H), 4.55-4.45 (m, 1H), 3.50-3.40 (m, 1H), 3.40-3.25 (m, 3H), 2.38-2.24 (m, 1H), 2.09-1.97 (m, 1H); LC/MS: Method 1, retention time: 1.750 min; HRMS: m/z (M+H)$^+$=313.1094 (Calculated for C$_{16}$H$_{16}$ClN$_5$=313.1094).

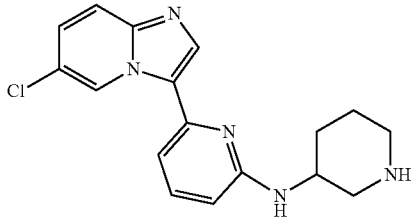

6-(6-chloroimidazo[1,2-a]pyridin-3-yl)-N-(piperidin-3-yl)pyridin-2-amine (I-17)

Method A. LC/MS: Method 1, retention time: 1.793 min.

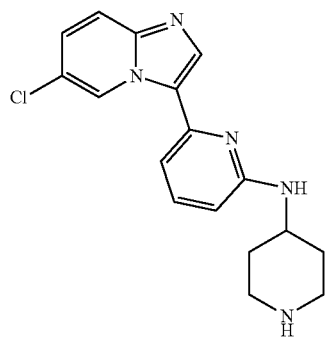

6-(6-chloroimidazo[1,2-a]pyridin-3-yl)-N-(piperidin-4-yl)pyridin-2-amine (I-2):

Method A. $^1$H NMR (400 MHz, DMSO-d$_6$) δ 10.15 (dd, J=2.0, 0.8 Hz, 1H), 8.70-8.60 (br.s, 1H), 8.60-8.55 (br.s, 1H), 8.54 (s, 1H), 7.89 (dd, J=9.6, 0.8 Hz, 1H), 7.67 (dd, J=9.6, 2.0 Hz, 1H), 7.55 (dd, J=8.4, 7.6 Hz, 1H), 7.20 (dd, J=7.6, 0.8 Hz, 1H), 7.18-7.05 (br.s, 1H), 6.51 (dd, J=8.4, 0.8 Hz, 1H), 4.10-3.95 (m, 1H), 3.46-3.36 (m, 2H), 3.14-3.02 (m, 2H), 2.24-2.14 (m, 2H), 1.80-1.66 (m, 2H); LC/MS: Method 1, retention time: 1.862 min; HRMS: m/z (M+H)$^+$=327.1251 (Calculated for C$_{17}$H$_{18}$ClN$_5$=327.1251).

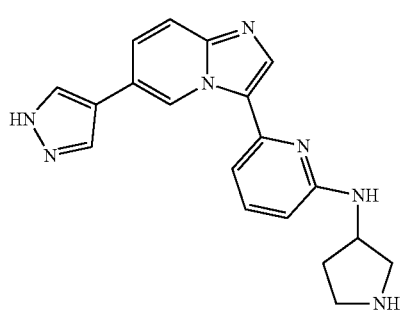

6-(6-(1H-pyrazol-4-yl)imidazo[1,2-a]pyridin-3-yl)-N-(pyrrolidin-3-yl)pyridin-2-amine (I-54):

Method A. $^1$H NMR (400 MHz, DMSO-d$_6$) δ 9.94 (s, 1H), 9.10-8.95 (br.s, 1H), 8.90-8.80 (br.s, 1H), 8.53 (s, 1H), 8.13 (s, 1H), 7.64 (dd, J=8.6, 7.5 Hz, 1H), 7.43 (s, 1H), 7.26 (d, J=5.1 Hz, 1H), 7.23 (d, J=5.1 Hz, 1H), 6.59 (d, J=8.0 Hz, 1H), 4.70-4.53 (m, 1H), 4.10 (s, 3H), 3.40-3.27 (m, 1H), 3.26-3.10 (m, 3H), 2.20-2.10 (m, 1H), 2.10-2.00 (m, 1H); LC/MS: Method 1, retention time: 1.665 min; HRMS: m/z (M+H)$^+$=345.1702 (Calculated for C$_{19}$H$_{19}$N$_7$=345.1702).

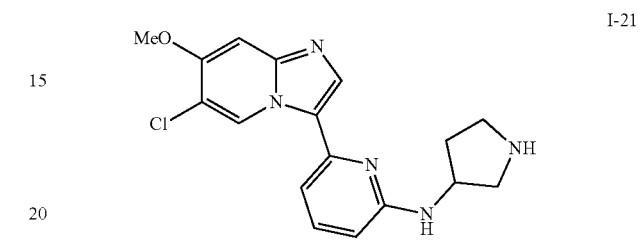

6-(6-chloro-7-methoxyimidazo[1,2-a]pyridin-3-yl)-N-(pyrrolidin-3-yl)pyridin-2-amine (I-21):

Method A. $^1$H NMR (400 MHz, DMSO-d$_6$) δ 10.14 (s, 1H), 9.05-8.75 (br.s, 2H), 8.40 (s, 1H), 7.58 (t, J=8.0 Hz, 1H), 7.39 (s, 1H), 7.22 (d, J=8.0 Hz, 1H), 7.16 (d, J=4.8 Hz, 1H), 6.50 (d, J=8.0 Hz, 1H), 4.55-4.45 (m, 1H), 4.04 (s, 3H), 3.55-3.45 (m, 1H), 3.45-3.25 (m, 3H), 2.40-2.25 (m, 1H), 2.12-2.00 (m, 1H); LC/MS: Method 1, retention time: 1.896 min; HRMS: m/z (M+H)$^+$=343.1200 (Calculated for C$_{17}$H$_{18}$ClN$_5$O=343.1200).

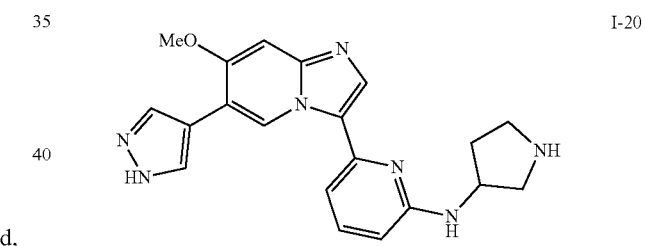

6-(7-methoxy-6-(1H-pyrazol-4-yl)imidazo[1,2-a]pyridin-3-yl)-N-(pyrrolidin-3-yl)pyridin-2-amine (I-20):

Method A. $^1$H NMR (400 MHz, DMSO-d$_6$) δ 9.93 (s, 1H), 9.02 (br.s, 1H), 8.86 (br.s, 1H), 8.52 (s, 1H), 8.13 (s, 2H), 7.64 (dd, J=8.4, 7.5 Hz, 1H), 7.42 (s, 1H), 7.26-7.21 (m, 2H), 6.59 (dd, J=8.4, 0.7 Hz, 1H), 4.60-4.56 (m, 1H), 4.10 (s, 3H), 3.39-3.31 (m, 1H), 3.19-3.14 (m, 3H), 2.19-2.10 (m, 1H), 2.07-1.99 (m, 1H); LC/MS: Method 1, retention time: 2.829 min; HRMS: m/z (M+H)$^+$=375.1808 (Calculated for C$_{20}$H$_{21}$N$_7$O=375.1808).

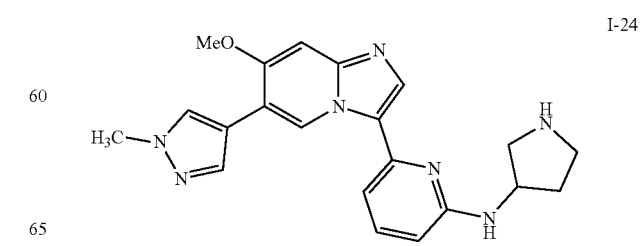

6-(7-methoxy-6-(1-methyl-1H-pyrazol-4-yl)imidazo[1,2-a]pyridin-3-yl)-N-(pyrrolidin-3-yl)pyridin-2-amine (I-24):

Method A. $^1$H NMR (400 MHz, DMSO-d$_6$) δ 9.88 (s, 1H), 8.90 (br.s, 1H), 8.78 (br.s, 1H), 8.44 (s, 1H), 8.22 (s, 1H), 7.90 (d, J=0.8 Hz, 1H), 7.62 (dd, J=8.4, 7.4 Hz, 1H), 7.36 (s, 1H), 7.22-7.17 (m, 2H), 6.56 (d, J=8.3 Hz, 1H), 4.59-4.55 (m, 1H), 4.08 (s, 3H), 3.91 (s, 3H), 3.25-3.17 (m, 2H), 2.20-2.11 (m, 1H), 2.08-1.99 (m, 1H); LC/MS: Method 1, retention time: 3.005 min; HRMS: m/z (M+H)$^+$=389.1964 (Calculated for C$_{21}$H$_{23}$N$_7$O=389.1964).

6-(6-(3,5-dimethylisoxazol-4-yl)-7-methoxyimidazo[1,2-a]pyridin-3-yl)-N-(pyrrolidin-3-yl)pyridin-2-amine (I-28):

Method A. $^1$H NMR (400 MHz, DMSO-d$_6$) δ 9.67 (s, 1H), 8.87 (br.s, 2H), 8.45 (s, 1H), 7.62-7.58 (m, 1H), 7.38 (s, 1H), 7.23-7.21 (m, 1H), 7.11-7.09 (m, 1H), 6.98 (s, 1H), 6.51 (d, J=8.3 Hz, 1H), 4.35-4.33 (m, 1H), 3.98 (s, 3H), 3.20-3.15 (m, 3H), 2.34 (s, 3H), 2.11 (s, 3H), 2.07-1.91 (m, 2H); LC/MS: Method 1, retention time: 3.066 min; HRMS: m/z (M+H)$^+$=404.1961 (Calculated for C$_{22}$H$_{24}$N$_6$O$_2$=404.1961).

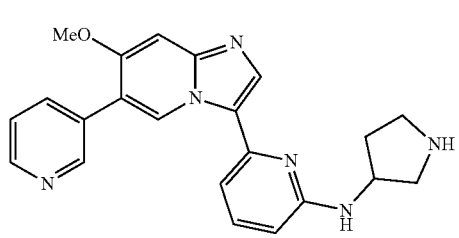

I-22

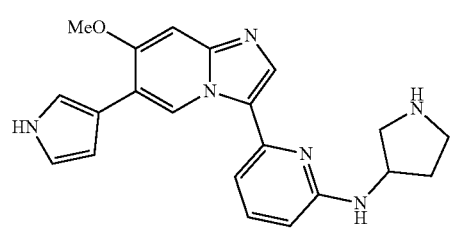

I-27

6-(7-methoxy-6-(pyridin-3-yl)imidazo[1,2-a]pyridin-3-yl)-N-(pyrrolidin-3-yl)pyridin-2-amine (I-22):

Method A. $^1$H NMR (400 MHz, DMSO-d$_6$) δ 9.92 (s, 1H), 8.98 (br.s, 1H), 8.90 (br.s, 1H), 8.82 (d, J=2.2 Hz, 1H), 8.69 (dd, J=4.9, 1.6 Hz, 1H), 8.63 (s, 1H), 8.08 (dt, J=8.0, 1.9 Hz, 1H), 7.65-7.57 (m, 2H), 7.52 (s, 1H), 7.27-7.22 (m, 2H), 6.57 (d, J=8.4 Hz, 1H), 4.45 (s, 1H), 4.04 (s, 3H), 3.31-3.23 (m, 1H), 3.16-3.05 (m, 2H), 2.00-1.88 (m, 2H); LC/MS: Method 1, retention time: 2.723 min; HRMS: m/z (M+H)$^+$=386.1855 (Calculated for C$_{22}$H$_{22}$N$_6$O=386.1855).

6-(7-methoxy-6-(1H-pyrrol-3-yl)imidazo[1,2-a]pyridin-3-yl)-N-(pyrrolidin-3-yl)pyridin-2-amine (I-27):

Method A. $^1$H NMR (400 MHz, DMSO-d$_6$) δ 11.19 (s, 1H), 9.88 (s, 1H), 9.02 (br.s, 1H), 8.89 (br.s, 1H), 8.52 (s, 1H), 7.63 (dd, J=8.4, 7.5 Hz, 1H), 7.37-7.35 (m, 2H), 7.27-7.22 (m, 2H), 6.91-6.90 (m, 1H), 6.59 (dd, J=8.4, 0.7 Hz, 1H), 6.48-6.47 (m, 1H), 4.65-4.60 (m, 1H), 4.09 (s, 3H), 3.26-3.16 (m, 3H), 2.24-2.15 (m, 1H), 2.05-1.97 (m, 1H); LC/MS: Method 1, retention time: 3.104 min; HRMS: m/z (M+H)$^+$=374.1855 (Calculated for C$_{21}$H$_{22}$N$_6$O=374.1855).

Method C.
Used for the synthesis of compound I-68.

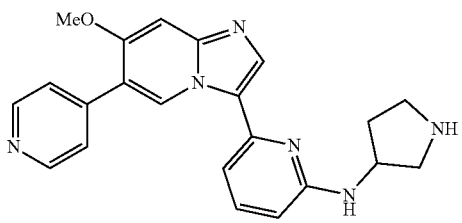

I-23

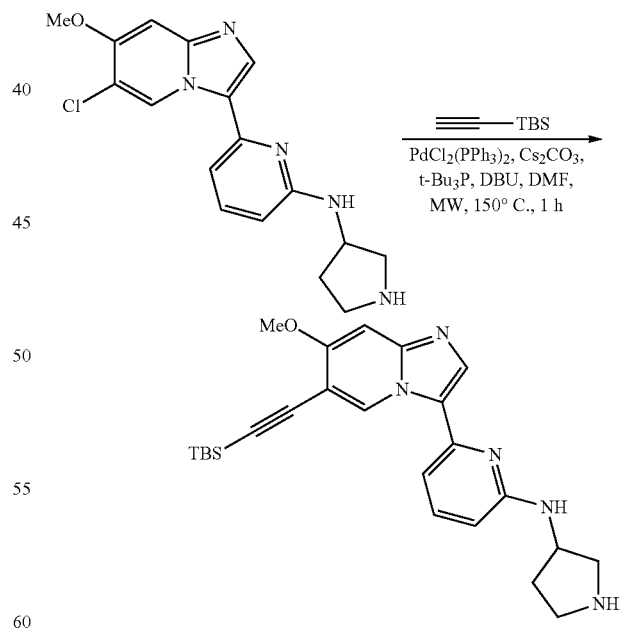

6-(7-methoxy-6-(pyridin-4-yl)imidazo[1,2-a]pyridin-3-yl)-N-(pyrrolidin-3-yl)pyridin-2-amine (I-23):

Method A. $^1$H NMR (400 MHz, DMSO-d$_6$) δ 9.94 (s, 1H), 8.91 (s, 1H), 8.82 (s, 1H), 8.76 (d, J=4 Hz, 2H), 8.59 (s, 1H), 7.71-7.70 (m, 2H), 7.62 (dd, J=8.4, 7.5 Hz, 1H), 7.49 (s, 1H), 7.25 (dd, J=7.4, 0.7 Hz, 1H), 7.18 (d, J=5.6 Hz, 1H), 6.56 (dd, J=8.4, 0.7 Hz, 1H), 4.44 (s, 1H), 4.04 (s, 3H), 3.30-3.22 (m, 1H), 3.19-3.13 (m, 3H), 2.01-1.91 (m, 2H); LC/MS: Method 1, retention time: 2.581 min; HRMS: m/z (M+H)$^+$=386.1855 (Calculated for C$_{22}$H$_{22}$N$_6$O=386.1855).

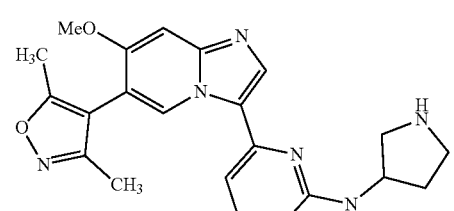

I-28

An oven dried microwave vial was charged with tert-butyl 3-((6-(6-chloro-7-methoxyimidazo[1,2-a]pyridine-3-yl)pyridine-2-yl)amino)pyrrolidine-1-carboxylate (30 mg, 0.068 mmol), tert-butyl(ethynyl)dimethylsilane (0.03 mL, 0.17 mmol), tri-tert-butylphosphine (0.135 mL, 0.14 mmol, 1 M solution in toluene), 1,8-diazabicyclo[5.4.0]undec-7- ene (2 μL, 0.014 mmol), cesium carbonate (44 mg, 0.14 mmol) and dichlorobis(triphenylphosphine)palladium(II) (5 mg, 0.007 mmol). DMF (0.5 mL) was then added and the microwave vial was purged with nitrogen and sealed. The mixture was subjected to microwave irradiation at 150° C. for 1 h. The crude mixture was purified via ISCO chromatography (50-100% EtOAc/hexanes) to deliver product (15 mg, 41%) as an off-white solid.

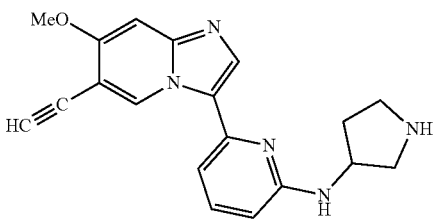

I-68

6-(6-ethynyl-7-methoxyimidazo[1,2-a]pyridin-3-yl)-N-(pyrrolidin-3-yl)pyridin-2-amine (I-68):

Method C. $^1$H NMR (400 MHz, DMSO-$d_6$) δ 10.04 (s, 1H), 8.91 (br. s, 2H), 8.30 (s, 1H), 7.58-7.54 (m, 1H), 7.21-7.18 (m, 2H), 7.13-7.12 (m, 1H), 6.57 (br. s, 1H), 6.46 (d, J=8.3 Hz, 1H), 4.49 (s, 1H), 4.38 (s, 1H), 3.96 (s, 3H), 2.34-2.29 (m, 1H), 2.08-2.05 (m, 1H). LC/MS: Method 1, retention time: 3.084 min; HRMS: m/z (M+H)$^+$=333.1590 (Calculated for $C_{19}H_{19}N_5O$=333.1590).

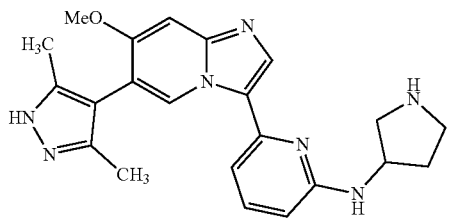

I-25

6-(6-(3,5-dimethyl-1H-pyrazol-4-yl)-7-methoxyimidazo[1,2-a]pyridin-3-yl)-N-(pyrrolidin-3-yl)pyridin-2-amine (I-25):

Method A. $^1$H NMR (400 MHz, DMSO-$d_6$) δ 9.64 (s, 1H), 8.93 (br.s, 2H), 8.62 (s, 1H), 7.64 (dd, J=8.4, 7.5 Hz, 1H), 7.43 (s, 1H), 7.25 (dd, J=7.5, 0.7 Hz, 1H), 7.19 (d, J=5.6 Hz, 1H), 6.58 (dd, J=8.4, 0.7 Hz, 1H), 4.34-4.30 (m, 1H), 4.01 (s, 3H), 3.32-3.26 (m, 1H), 3.17-3.03 (m, 2H), 2.08 (s, 6H), 2.00-1.90 (m, 2H); LC/MS: Method 1, retention time: 2.872 min; HRMS: m/z (M+H)$^+$=403.2121 (Calculated for $C_{22}H_{25}N_7O$=403.2121).

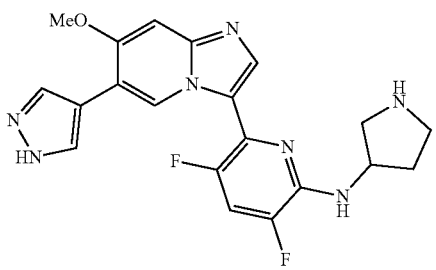

I-33

3,5-difluoro-6-(7-methoxy-6-(1H-pyrazol-4-yl)imidazo[1,2-a]pyridin-3-yl)-N-(pyrrolidin-3-yl)pyridin-2-amine (I-33)

Method A. $^1$H NMR (400 MHz, DMSO-$d_6$) δ 9.58 (s, 1H), 8.87-8.81 (br.m, 2H), 8.34 (d, J=2.6 Hz, 1H), 8.12 (s, 2H), 8.02 (dd, J=10.5, 9.7 Hz, 1H), 7.42 (s, 1H), 7.25 (d, J=8 Hz, 1H), 4.63-4.60 (m, 1H), 4.11 (s, 3H), 3.38-3.26 (m, 2H), 3.24-3.16 (m, 1H), 3.14-3.06 (m, 1H), 2.17-2.01 (m, 2H); LC/MS: Method 1, retention time: 2.872 min; HRMS: m/z (M+H)$^+$=411.1619 (Calculated for $C_{20}H_{19}F_2N_7O$=411.1619).

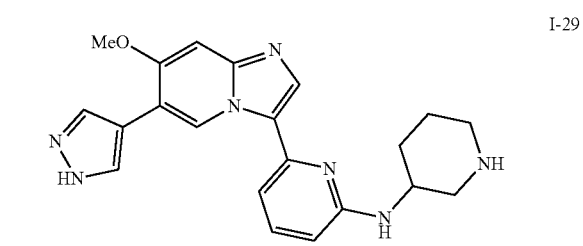 [SMILES: COc1cc2ncc(-c3cccc(NC4CCCNC4)n3)n2cc1-c1cn[nH]c1]

I-29

6-(7-methoxy-6-(1H-pyrazol-4-yl)imidazo[1,2-a]pyridin-3-yl)-N-(piperidin-3-yl)pyridin-2-amine (I-29):

Method A. $^1$H NMR (400 MHz, DMSO-$d_6$) δ 9.98 (s, 1H), 8.50 (s, 1H), 8.15 (br.s, 2H), 7.59 (dd, J=8.4, 7.4 Hz, 1H), 7.38 (s, 1H), 7.23 (s, 1H), 7.15 (dd, J=7.4, 0.7 Hz, 1H), 7.10-7.08 (m, 1H), 6.97 (s, 1H), 6.56 (d, J=8.3 Hz, 1H), 4.09 (s, 3H), 4.00 (s, 1H), 3.19-3.16 (m, 2H), 2.59-2.52 (m, 2H), 2.08-2.04 (m, 2H), 1.68-1.59 (m, 3H); LC/MS: Method 1, retention time: 2.943 min; HRMS: m/z (M+H)$^+$=389.1964 (Calculated for $C_{21}H_{23}N_7O$=389.1964).

Method D.

Used for the synthesis of compound I-32.

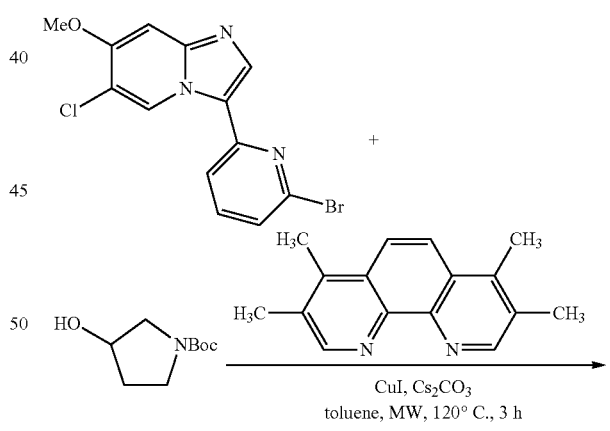

An oven dried microwave vial was charged with 3-(6-bromopyridin-2-yl)-6-chloro-7-methoxyimidazo[1,2-a]pyridine (100 mg, 0.30 mmol), tert-butyl 3-hydroxypyrrolidine-1-carboxylate (332 mg, 1.77 mmol), copper(I) iodide (14 mg, 0.07 mmol), cesium carbonate (722 mg, 2.22 mmol) and 3,4,7,8-tetramethyl-1,10-phenanthroline (35 mg, 0.15 mmol). Toluene (0.83 mL) was added and the vial was purged with nitrogen. The vial was sonicated before subjecting to microwave irradiation at 120° C. for 3 h. The mixture was diluted with DCM (20 mL) and H$_2$O (20 mL). The layers were separated and the aqueous layer was extracted with (3×20 mL) DCM. The organic extracts were combined and washed with brine (1×20 mL), dried over sodium sulfate, filtered and concentrated in vacuo. The crude residue was then purified via ISCO chromatography (70-100% EtOAc/hexanes) to deliver product (67 mg, 51%) as an off-white solid.

I-32

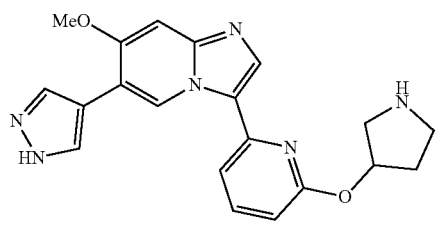

7-methoxy-6-(1H-pyrazol-4-yl)-3-(6-(pyrrolidin-3-yloxy)pyridin-2-yl)imidazo[1,2-a]pyri-dine (I-32):

Method D. $^1$H NMR (400 MHz, DMSO-d$_6$) δ 9.74 (s, 1H), 9.27 (br.s, 1H), 9.04 (br.s, 1H), 8.58 (s, 1H), 8.14 (s, 2H), 7.95 (t, J=7.9 Hz, 1H), 7.67 (d, J=7.5 Hz, 1H), 7.44 (s, 1H), 6.88 (d, J=8.2 Hz, 1H), 5.78-5.75 (m, 1H), 4.10 (s, 3H), 3.55-3.51 (m, 1H), 3.37-3.30 (m, 2H), 2.34-2.29 (m, 1H), 2.19-2.09 (m, 1H); LC/MS: Method 1, retention time: 2.812 min; HRMS: m/z (M+H)$^+$=376.1648 (Calculated for C$_{20}$H$_{20}$N$_6$O$_2$=376.1648).

I-31

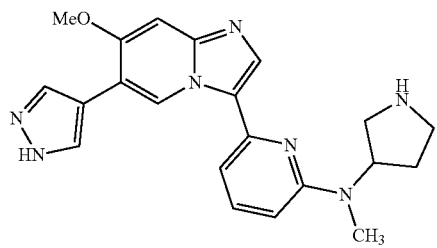

6-(7-methoxy-6-(1H-pyrazol-4-yl)imidazo[1,2-a]pyridin-3-yl)-N-methyl-N-(pyrrolidin-3-yl)pyridin-2-amine (I-31):

Method A. $^1$H NMR (400 MHz, DMSO-d$_6$) δ 9.92 (s, 1H), 8.94 (br.s, 1H), 8.81 (br.s, 1H), 8.53 (s, 1H), 8.09 (s, 2H), 7.75 (dd, J=8.6, 7.5 Hz, 1H), 7.39 (s, 1H), 7.29 (d, J=7.5 Hz, 1H), 7.24 (s, 1H), 7.11 (s, 1H), 6.98 (s, 1H), 6.84 (d, J=8.6 Hz, 1H), 5.30-5.26 (m, 1H), 4.09 (s, 3H), 3.20-3.17 (m, 1H), 3.03 (s, 3H), 3.00-2.93 (m, 1H), 2.23-2.15 (m, 1H), 2.10-2.02 (m, 1H); LC/MS: Method 1, retention time: 3.014 min; HRMS: m/z (M+H)$^+$=389.1964 (Calculated for C$_{21}$H$_{23}$N$_7$O=389.1964).

Method E.
Used for the synthesis of compound I-41.

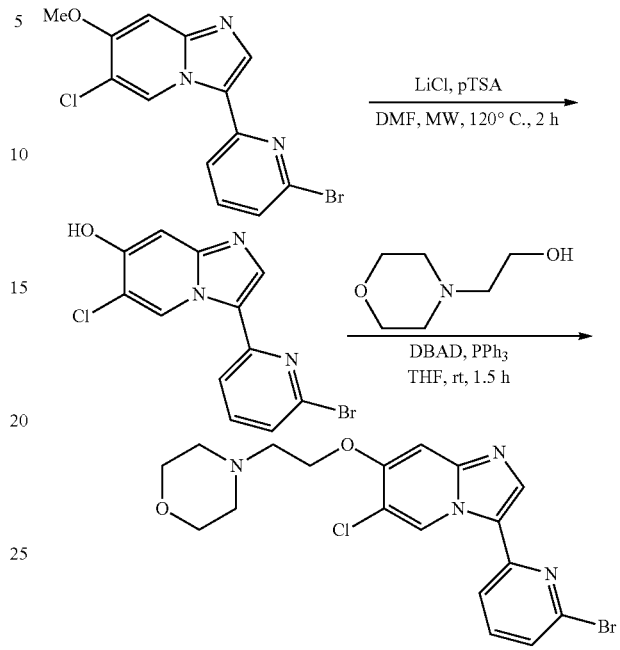

A microwave vial equipped with a stir bar was charged with 3-(6-bromopyridin-2-yl)-6-chloro-7-methoxyimidazo[1,2-a]pyridine (85 mg, 0.25 mmol), 4-methylbenzenesulfonic acid hydrate (239 mg, 1.3 mmol) and lithium chloride (53 mg, 1.3 mmol). DMF (1.3 mL) was then added and the vial was subjected to microwave irradiation at 120° C. for 2 h. The crude mixture was purified by reverse phase ISCO chromatography (1-100% acetonitrile/H$_2$O) to deliver product (24 mg, 29%) as an off-white solid.

A 25 mL round bottomed flask, equipped with a stir bar, was charged with 3-(6-bromopyridin-2-yl)-6-chloroimidazo[1,2-a]pyridine-7-ol (70 mg, 0.22 mmol), di-tert-butyl azodicarboxylate (89 mg, 0.39 mmol), 2-morpholinoethanol (51 mg, 0.39 mmol), THF (10 mL to 15 mL), and triphenylphosphine (102 mg, 0.39 mmol). The reaction mixture was stirred at room temperature for 1.5 h. The THF was removed in vacuo and the crude mixture was purified by ISCO chromatography (1-10% methanol/DCM) to deliver product (64 me, 67%) as an off-white solid.

I-41

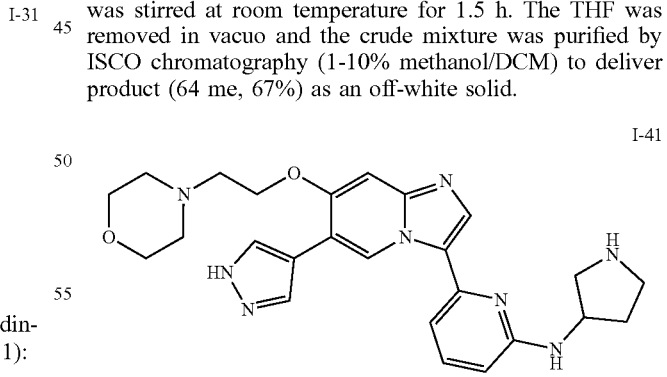

6-(7-(2-morpholinoethoxy)-6-(1H-pyrazol-4-yl)imidazo[1,2-a]pyridin-3-yl)-N-(pyrrolidin-3-yl)pyridin-2-amine (I-41):

Method E. $^1$H NMR (400 MHz, DMSO-d$_6$) δ 9.93 (s, 1H), 8.99 (br.s, 1H), 8.87 (br.s, 1H), 8.49 (s, 1H), 8.16 (s, 2H), 7.62 (t, J=7.9 Hz, 1H), 7.48 (s, 1H), 7.23-7.20 (m, =2H), 6.57 (d, J=8.4 Hz, 1H), 4.64-4.55 (m, 3H), 3.78-3.12 (m, 14H), 2.18-2.09 (m, 1H), 2.06-1.98 (m, 1H); LC/MS:

Method 1, retention time: 2.406 min; HRMS: m/z (M+H)$^+$=474.2492 (Calculated for C$_{25}$H$_{30}$N$_8$O$_2$=474.2492).

Example Set B—IC$_{50}$ Assays and Properties for Some Compounds

Methods—Cell Culture

THP-1 cells were purchased from the American Type Culture Collection (ATCC) and cultured in RPMI-1640 Medium (ATCC), 2-mercaptoethanol to a final concentration of 0.05 mM and 10% FBS. Hep G2 were purchased from ATCC and cultured in DMEM+sodium pyruvate with 10% FBS and 1% penicillin-streptomycin.

The MA9-FLT3-ITD cell line (also referred to as MLL-AF9/FLT3 ITD) is a leukemia cell line derived from CD34+ cord blood harboring both MLL-AF9 chromosomal translocation and stably expressed FLT3 ITD mutation. The MA9-FLT3-ITD cell line was provided by Dr. James Mulloy (Cincinnati Children's Hospital) and was cultured in IMDM with 20% FBS (Stemcell Technologies) and 1% penicillin-streptomycin.

Methods—Cell Titer Glo Assay Protocol

Supporting Table 1: Final 1536-well assay protocol

| Step | Parameter | Value | Description |
|---|---|---|---|
| 1 | Cells | 5 µL | 2500 cells/well |
| 2 | Controls | 23 nl | DMSO, Bortezomib |
| 3 | Library compounds | 23 nl | 57 µM to 0.4 nM dilution series |
| 4 | Incubation time | 48 hr | 37° C. |
| 5 | Reagent | 3 µL | Cell Titer Glo |
| 6 | Assay readout | luminescence | ViewLux |

| Step | Notes |
|---|---|
| 1 | Greiner white solid plates; 4 tips dispense to all wells |
| 2 | Column 1 media and DMSO only, Column 2 and 3 Bortezomib, column 4 DMSO |
| 3 | Pintool transfer (tip wash sequence; DMSO, iPA, MeOH, 3-s vacuum dry) |
| 4 | Plates covered with stainless steel rubber gasket-lined lids containing pin holes for gas exchange |
| 5 | Cell Titer Glo detection. Luciferase-based detection of ATP product |
| 6 | Perkin Elmer ViewLux, clear filter luminescent read |

Methods—HotSpot Assay

The HotSpot® kinase profiling and screening assays were carried out using the method of Anastassiadis et al., Nat. Biotechnol. (2011) Vol. 29, No. 11, pp. 1039-1045 (which is herein incorporated by reference in its entirety); 10 µM was the starting concentration with a 3-fold series dilution (10 doses) and the final ATP concentration was 10 µM.

Results

IC$_{50}$ determinations were measured against MA9-FLT3-ITD cells using Cell Titer Glo assay (Table 1).

TABLE 1

IC$_{50}$ determination.

| Compound No. | R$^1$ | R$^2$ | R$^3$ | R$^4$ | R$^5$ | R$^6$ | Y | m | n | IC$_{50}$$^a$ (nM) |
|---|---|---|---|---|---|---|---|---|---|---|
| I-15 | H | Cl | H | H | H | H | NH | 1 | 1 | 45 |
| I-12 | H | H | H | H | H | H | NH | 1 | 1 | 260 |
| I-63 | Cl | H | H | H | H | H | NH | 1 | 1 | 973 |
| I-61 | Me | H | H | H | H | H | NH | 1 | 1 | 442 |
| I-50 | OMe | H | H | H | H | H | NH | 1 | 1 | 120 |
| I-60 | H | CN | H | H | H | H | NH | 1 | 1 | 313 |
| I-42 | H | Cl | OMe | H | H | H | NH | 1 | 1 | 953 |
| I-67 | H | Cl | H | H | OMe | H | NH | 1 | 1 | 892 |
| I-55 | H | Cl | H | H | Me | H | NH | 1 | 1 | 291 |
| I-56 | H | Cl | H | F | H | F | NH | 1 | 1 | 157 |
| I-16 | H | Cl | H | H | H | H | NH | 1 | 2 | 30 |
| I-17 | H | Cl | H | H | H | H | NH | 1 | 3 | 22 |
| I-2 | H | Cl | H | H | H | H | NH | 2 | 2 | 16 |
| I-54 | H | 1H-pyrazol-4-yl | H | H | H | H | NH | 1 | 2 | 34 |
| I-21 | OMe | Cl | H | H | H | H | NH | 1 | 2 | 6 |
| I-20 | OMe | 1H-pyrazol-4-yl | H | H | H | H | NH | 1 | 2 | 5 |
| I-24 | OMe | 1-Me-pyrazol-4-yl | H | H | H | H | NH | 1 | 2 | <5 |
| I-22 | OMe | pyridin-3-yl | H | H | H | H | NH | 1 | 2 | 26 |
| I-23 | OMe | pyridin-4-yl | H | H | H | H | NH | 1 | 2 | 15 |
| I-28 | OMe | 3,5-dimethylisoxazolyl | H | H | H | H | NH | 1 | 2 | 140 |
| I-27 | OMe | 1H-pyrrol-3-yl | H | H | H | H | NH | 1 | 2 | 30 |

TABLE 1-continued

IC$_{50}$ determination.

| Compound No. | R$^1$ | R$^2$ | R$^3$ | R$^4$ | R$^5$ | R$^6$ | Y | m | n | IC$_{50}$$^a$ (nM) |
|---|---|---|---|---|---|---|---|---|---|---|
| I-68 | OMe | ethynyl | H | H | H | H | NH | 1 | 2 | 15 |
| I-25 | OMe | 3,5-di-Me-pyrazolyl | H | H | H | H | NH | 1 | 2 | 380 |
| I-33 | OMe | 1H-pyrazol-4-yl | H | F | H | F | NH | 1 | 2 | 53 |
| I-29 | OMe | 1H-pyrazol-4-yl | H | H | H | H | NH | 1 | 3 | 15 |
| I-32 | OMe | 1H-pyrazol-4-yl | H | H | H | H | O | 1 | 2 | 166 |
| I-31 | OMe | 1H-pyrazol-4-yl | H | H | H | H | N-Me | 1 | 2 | 298 |
| I-41 | 2-(morpholino)ethoxy | 1H-pyrazol-4-yl | H | H | H | H | NH | 1 | 2 | 68 |
| quizartinib | | | | | | | | | | |

$^a$The IC$_{50}$ values represent the average of three runs against MLL-AF9/FLT3-ITD cells using the Cell Titer Glo assay.

Compound I-50 (when R$^1$ was methoxy) exhibited the best cell-killing activity for MA9-FLT3-ITD cells of the tested compounds. With regard to R$^2$, compound I-12 and compound I-61 showed a decrease in activity compared to compound I-15. Introducing a small heterocycle at R$^2$, such as 1-H-pyrazol-4-yl (e.g., compound I-54) slightly improved the activity. Tested compounds with substitutions at the 8-position led to a decrease of activity as shown, for example, by compound I-42; a decrease in activity is also observed for the tested compounds with substitutions at the 2- or 5-position (data not shown). The tested compounds with substitution on the pyridine ring (e.g., compounds I-55, I-56, and I-67,) led to a decreased activity analogues; small size groups like 3,5-difluoro substitution (e.g., compound I-56) appeared to show modest decrease of activity. Among the tested compounds, it was found that the compounds with either 5-membered (compound I-16) or 6-membered cyclic amine (compound I-17 and compound I-2) showed ~2-fold improvement of potency compared to compound I-15. Compounds tested that had any derivatization of the free —NH of cyclic amine led to an apparent complete loss of cell-killing activity (data not shown).

Compound I-21 exhibited an IC$_{50}$ value of 6 nM, which was almost 8-fold more potent than compound I-15. Of the compounds tested, replacing the —Cl with -ethynyl (e.g., compound I-68) resulted in slightly decreased potency. Some tested compounds included heterocycles substituted at R$^2$ while keeping methoxy at the 7-position unchanged; the tested compounds without substitution on this heterocyclic ring (e.g., compounds I-20, I-22, I-23, I-24, and I-68) had a similar potency compared to compound I-54, while the tested compounds that had a substitution on the heterocyclic ring had variable changes in activity (e.g., compounds I-25 and I-28 decreased in activity while compound I-24 increased in activity).

Of the compounds tested, replacing the pyridine ring with 3,5-difluoropyridyl (compound I-33) resulted in 10-fold decrease of potency compared to compound I-20. The tested compounds which replaced the pyridine with a phenyl (data not shown) or a 1,3-pyrimidinyl (data not shown) exhibited micromolar range potency for MA9-FLT3-ITD cells. Also, replacing the —NH linkage at 2-position of pyridine ring with either ether (compound I-32) or N-Me (compound I-31) linkage led to a loss of potency for the compounds tested. Compound I-29 (with 6-membered cyclic amine) was 3-fold less potent than compound I-20. Compound I-41 was synthesized by attaching the solubilizing group 2-(morpholino) ethoxy at the 1-position of 1H-pyrazoyl ring; compound I-41 exhibited an almost 14-fold decrease of potency compared to compound I-20.

Compounds I-2, I-22, and I-24 and quizartinib were re-tested with lower starting concentration. Compound I-24 exhibited had an IC$_{50}$ value of 0.8 nM, which was 2-fold more potent than quizartinib (FIG. 1).

Selectivity towards FLT3 and IRAK1/4: Utilizing the HotSpot assay, we ascertained the IC$_{50}$ values for some compounds versus IRAK1, IRAK4, and FLT3 along with a panel of other kinases (Table 2).

TABLE 2

Inhibitory activities of compound I-2, I-22, and I-24 and quizartinib.

| | Compound IC$_{50}$ (nM) | | | |
|---|---|---|---|---|
| Kinase | I-2 | I-24 | I-22 | quizartinib |
| BLK | <0.5 | <0.5 | 104 | >10000 |
| CDK7/cyclin H | 177 | 174 | >10000 | >10000 |
| FLT3 | <0.5 | <0.5 | <0.5 | 2.23 |
| FLT3 (D835Y) | <0.5 | <0.5 | <0.5 | 108 |
| FLT3 (ITD) | <0.5 | <0.5 | 1 | 1.93 |
| IRAK1 | 31.7 | 22.6 | 1940 | >10000 |
| IRAK4 | 40 | 0.8 | 299 | >10000 |
| LCK | 0.9 | <0.5 | 148 | >10000 |
| PDGFRβ | 4.19 | 2.67 | 3.57 | 98.2 |
| RET | 0.6 | <0.5 | 1280 | 17.5 |
| SRPK1 | >10000 | >10000 | >10000 | >10000 |

Compounds I-2, I-22, and I-24 inhibited FLT3 and FLT3 (ITD), and also showed sub-nano molar potency for FLT3 (D835Y). Quizartinib exhibited weaker activity (IC$_{50}$=108 nM), indicating compounds I-2, I-22, and I-24 might overcome the quizartinib-resistant AML cell lines carrying FLT3 point mutation in TKD. Generally, compounds I-2, I-22, and I-24 exhibited better inhibitory activities for IRAK4 than IRAK1 but compound I-24 stood out with sub-nano molar potency for IRAK4, which, without being bound by theory, might be the cause that compound I-24 is ~27-fold more potent than compound I-2 for MA9-FLT3-ITD cells considering their similar inhibitory profiles for other 10 kinases screened. Quizartinib appeared inactive for both IRAK family kinases.

Compounds I-2, I-22, and I-24 were tested against THP-1 cells (a type of FLT3 wild type AML cells) and Hep G2 cells (a type of liver cancer cells). None of the compounds tested showed any inhibitory activity against THP-1 or Hep G2 cells even at >10 μM concentration (data not shown), suggesting high selectivity for MA9-FLT3-ITD cells and low toxicity due to off-target inhibition.

Compounds I-2, I-22, and I-24 showed subnamolar potency for both IRAK4 and FLT3, but also inhibited other kinases such as LCK, RET and PDGFRβ.

ADME profile: Early ADME profiling was performed using standard methods and included rat microsomal stability, PAMPA permeability and kinetic aqueous solubility. Overall, compounds I-2, I-22, and I-24 showed both good rat microsomal stability (RLM) and aqueous solubility (Table 3).

TABLE 3

In vitro ADME properties of compounds I-2, I-22, and I-24.

| Compound | $IC_{50}{}^a$ (nM) | $RLM\ T_{1/2}{}^b$ (min) | Permeability$^c$ ($10^{-6}$ cm/s) | Kinetic Solubility$^d$ (μM) |
|---|---|---|---|---|
| I-2 | 22 | >30.0 | 806.9 | >48.0 |
| I-24 | 0.8 | >30.0 | <1.3 | >58.0 |
| I-22 | 26 | >30.0 | <3.4 | 29 |

$^a IC_{50}$ against MLL-AF9 FLT3-ITD cells using a Cell Titer Glo Assay.
$^b T_{1/2}$ in rat liver microsomes (RLM) in the presence of NADPH.
$^c$PAMPA permeability at pH 7.4.
$^d$Kinetic aqueous solubility in PBS buffer (pH 7.4) as measured by UV quanitification.

Compound I-2 also showed good PAMPA permeability. Compounds I-22 and I-24 might mitigate their PAMPA permeability through intraperitoneal (IP) administration in animal studies. Compounds I-2, I-22, and I-24 were evaluated for their in vivo pharmacokinetic properties in NRG/NRGS mice (the strain of mice to be used in our MA9-FLT3-ITD AML disease model). The compounds were dosed through IP injection at 30 mg/kg and the plasma samples were collected for analysis (Table 4).

TABLE 4

Pharmacokinetic evaluations of compounds I-2, I-22, and I-24 in NRG/NRGS mice with IP injection at 30 mg/kg.$^{a,\ b}$

| Compound | $AUC_{inf}$ (hr*ng/mL) | $T_{1/2}$ (hr) | $T_{max}$ (hr) | $C_{max}$ (ng/mL) |
|---|---|---|---|---|
| I-2 | 4,630 | 3.3 | 0.5 | 1,710 |
| I-24 | 6,800 | 4.2 | 0.083 | 3,570 |
| I-22 | 4,850 | 3.9 | 0.5 | 1,540 |

$^a$Compounds I-2, I-22, and I-24 were all formulated as a solution in saline.
$^b$Plasma samples were collected at time point of 0.083, 0.25, 0.5, 1, 2, 4, 7, and 24 h after dosing.

Compounds I-2, I-22, and I-24 showed good and similar in vivo pharmacokinetic properties. Compound I-24 had better plasma exposure ($AUC_{inf}$=6,800 hr*ng/mL), higher concentration in plasma ($C_{max}$=3,570 ng/mL) and longer half-life ($T_{1/2}$=4.2 hr) compared to compounds I-2 and I-22.

Example Set C—Kd Kinase Assays

Kinase Assays.

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Most Kds were determined using a compound top concentration of 30,000 nM. If the initial Kd determined was <0.5 nM (the lowest concentration tested), the measurement was repeated with a serial dilution starting at a lower top concentration.

| Gene Symbol | Target | | | | |
|---|---|---|---|---|---|
| | Quizartinib | I-17 | Crenolinib | I-22 | I-24 |
| | Kd (nM) | | | | |
| FLT3 | 1.4 | 0.61 | 0.2 | 0.065 | 0.025 |
| FLT3 (D835H) | 2.1 | 0.64 | 0.2 | 0.11 | 0.27 |
| FLT3 (D835V) | 4.2 | 0.093 | 0.016 | 0.021 | 0.0099 |
| FLT3 (D835Y) | 7.6 | 0.4 | 0.19 | 0.12 | 0.29 |
| FLT3 (ITD) | 7 | 0.31 | 0.26 | 0.17 | 0.36 |
| FLT3 (ITD, D835V) | 480 | 0.036 | 0.023 | 0.014 | 0.01 |
| FLT3 (ITD, F691L) | 160 | 0.41 | 0.11 | 0.12 | 0.012 |
| FLT3 (K663Q) | 0.57 | 5 | 0.82 | 0.58 | 5.4 |
| FLT3 (N841I) | 1.5 | 1.2 | 0.39 | 0.24 | 0.33 |
| FLT3 (R834Q) | 12 | 3.4 | 1.3 | 0.42 | 0.3 |
| FLT3-auto-inhibited | 580 | 11 | 17 | 1.9 | 0.96 |
| IRAK1 | >30000 | 150 | 260 | 3.5 | 2.9 |
| IRAK4 | >30000 | 3.4 | 62 | 0.29 | 0.3 |

Example Set D—IC50 Kinase Assays and ADME

Compounds were tested against 11 kinases. Compounds were tested in 10-dose IC50 mode with 3-fold serial dilution starting at 10 μM, and are relative to DMSO, the negative control. The positive control, Staurosporine, was tested in a 10-dose IC50 mode with 4-fold serial dilution starting at 20 μM. Reactions were carried out at 10 μM ATP.

Curve fits were performed to determine IC50 where the enzyme activities at the highest concentration of compounds were less than 65%. IC50 values less than 5.08 E−10 M or higher than 1.00E−5 M is estimated based on the best curve fitting available.

|  | Compound IC50 (M) | | | | Staurosporine IC50 (M) |
|---|---|---|---|---|---|
| Kinase: | I-17 | I-20 | I-22 | I-24 | |
| BLK | 4.07E-08 | <5.08E-10 | <5.08E-10 | <5.08E-10 | 1.45E-09 |
| CDK7/cyclin H | 5.88E-07 | 1.16E-07 | 1.77E-07 | 1.74E-07 | 1.06E-07 |
| FLT3 | <5.08E-10 | <5.08E-10 | <5.08E-10 | <5.08E-10 | 1.58E-09 |
| FLT3 (D835Y) | <5.08E-10 | <5.08E-10 | <5.08E-10 | <5.08E-10 | 7.21E-11 |
| FLT3 (ITD) | <5.08E-10 | <5.08E-10 | <5.08E-10 | <5.08E-10 | 1.46E-09 |
| IRAK1 | 1.48E-06 | 5.34E-09 | 3.17E-08 | 2.26E-08 | 4.60E-08 |
| IRAK4 | 1.12E-08 | <5.08E-10 | 6.53E-10 | 8.08E-10 | 3.11E-09 |
| LCK | 1.67E-07 | <5.08E-10 | 9.38E-10 | <5.08E-10 | 2.17E-09 |
| PDGFRb | 6.70E-08 | 1.25E-09 | 4.19E-09 | 2.67E-09 | 2.72E-09 |
| RET | 1.05E-08 | <5.08E-10 | 6.31E-10 | <5.08E-10 | 2.17E-09 |
| SRPK1 | 7.67E-06 | >1.00E-05 | NI | NI | 3.34E-08 |

NI—indicates no inhibition or that compound activity data could not be fit to an IC50 curve.

|  | Compound IC50 (M) | | Staurosporine |
|---|---|---|---|
| Kinase: | Crenolinib | I-2 | Staurosporine |
| BLK | 2.07E-08 | 1.04E-07 | 8.03E-10 |
| CDK7/cyclin H | 1.26E-06 | NI | 5.99E-08 |
| FLT3 | 2.36E-10 | 3.56E-10 | 7.88E-10 |
| FLT3 (D835Y) | 1.77E-11 | 9.34E-12 | 6.21E-11 |
| FLT3 (ITD) | 6.23E-10 | 9.96E-10 | 1.23E-09 |
| IRAK1 | 1.16E-07 | 1.94E-06 | 1.89E-08 |
| IRAK4 | 2.06E-09 | 2.99E-07 | 2.75E-09 |
| LCK | 5.78E-08 | 1.48E-07 | 1.48E-09 |
| PDGFRb | 3.78E-08 | 3.57E-09 | 1.50E-08 |
| RET | 1.38E-08 | 1.28E-06 | 1.80E-09 |
| SRPK1 | 2.17E-05 | NI | 1.40E-08 |

NI—indicates no inhibition or that compound activity data could not be fit to an IC50 curve.

ADME and IC50 Data for Selected Compounds

| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-20 | (structure) | NCGC 00262327 | 11.6 | <6.9 | 4.5 | 33.170 | 0.040 |
| I-21 | (structure) | NCGC 00262326 | 27 | 29.9 | 7.7 | | |
| I-22 | (structure) | NCGC 00371479 | >30.0 | <3.4 | 29 | 9.920 | 0.026 |

-continued
| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-23 | 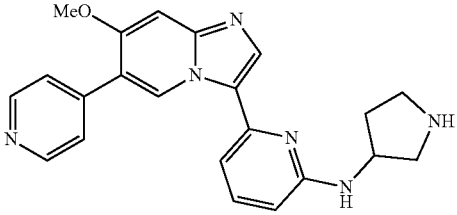 [SMILES: COc1cc2ncc(-c3cccc(NC4CCNC4)n3)n2cc1-c1ccncc1] | NCGC 00371480 | >30.0 | <3.6 | 11.6 | 1.830 | 0.015 |
| I-24 | 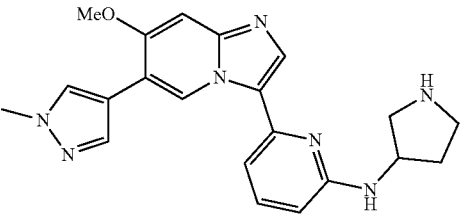 [SMILES: COc1cc2ncc(-c3cccc(NC4CCNC4)n3)n2cc1-c1cnn(C)c1] | NCGC 00371481 | >30.0 | <1.3 | >58.0 |  | 0.004 |
| I-25 | 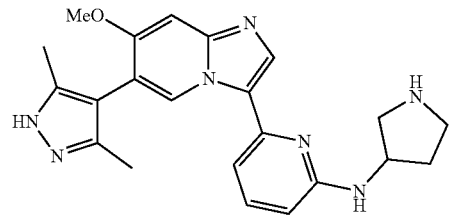 [SMILES: COc1cc2ncc(-c3cccc(NC4CCNC4)n3)n2cc1-c1c(C)n[nH]c1C] | NCGC 00371482 | >30.0 | <1.7 | >60.0 | 15.720 | 0.380 |
| I-26 | 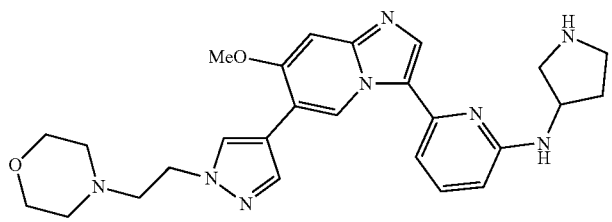 [SMILES: COc1cc2ncc(-c3cccc(NC4CCNC4)n3)n2cc1-c1cnn(CCN2CCOCC2)c1] | NCGC 00371483 | >30.0 | <1.5 | >72.0 | 15.720 | 0.020 |
| I-27 | 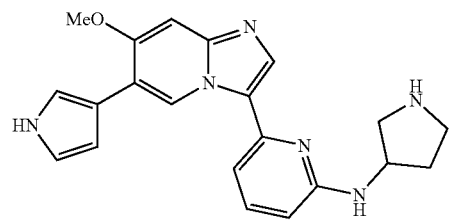 [SMILES: COc1cc2ncc(-c3cccc(NC4CCNC4)n3)n2cc1-c1cc[nH]c1] | NCGC 00371484 | >30.0 | <2.3 | 34.3 | 4.430 | 0.030 |
| I-28 | 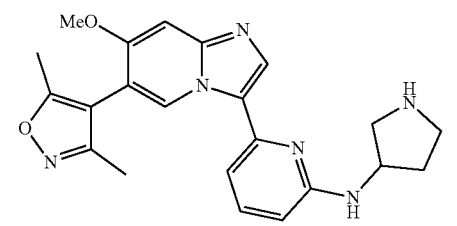 [SMILES: COc1cc2ncc(-c3cccc(NC4CCNC4)n3)n2cc1-c1c(C)noc1C] | NCGC 00371488 | 15.7 | <4.7 | >60.0 | 14.820 | 0.140 |

-continued

| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-29 | 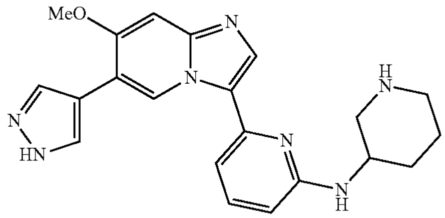 [SMILES: COc1cc2ncc(-c3cccc(NC4CCCNC4)n3)n2cc1-c1cn[nH]c1] | NCGC 00371485 | 9.8 | <3.6 | 35.6 | 9.350 | 0.015 |
| I-30 | 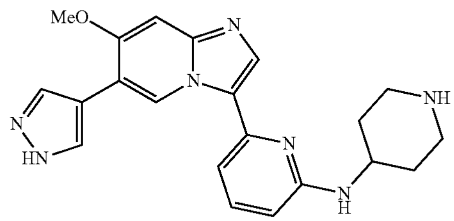 [SMILES: COc1cc2ncc(-c3cccc(NC4CCNCC4)n3)n2cc1-c1cn[nH]c1] | NCGC 00371486 | 24.7 | <3.1 | 12.3 | | |
| I-31 | 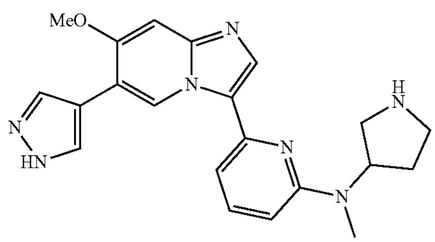 [SMILES: COc1cc2ncc(-c3cccc(N(C)C4CCNC4)n3)n2cc1-c1cn[nH]c1] | NCGC 00371487 | 11.5 | <3.3 | 14.1 | 16.630 | 0.298 |
| I-32 | 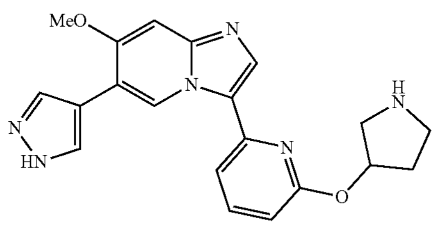 [SMILES: COc1cc2ncc(-c3cccc(OC4CCNC4)n3)n2cc1-c1cn[nH]c1] | NCGC 00371852 | 7.7 | <3.9 | 8.2 | 3.720 | 0.166 |
| I-33 | 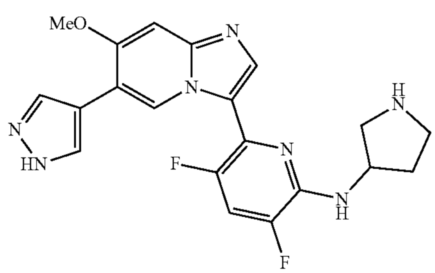 [SMILES: COc1cc2ncc(-c3nc(NC4CCNC4)c(F)cc3F)n2cc1-c1cn[nH]c1] | NCGC 00371853 | 9.3 | <10.9 | 3.9 | 29.760 | 0.053 |
| I-36 | 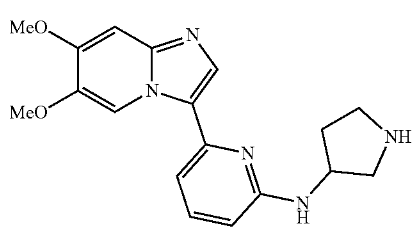 [SMILES: COc1cc2ncc(-c3cccc(NC4CCNC4)n3)n2cc1OC] | NCGC 00371850 | >30.0 | <3.8 | >50.0 | 4.430 | 0.017 |

-continued

| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-37 | 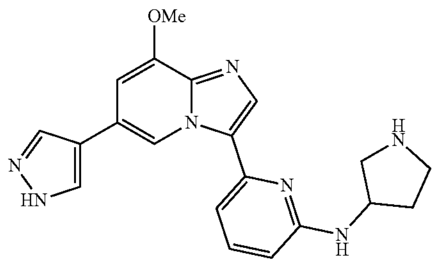 [SMILES: COc1cc(-c2cn[nH]c2)cn2c(-c3cccc(NC4CCNC4)n3)cnc12] | NCGC 00371857 | 2.3 | <1.6 | >55.0 | 16.630 | 2.221 |
| I-38 | 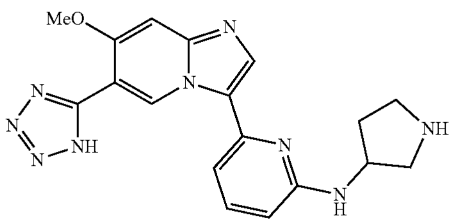 [SMILES: COc1cc2ncc(-c3cccc(NC4CCNC4)n3)n2cc1-c1nnn[nH]1] | NCGC 00371858 | >30.0 | <2.4 | >56.0 | 0.002 | 6.255 |
| I-39 | 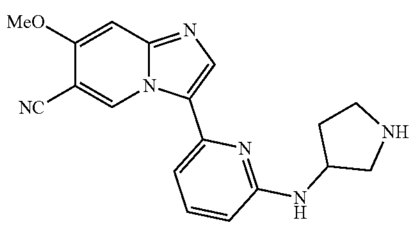 [SMILES: COc1cc2ncc(-c3cccc(NC4CCNC4)n3)n2cc1C#N] | NCGC 00371859 | 8.8 | <1.8 | 10.6 | 5.580 | 0.033 |
| I-40 | 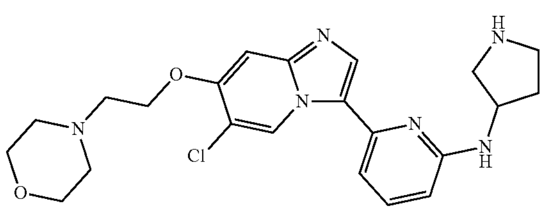 [SMILES: Clc1cn2c(-c3cccc(NC4CCNC4)n3)cnc2cc1OCCN1CCOCC1] | NCGC 00371957 | >30.0 | <1.5 | >65.0 | 0.626 | 0.008 |
| I-41 | 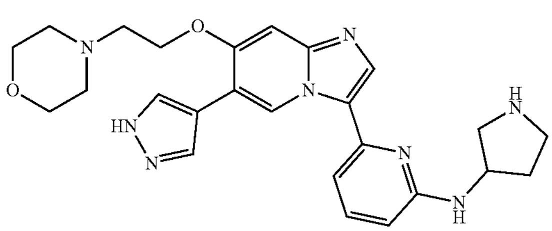 [SMILES: c1cc(NC2CCNC2)nc(-c2cnc3cc(OCCN4CCOCC4)c(-c4cn[nH]c4)cn23)c1] | NCGC 00371958 | >30.0 | <1.1 | >70.0 | 17.640 | 0.068 |
| I-15 | 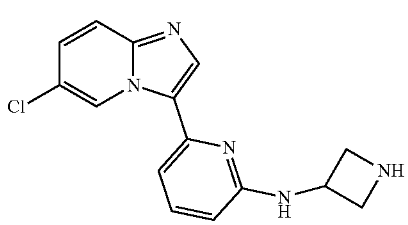 [SMILES: Clc1ccc2ncc(-c3cccc(NC4CNC4)n3)n2c1] | NCGC 00241410 | 13 | 181.6 | >44.0 | 16.630 | 1.177 |

-continued

| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-42 | 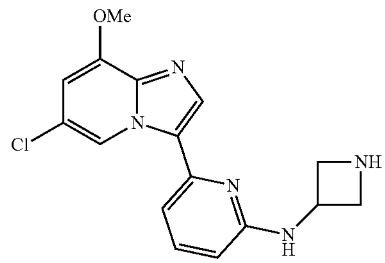 [SMILES: COc1cc(Cl)cn2c(-c3cccc(NC4CNC4)n3)cnc12] | NCGC 00262331 | >30 | <6.1 | >49.0 | 20.930 | 0.953 |
| I-43 | 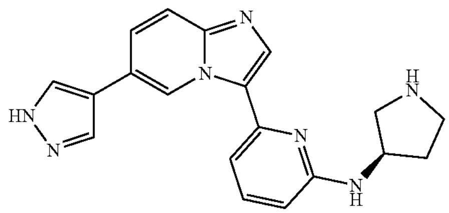 [SMILES: c1cc(N[C@@H]2CCNC2)nc(-c2cnc3ccc(-c4cn[nH]c4)cn23)c1] | NCGC 00262376 | 5.7 | <1.5 | 40.1 | | 0.076 |
| I-44 | 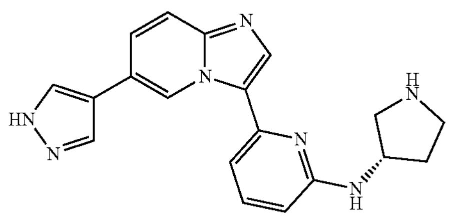 [SMILES: c1cc(N[C@H]2CCNC2)nc(-c2cnc3ccc(-c4cn[nH]c4)cn23)c1] | NCGC 00262377 | 6.7 | <1.6 | 42.6 | | 0.017 |
| I-45 | 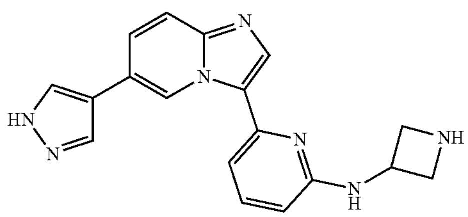 [SMILES: c1cc(NC2CNC2)nc(-c2cnc3ccc(-c4cn[nH]c4)cn23)c1] | NCGC 00249356 | N/A | <2.0 | >49.0 | 4.290 | 0.460 |
| I-46 | 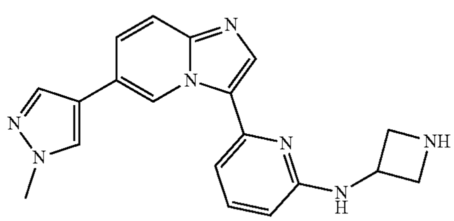 [SMILES: Cn1cc(-c2ccc3ncc(-c4cccc(NC5CNC5)n4)n3c2)cn1] | NCGC 00249357 | >30.0 | <2.0 | 43.1 | 16.630 | 0.213 |
| I-16 | 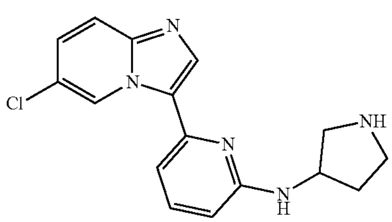 [SMILES: Clc1ccc2ncc(-c3cccc(NC4CCNC4)n3)n2c1] | NCGC 00249372 | 25.6 | 332.2 | >46.0 | 1.760 | 0.030 |

-continued
| Cmpd No. | Structure | NCGC ID | Stability (min) | Permeability (1e-6 cm/s) | Solubility (µg/mL) | NRAS IC50 (µM) | FLT3 ITD IC50 (µM) |
|---|---|---|---|---|---|---|---|
| I-47 | 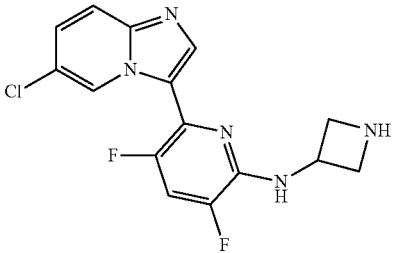 [SMILES: Fc1cc(F)c(-c2cnc3ccc(Cl)cn23)nc1NC1CNC1] | NCGC 00249846 | >30.0 | 1164.1 | >50.0 | 1.880 | 0.157 |
| I-12 | 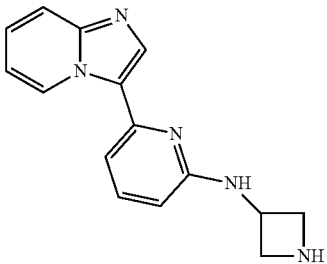 [SMILES: c1cc(NC2CNC2)nc(-c2cnc3ccccn23)c1] | NCGC 00262328 | >30.0 | <1.3 | >39.0 | | 0.260 |
| I-48 | 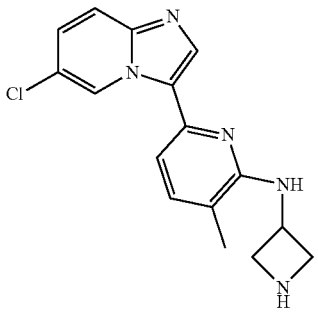 [SMILES: Cc1ccc(-c2cnc3ccc(Cl)cn23)nc1NC1CNC1] | NCGC 00262329 | 11.8 | 34.5 | >46.0 | | 2.787 |
| I-49 | 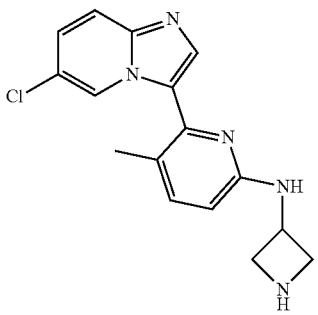 [SMILES: Cc1ccc(NC2CNC2)nc1-c1cnc2ccc(Cl)cn12] | NCGC 00262330 | 26.2 | 39.3 | >46.0 | | 0.892 |
| I-50 | 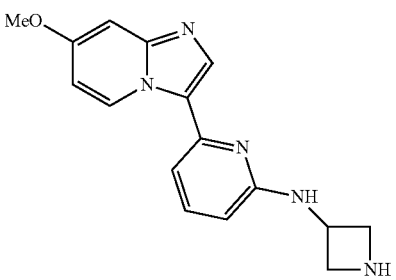 [SMILES: COc1ccn2c(-c3cccc(NC4CNC4)n3)cnc2c1] | NCGC 00249829 | >30.0 | <1.6 | >44.0 | | 0.120 |

-continued
| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-51 | 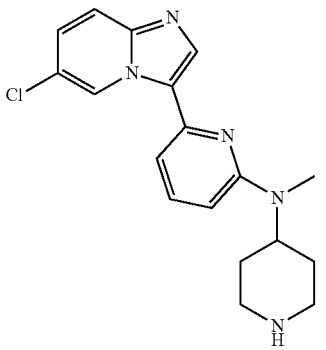 [SMILES: CN(c1cccc(-c2cnc3ccc(Cl)cn23)n1)C1CCNCC1] | NCGC 00249832 | 9.0 | >1314.0 | >50.0 | | 0.028 |
| I-52 | 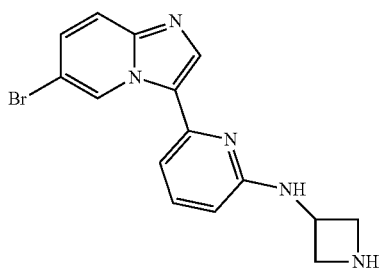 | NCGC 00249354 | 19.8 | 35.5 | 41.8 | | 0.085 |
| I-53 | 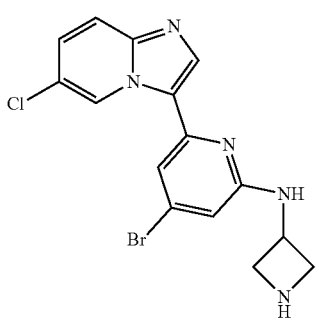 [SMILES: Clc1ccc2ncc(-c3cc(Br)cc(NC4CNC4)n3)n2c1] | NCGC 00249838 | >30.0 | <19.3 | 19.5 | | 4.956 |
| I-54 | 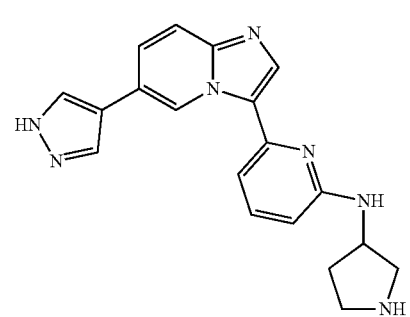 [SMILES: c1cc(NC2CCNC2)nc(-c2cnc3ccc(-c4cn[nH]c4)cn23)c1] | NCGC 00249841 | 7.6 | <1.6 | >51.0 | | 0.107 |

-continued

| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-55 | 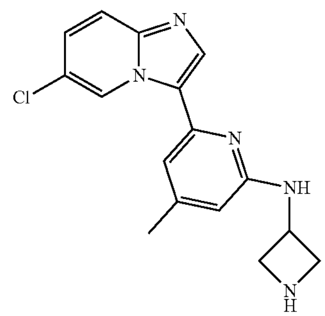 [SMILES: Cc1cc(NC2CNC2)nc(-c2cnc3ccc(Cl)cn23)c1] | NCGC 00249842 | N/A | 89.9 | >46.0 | | 0.291 |
| I-56 | 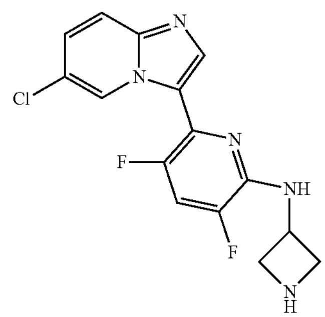 [SMILES: Fc1cc(F)c(-c2cnc3ccc(Cl)cn23)nc1NC1CNC1] | NCGC 00249846 | >30.0 | 1164.1 | >50.0 | | 0.095 |
| I-57 | 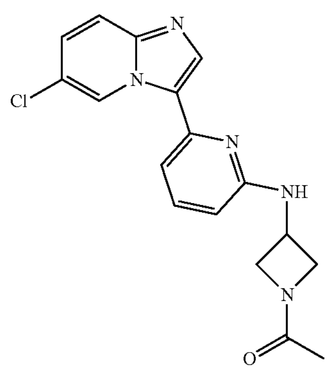 [SMILES: CC(=O)N1CC(Nc2cccc(-c3cnc4ccc(Cl)cn34)n2)C1] | NCGC 00249371 | >30.0 | 412.3 | >50.0 | | 0.399 |
| I-58 | 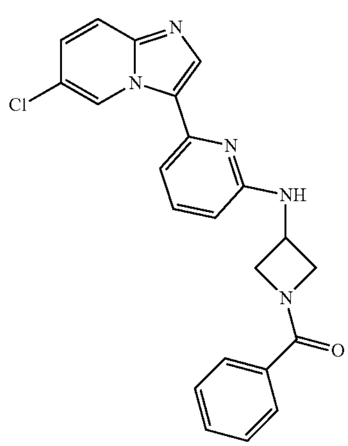 [SMILES: O=C(c1ccccc1)N1CC(Nc2cccc(-c3cnc4ccc(Cl)cn34)n2)C1] | NCGC 00249374 | 8.0 | 92.2 | <1.0 | | 0.709 |

-continued

| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-59 | 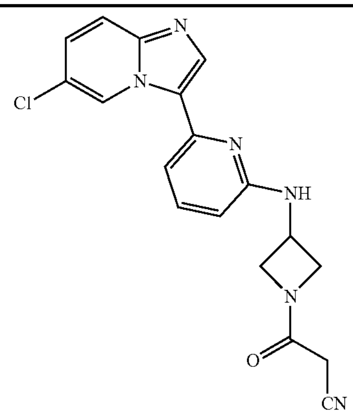 | NCGC 00249370 | >30.0 | 401.3 | 18.3 | | 0.205 |
| I-60 | 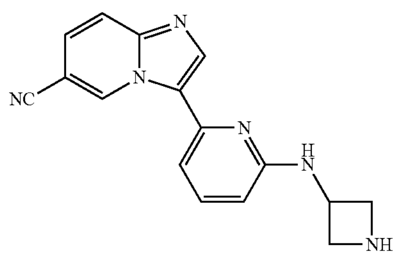 [SMILES: N#Cc1ccc2ncc(-c3cccc(NC4CNC4)n3)n2c1] | NCGC 00249366 | 16.4 | <2.3 | >43.0 | | 0.313 |
| I-17 | 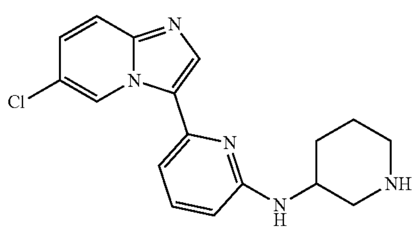 [SMILES: Clc1ccc2ncc(-c3cccc(NC4CCCNC4)n3)n2c1] | NCGC 00249373 | >30.0 | 2018.5 | >48.0 | | 0.022 |
| I-2 | 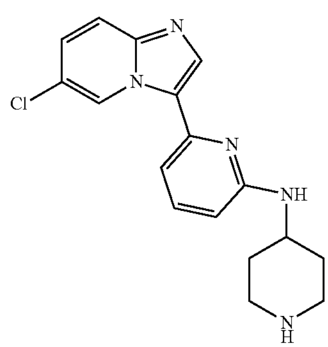 [SMILES: Clc1ccc2ncc(-c3cccc(NC4CCNCC4)n3)n2c1] | NCGC 00249350 | >30.0 | 806.9 | >48.0 | | 0.016 |
| I-61 | 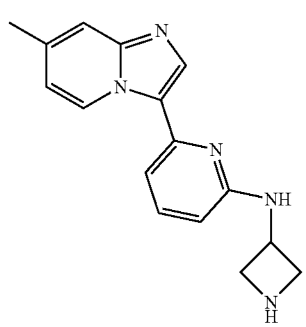 [SMILES: Cc1ccn2c(-c3cccc(NC4CNC4)n3)cnc2c1] | NCGC 00249375 | >30.0 | <3.0 | >41.0 | | 0.442 |

-continued
| Cmpd No. | Structure | NCGC ID | Stability (min) | Permeability (1e-6 cm/s) | Solubility (μg/mL) | NRAS IC50 (μM) | FLT3 ITD IC50 (μM) |
|---|---|---|---|---|---|---|---|
| I-62 | 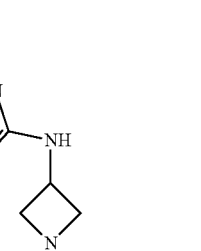 | NCGC 00249368 | >30.0 | 85.6 | 41.5 | | 0.154 |
| I-63 | 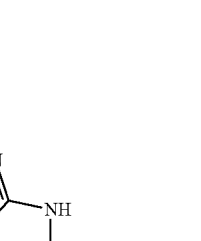 | NCGC 00249362 | N/A | 3.5 | >44.0 | | 0.973 |
| I-64 | 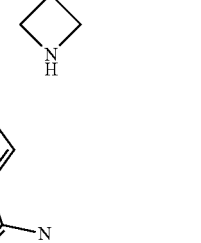 | NCGC 00249363 | N/A | <5.2 | >56.0 | | 1.998 |
| I-67 | 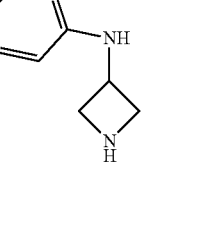 | NCGC 00249349 | >30.0 | <3.5 | >49.0 | | 0.892 |
| I-68 | 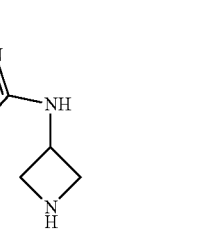 | NCGC 00378320 | 11.6 | 12.9 | >49.0 | | 0.015 |

Example Set E—Cell Data
General Methods:
The methods below are used in Example Set E, unless otherwise indicated.

Cell Culture:
MLL-AF9 FLT3-ITD and MLL-AF9 NRas cell lines were provided by Dr. James Mulloy (Cincinnati Children's Hospital Medical Center, Cincinnati, Ohio) (PMID:19277588) were cultured in Isocov's DMEM medium with 20% FBS and 1% penicillin-streptomycin. MV4;11 cell line was provided by Dr. Lee Grimes (CCHMC, Cincinnati, Ohio) were cultured in RPMI 1640 medium with 10% FBS and 1% penicillin-streptomycin. MDSL cells were provided by Dr. Kaoru Tohyama (Kawasaki Medical School, Okayama, Japan) (PMID:20130600). MDSL cells were cultured in RPMI 1640 medium with 10% FBS, 1% penicillin-streptomycin, and 10 ng/mL recombinant human Interleukin-3 (Stemcell Technologies). Human CD34+ umbilical cord blood was obtained from the Translational Research Development Support Laboratory of Cincinnati Children's Hospital under an approved Institutional Review Board protocol. These cells were maintained in StemSpan Serum-Free Expansion Media (Stemcell Techologies) supplemented with 10 ng/mL of recombinant human stem cell factor (SCF) (Stemcell Technologies), recombinant human thrombopoietin (TPO) (Stemcell Technologies), recombinant human interleukin-3 (IL-3) (Stemcell Technologies), and recombinant human interleukin-6 (IL-6) (Stemcell Technologies).

Reagents:
IRAK1/4 inhibitor (Amgen Inc.) was purchased from Sigma-Aldrich (15409). AC220 was purchased from Selleckchem.

Mice:
NRGS (NOD.Rag$^{-/-}$;yc$^{null}$; hIL-3, hGM-CSF, hSF) mice were provided by Dr. James Mulloy (Cincinnati Children's Hospital Medical Center, Cincinnati, Ohio) (PMID: 25762176).

Immunoblot:
Protein lysates were made by lysing cells in cold RIPA lysis buffer (50 mM Tris-HCl, 150 mM NaCl, 1 mM EDTA, 1% Titon X-100, and 0.1% SDS), in the presence of sodium orthovanadate, PMSF, and protease and phosphatase inhibitors. Protein concentration was quantified using BCA assay (Pierce). Protein lysates were separated by SDS-polyacrylamide gel electrophoresis (BIO-RAD), transferred to nitrocellulose membranes (BIO-RAD), and immunoblotted. The following antibodies were used for western blot analysis: GAPDH (D16H11, Cell Signaling, 1:1000 milk) FLT3 (3462, Cell Signaling, 1:1000 BSA), phospho-FLT3 (Tyr591) (3461, Cell Signaling, 1:500 BSA), IRAK4 (4363, Cell Signaling, 1:1000 BSA), phospho-IRAK4 (Thr345/Ser346) (11927, Cell Signaling, 1:500 BSA), peroxidase-conjugated AffiniPure Goat Anti-rabbit IgG (111-035-003, Jackson ImmunoResearch Laboratories, Inc., 1:10000 milk). Blots were visualized using ECL Western Blotting Substrate (Pierce) and imaged on autoradiography film (HyBlot CL) or BIO-RAD ChemiDoc Touch Imaging system.

Colony Formation:
Cells were suspended at 1000 cells/mL (MLL-AF9 FLT3-ITD, MLL-AF9 NRas, and human CD34+ cord blood) or 2000 cells/mL (MDSL) in methylcellulose (MethylCult H4434 Classic) supplemented with the indicated drug. Colonies were counted 10 days after plating.

Viability and Cell Growth:
For AnnexinV analysis cell were washed in AnnexinV Binding Buffer (eBioscience) and resuspended in AnnexinV binding buffer with AnnexinV-conjugated antibody (1:100, eBioscience). A 15-minute, room temperature incubation was followed by flow cytometric analysis. Analysis was performed using BD FACSCanto flow cytometer with Diva software. Trypan Blue (MP Biomedicals LLC) exclusion was done using an automated cell counter (BioRad TC10).

CellTiter-Glo Luminescent Viability Assay (Promega):
In a 96-well culture plate (Corning Inc. Costar), 25000 cells were plated in 200 µL media per well. In triplicate, 2 µL of the indicated inhibitor (100× in DMSO) was added to each well and cells treated with 2 µL DMSO alone was used as the control. Treated cells were incubated at 37° C. for 72 hours. In a white 96-well assay plate (Corning Inc. Costar), 100 µL of the treated cells were transferred and brought to room temperature. An equal volume of CellTiter-Glo Reagent at room temperature was added to the cells and the plate was rocked for 2 minutes, followed by 10 minutes of rest. Analysis was performed using GloMax 96 microplate Luminometer (Promega) with GloMax Software.

AlphaLISA Assay:
AlphaScreen SureFire STAT5 (pTyr694;Tyr699) Assay kit (Perkin Elmer). Assay was performed according to manufacturer protocol.

Figure 2:
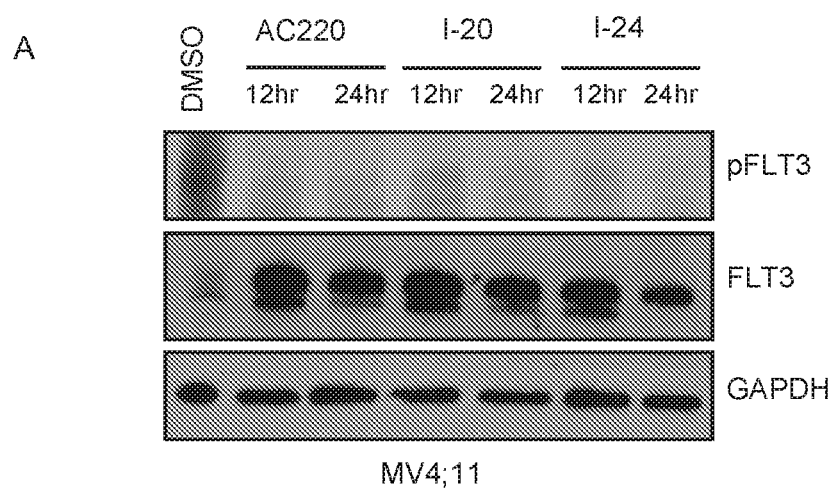
FIG. 2: Some compounds of Formula (I) can suppress activation of FLT3.
Figure 2:
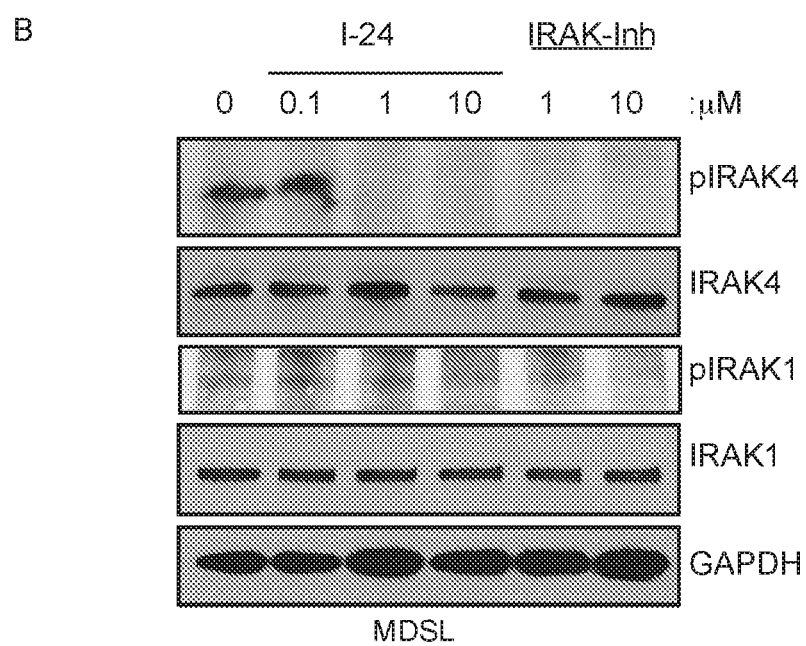
Figure 2:
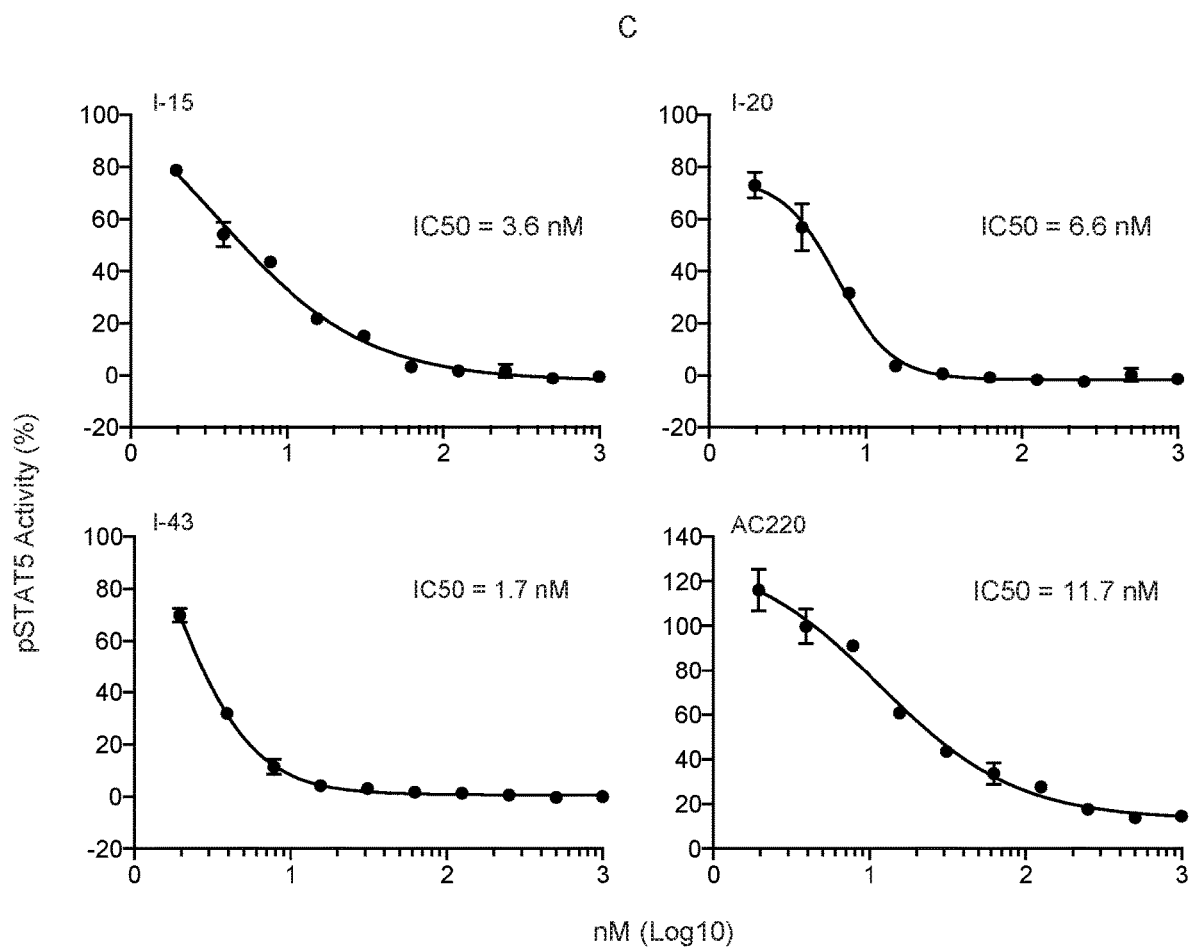

FIG. 2—Methods: Some compounds of Formula (I) can suppress activation of FLT3. (FIG. 2A) Immunoblot analysis of MV4;11 cells (a human FLT3-ITD-AML cell line) treated with AC220 (50 nM), compound I-20 (50 nM), or compound I-24 (50 nM) for 12 or 24 hours. (FIG. 2B) Immunoblot analysis of MDSL cells (a human MDS line with high basal levels of P-IRAK4) treated with the indicated concentrations of compound I-24 or IRAK-Inh (Amgen; CAS Reg. No. 509093-47-4) for 24 hours. (FIG. 2C) Phospho (P)—STAT5 activity was measured by AlphaLISA assay in MV4;eleven cells treated with the indicated concentrations of I-15, I-20, I-43, or AC220 for 5 hours.

FIG. 2—Results & Discussion: Some compounds of Formula (I) can suppress activation of FLT3. To assess the ability of the compounds to inhibit FLT3 activity in relevant human cells, we treated MV4; eleven cells (a human FLT3-ITD-AML cell line) with AC220, compound I-20, or compound I-24 at 50 nM for 24 hours and evaluated phosphorylated (P)-FLT3 by immunoblotting (FIG. 2A). Compound I-20 and compound I-24 inhibited FLT3 phosphorylation comparably to AC220. MV4; eleven cells exhibit low basal levels of IRAK4 phosphorylation, therefore we chose MDSL cells (a human MDS line with high basal levels of P-IRAK4) to examine the activity of compound I-24 on IRAK4 phosphorylation. Compound I-24 treatment of MDSL cells effectively inhibited pIRAK4, and was comparable to IRAK-Inh (FIG. 2B). To determine inhibition of downstream FLT3 signaling, MV4; eleven cells were treated with compound I-15, compound I-20, compound I-43, or AC220 for 5 hours and P-STAT5 activity was measured by AlphaLISA (FIG. 2C). All three compounds inhibit STAT5 phosphorylation equivalent to or slightly better than inhibition by AC220 (IC50=1.7, 3.6, and 6.6 nM versus 11.7 nM for AC220). These results show that compound I-15, compound I-20, compound I-43 are just as effective at inhibiting FLT3 phosphorylation and downstream signaling as AC220 and additionally, can inhibit IRAK1/4 phosphorylation.

Figure 3:
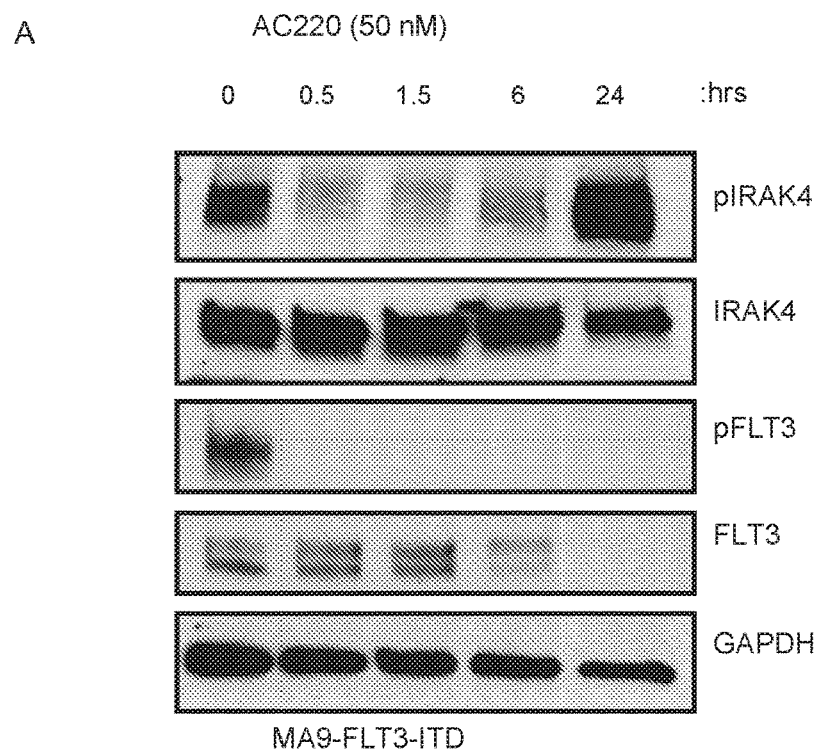
FIG. 3: FLT3 inhibition can result in a compensatory activation of IRAK1/4 in FLT3-ITD AML.
Figure 3:
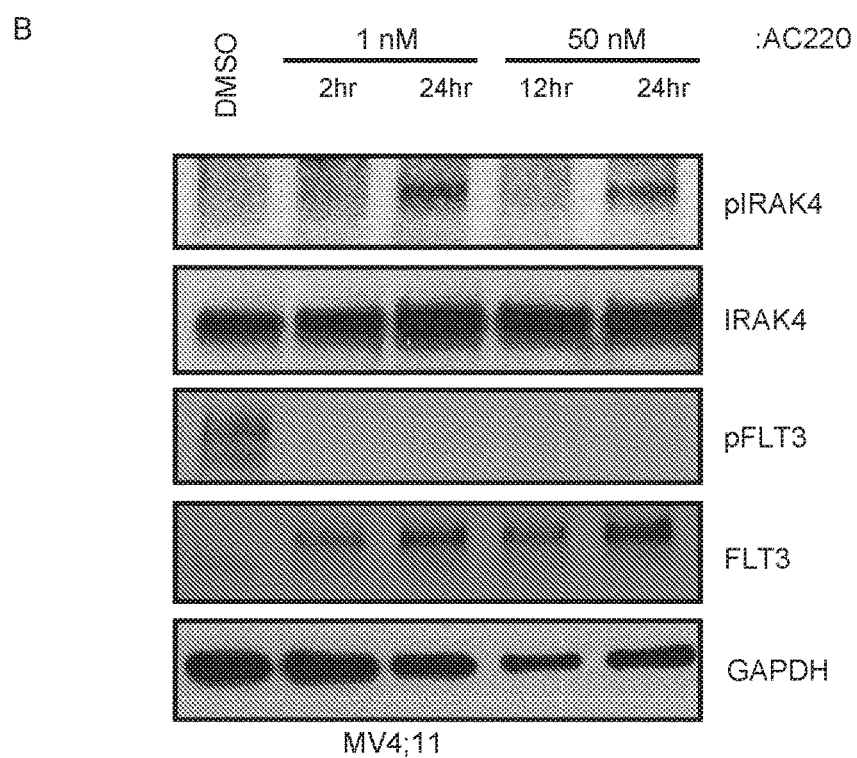
Figure 3:
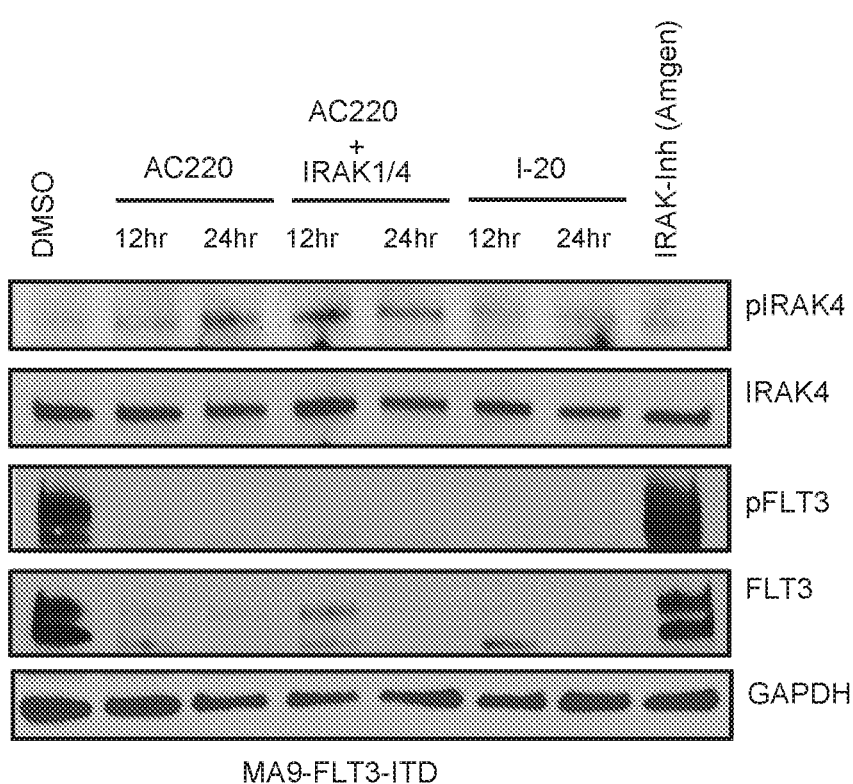
Figure 3:
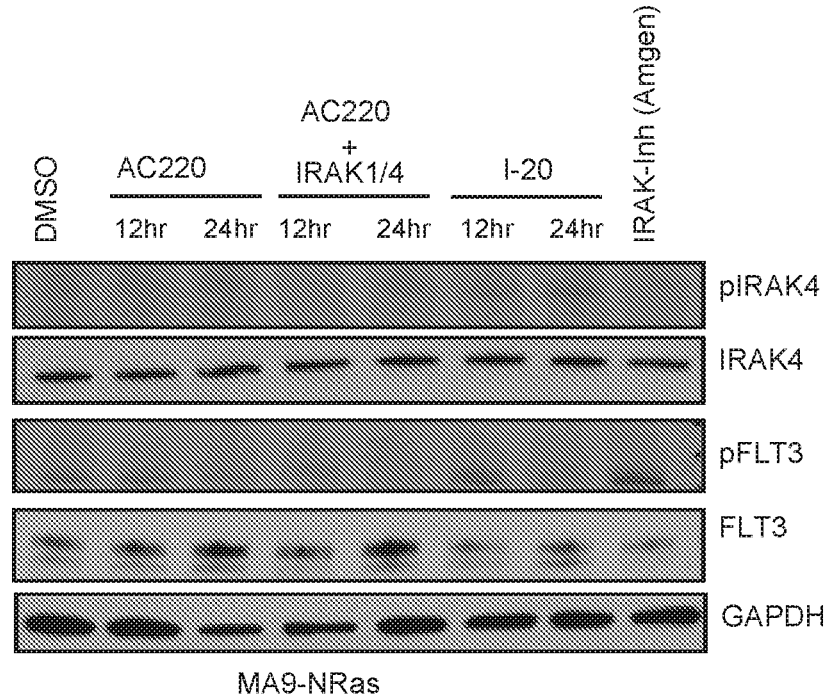

FIG. 3—Methods: FLT3 inhibition results in a compensatory activation of IRAK1/4 in FLT3-ITD AML. (FIG. 3A) Immunoblot analysis of human cord blood CD34+ cells transduced with MLL-AF9 and FLT3-ITD (MA9-FLT3-ITD) treated with AC220 (50 nM) for the indicated times. (FIG. 3B) Immunoblot analysis of MV4; eleven cells treated with AC220 (1 or 50 nM) for the indicated times. (FIG. 3C) Immunoblot analysis MA9-FLT3-ITD treated with AC220

(50 nM), AC220 (50 nM) and IRAK-Inh (10 µM), compound I-20 (50 nM), or IRAK-Inh alone (10 µM). (FIG. 3D) Immunoblot analysis of human cord blood CD34+ cells transduced with MLL-AF9 and Nras (MA9-NRas) treated with AC220 (50 nM), AC220 (50 nM) and IRAK-Inh (10 µM), compound I-20 (50 nM), or IRAK-Inh alone (10 µM).

FIG. 3—Results & Discussion: FLT3 inhibition results in a compensatory activation of IRAK1/4 in FLT3-ITD AML. When FLT3-ITD AML cells are treated with AC220, P-IRAK4 levels increase after 24 hour exposure to AC220. The compensatory phosphorylation of IRAK4 is observed across several FLT3-ITD AML cell lines, and even at AC220 concentrations as low as 1 nM (FIGS. 3A-C). An increase in P-IRAK4 was not observed in AML cells with wild-type FLT3 (FIG. 3D). Compound I-20 did not result in compensatory phosphorylation of IRAK4 (FIG. 3C). Without being bound by theory, these data might suggest that IRAK signaling could act as a compensatory pathway for FLT3-dependent AML cells to survive FLT3 inhibition and that the compounds of Formula (I) are able to inhibit this response.

Figure 4:
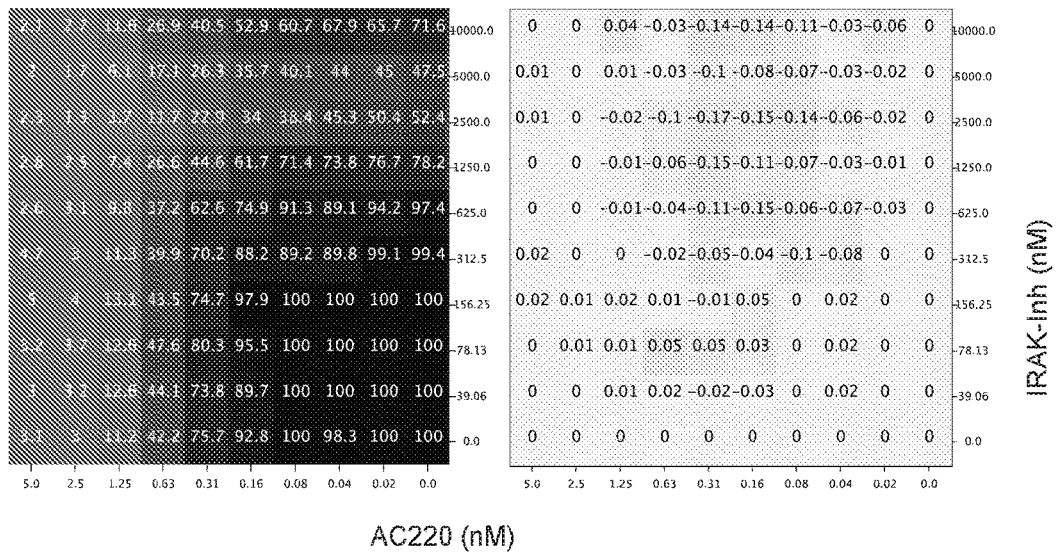
FIG. 4: Synergistic inhibition of FLT3-ITD AML with FLT3 and IRAK1/4 inhibitors.
Figure 4:
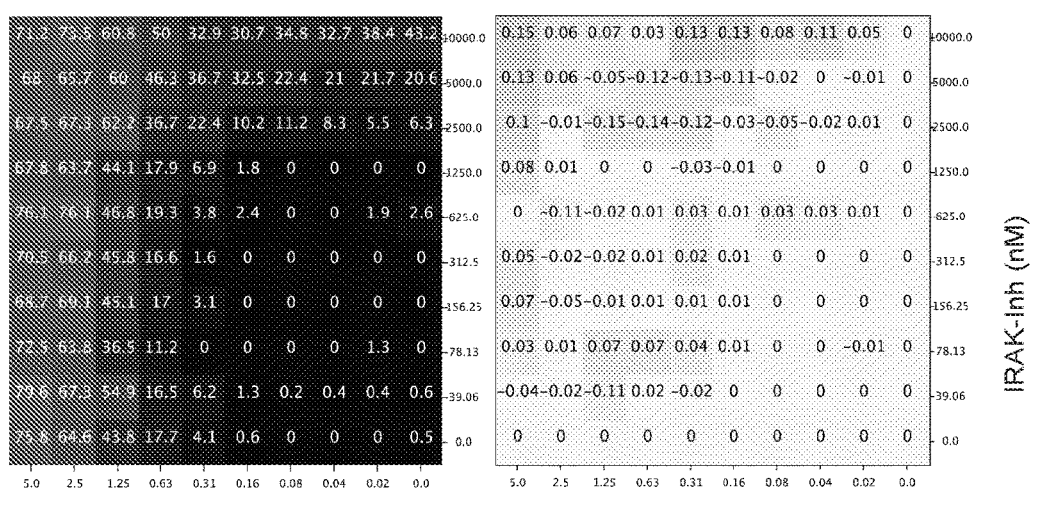
Figure 4:
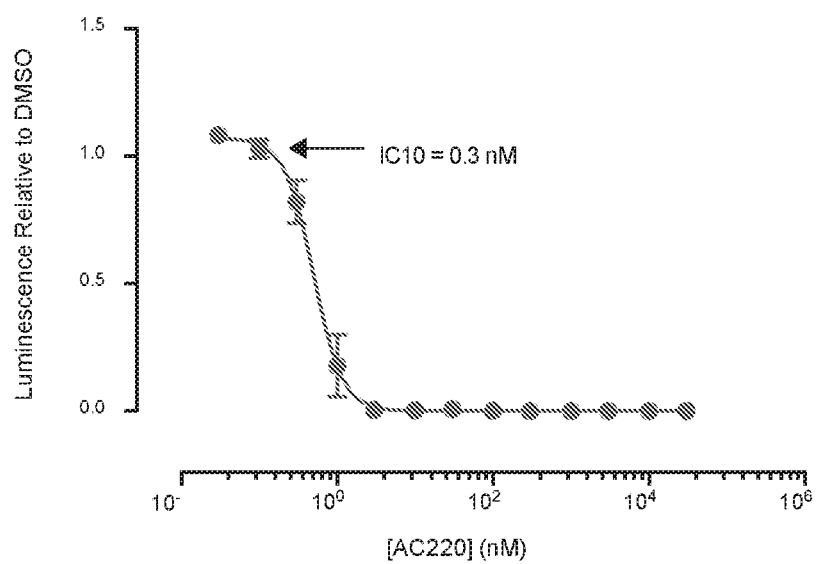
Figure 4:
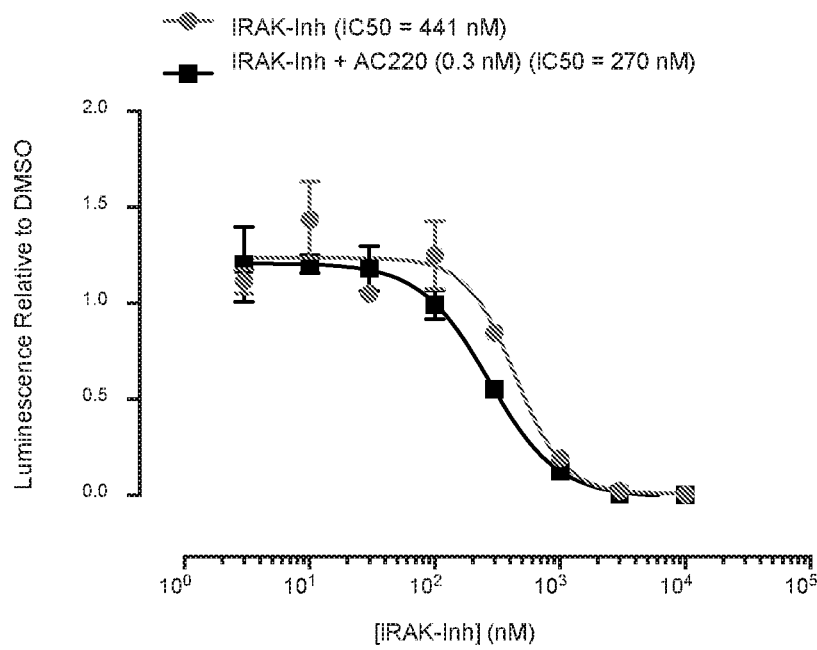

FIG. 4—Methods: Inhibition of FLT3-ITD AML. (FIGS. 4A-4B) Heatmap response profile (left panel) and Delta Bliss analysis (right panel) for AC220 and IRAK-Inh (Amgen) combination treatment of MA9-FLT3-ITD cells. (FIG. 4A) Cell-titer glow (CTG) percent response values represent normalized growth, relative to controls based on SybrGreen fluorescence intensities. (FIG. 4B) Caspase activation values, relative to controls based on caspase-glo fluorescence intensities. (FIG. 4C) The IC10 of AC220 was established in MA9-FLT3-ITD cells after 48 hour treatment using cell-titer glow relative response values normalized to growth compared to control cells (DMSO). (D) MA9-FLT3-ITD cells were treated with IRAK-Inh (Amgen) alone or in combination with 0.3 nM of AC220 (IC10) for 72 hours. Cell-titer glow relative response values represent normalized growth compared to control cells (DMSO). Further details of these methods can be found in Mathews Griner et al., "High-throughput combinatorial screening identifies drugs that cooperate with ibrutinib to kill activated B-cell-like diffuse large B-cell lymphoma cells" (2014) PNAS, Vol. 111, No. 6, pp. 2349-2354.

FIG. 4—Results & Discussion: Inhibition of FLT3-ITD AML. To assess whether inhibition of FLT3 and IRAK4 can suppress FLT3-ITD AML cells, we performed a drug matrix analysis. A score of less than −1 suggests synergy between two compounds. The analysis with AC220 and a commercially-available selective IRAK1/4 compound indicated that FLT3 and IRAK signaling inhibition synergize to inhibit proliferation (−2.77 as determined by cell-titer glow) and viability (−1.63 as determined by caspase 8 cleavage) of FLT3-ITD AML (FIGS. 4A-B). To confirm the observed synergy, we evaluated proliferation of MA9 FLT3-ITD cells in the presence of AC220 (0.3 nM=IC50, FIG. 4C) and increasing concentrations of the IRAK1/4 inhibitor (FIG. 4D). Consistent with the matrix analysis, treatment of FLT3-ITD AML cells with a FLT3 inhibitor and IRAK1/4 inhibitor results in a synergistic inhibitory effect. Without being bound by theory, synergism between FLT3 and IRAK inhibition might suggest that simultaneous inhibition of these pathways would be an effective therapeutic strategy for FLT3-ITD AML.

Figure 5:
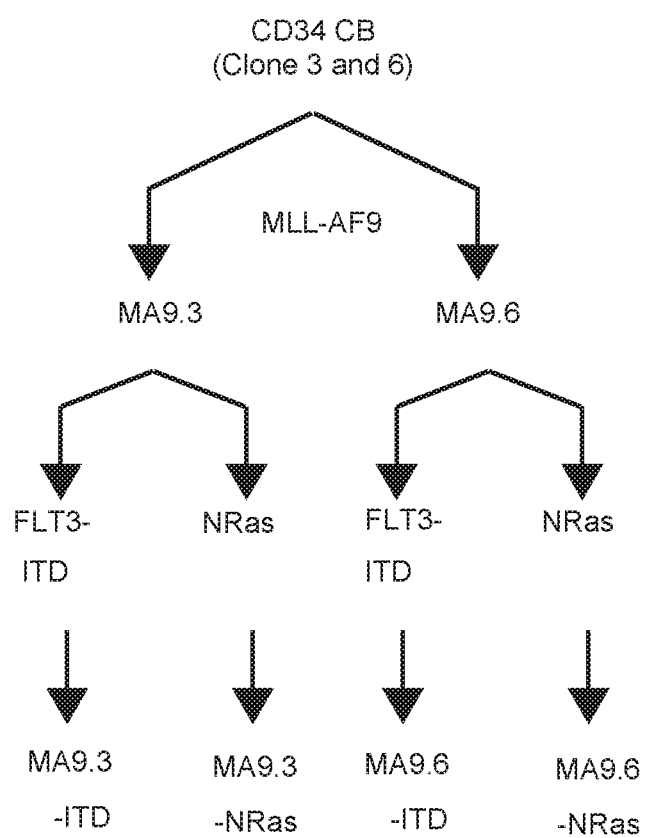
FIG. 5: Some compounds of Formula (I) can suppress FLT3-ITD AML.
Figure 5:
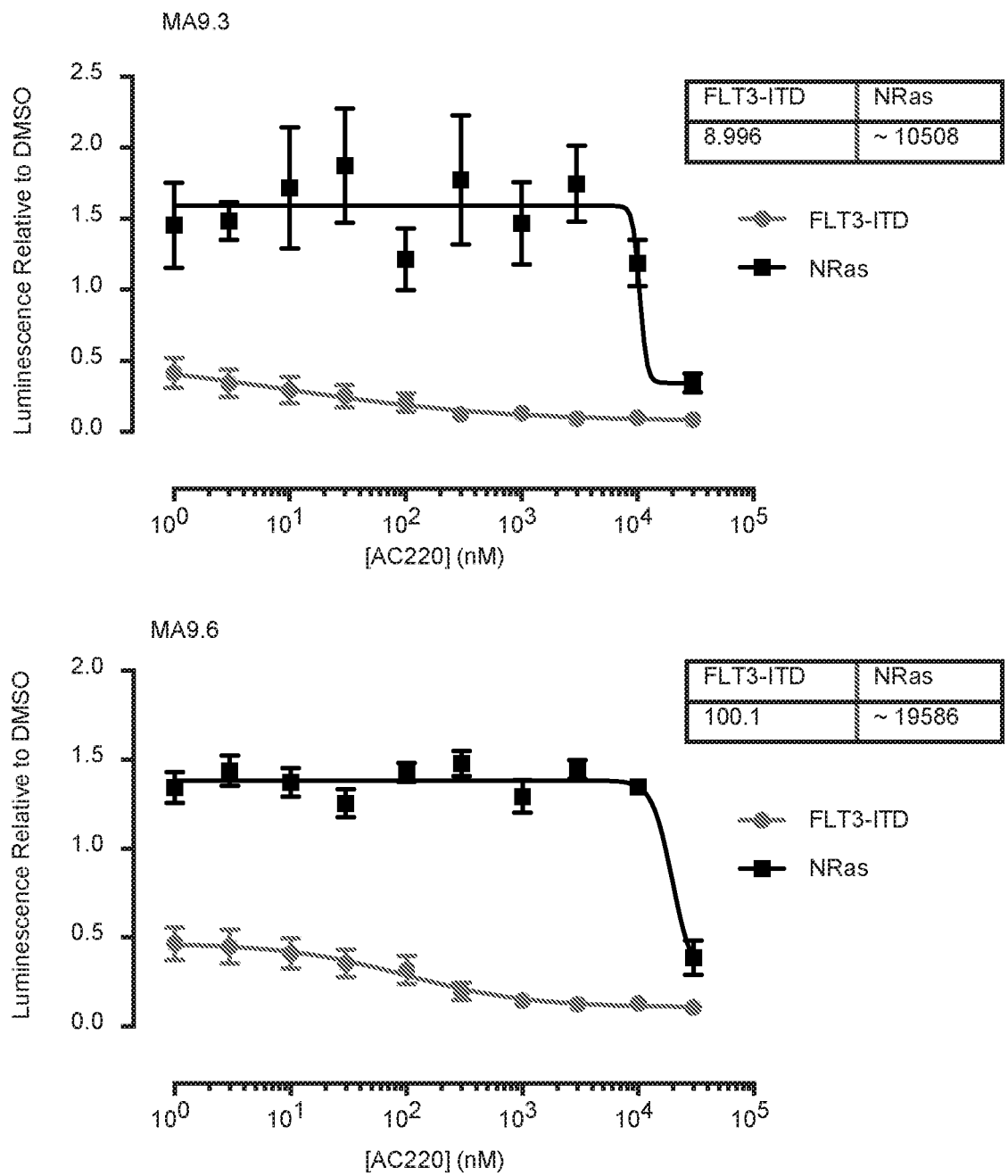
Figure 5:
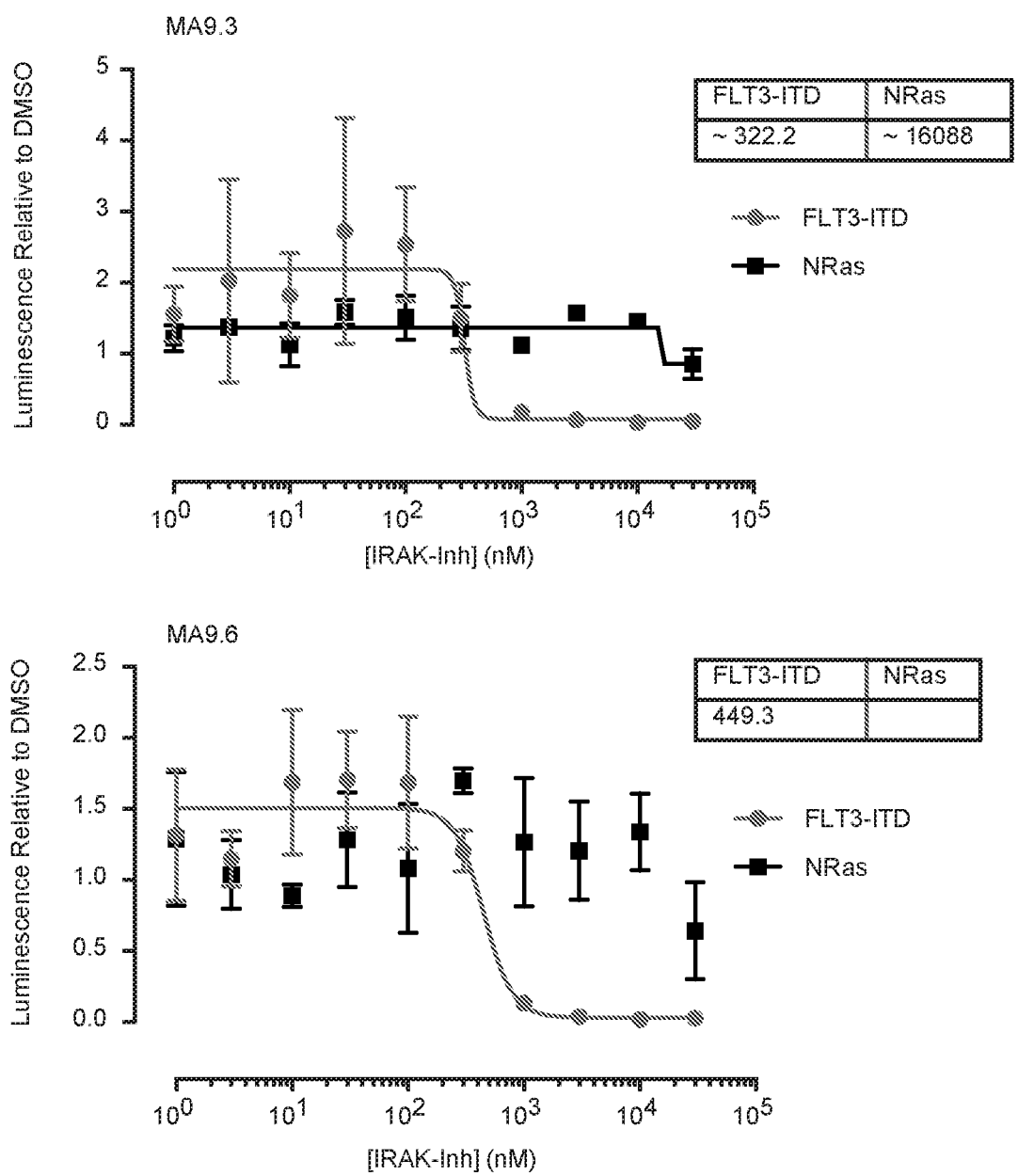
Figure 5:
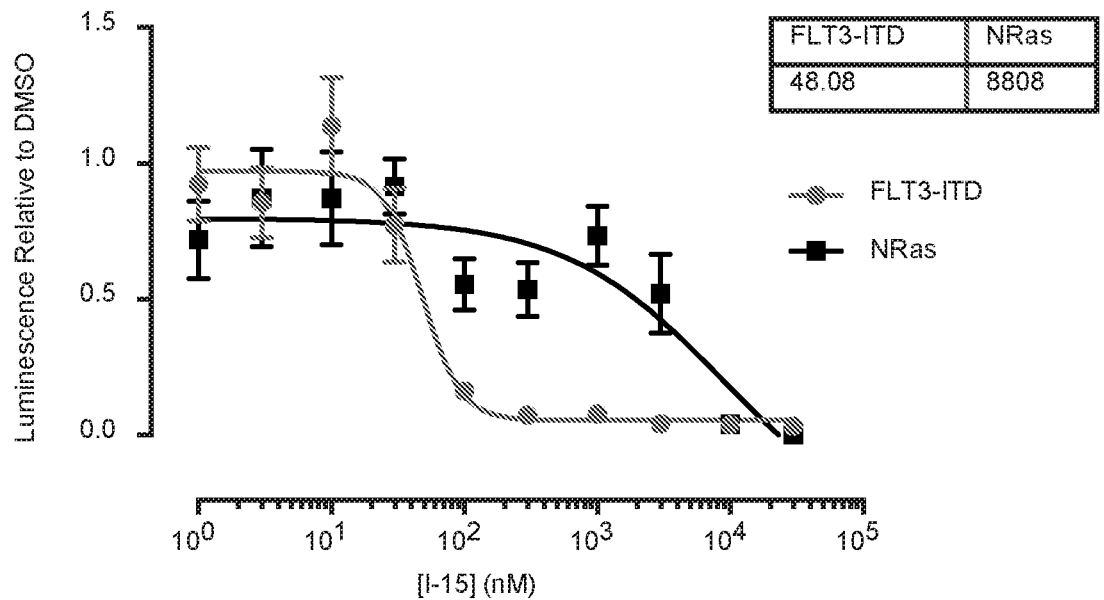
Figure 5:
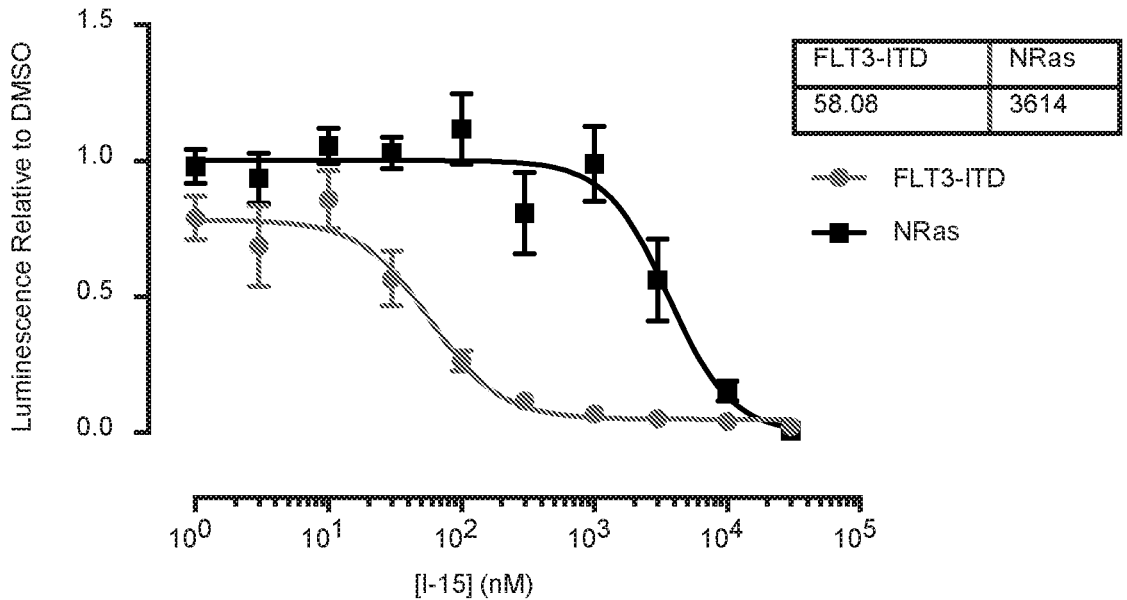
Figure 5:
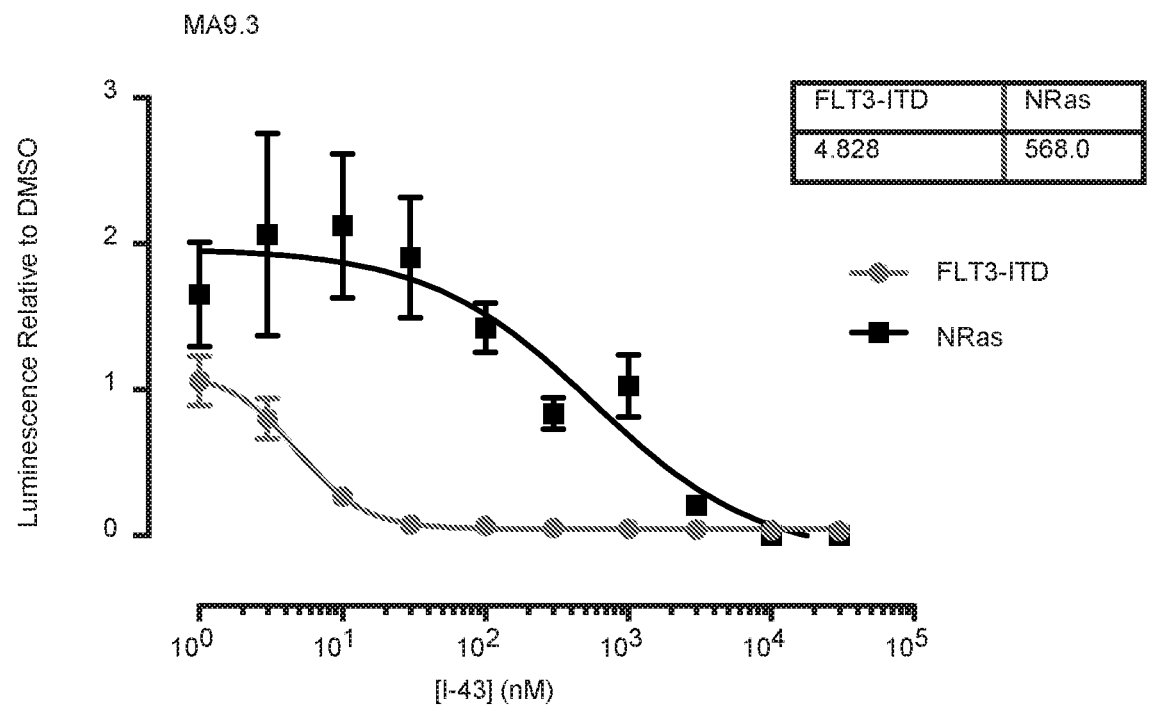
Figure 5:
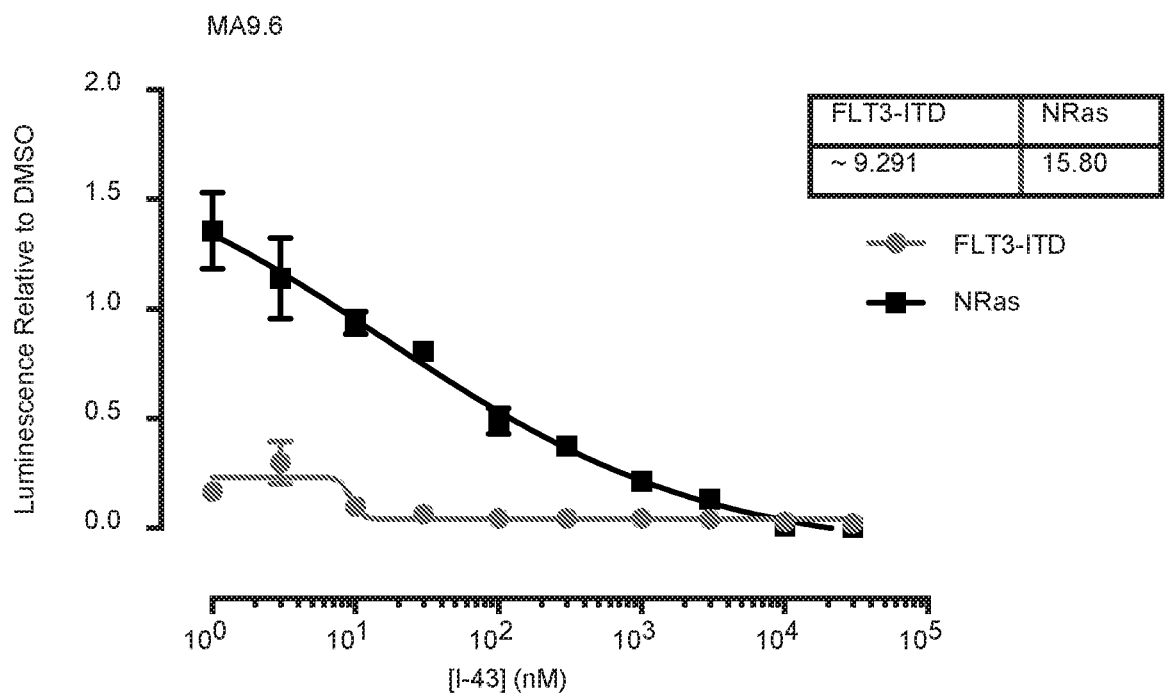
Figure 5:
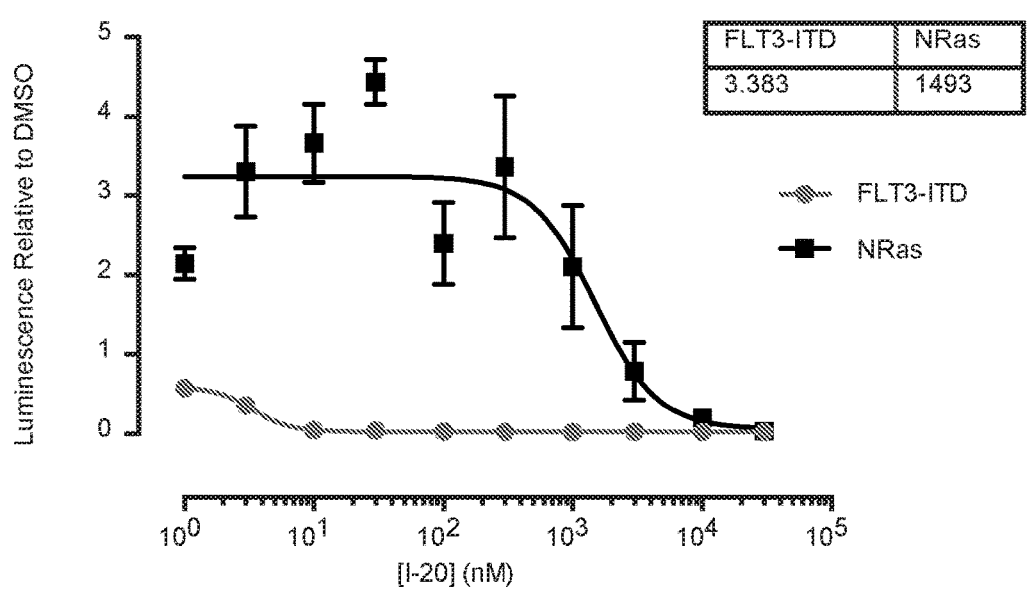
Figure 5:
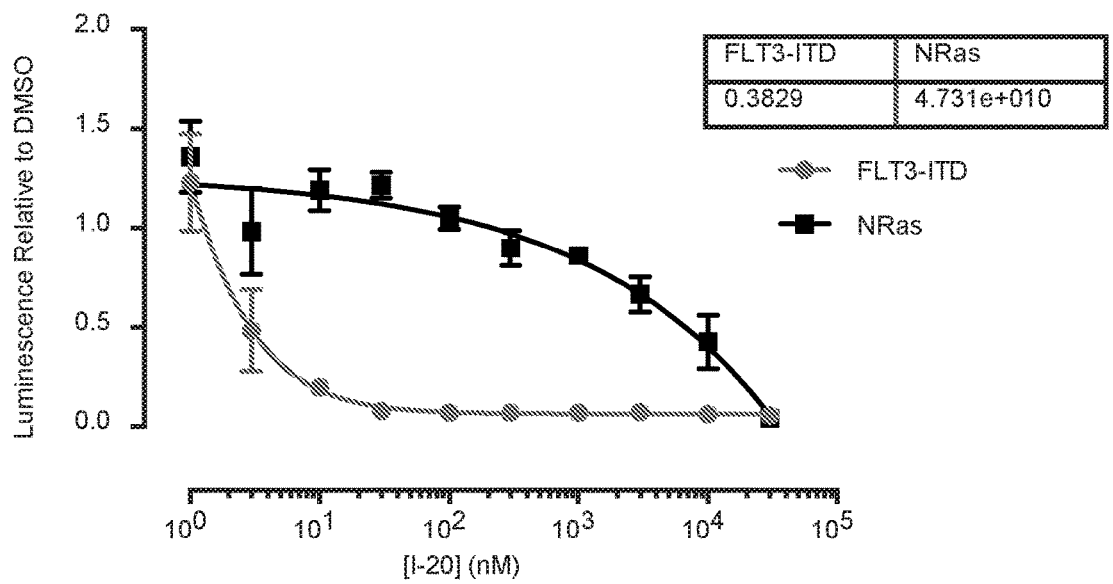
Figure 5:
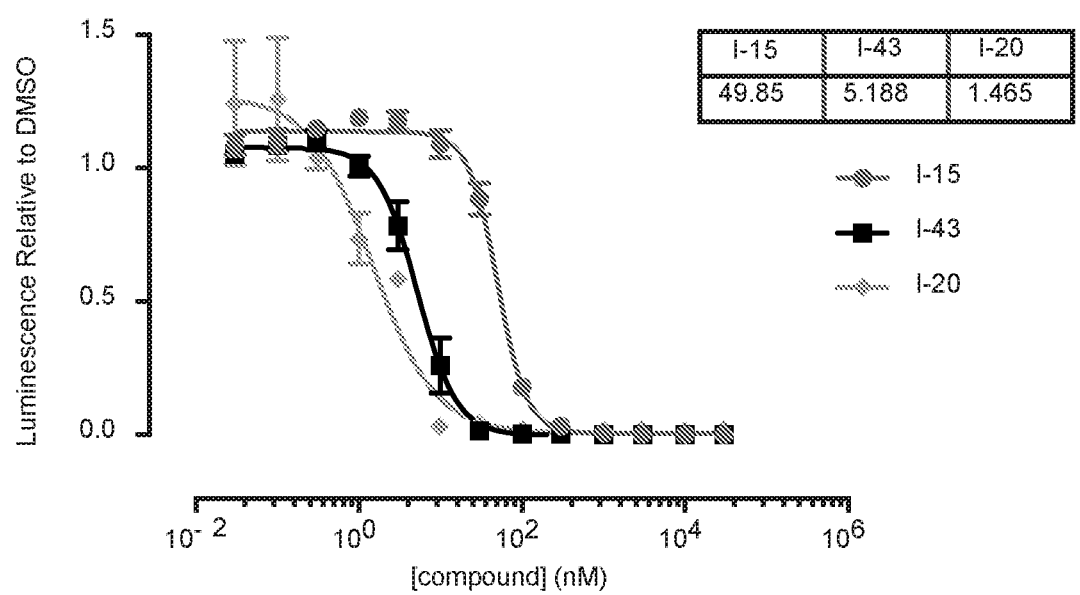
Figure 6:
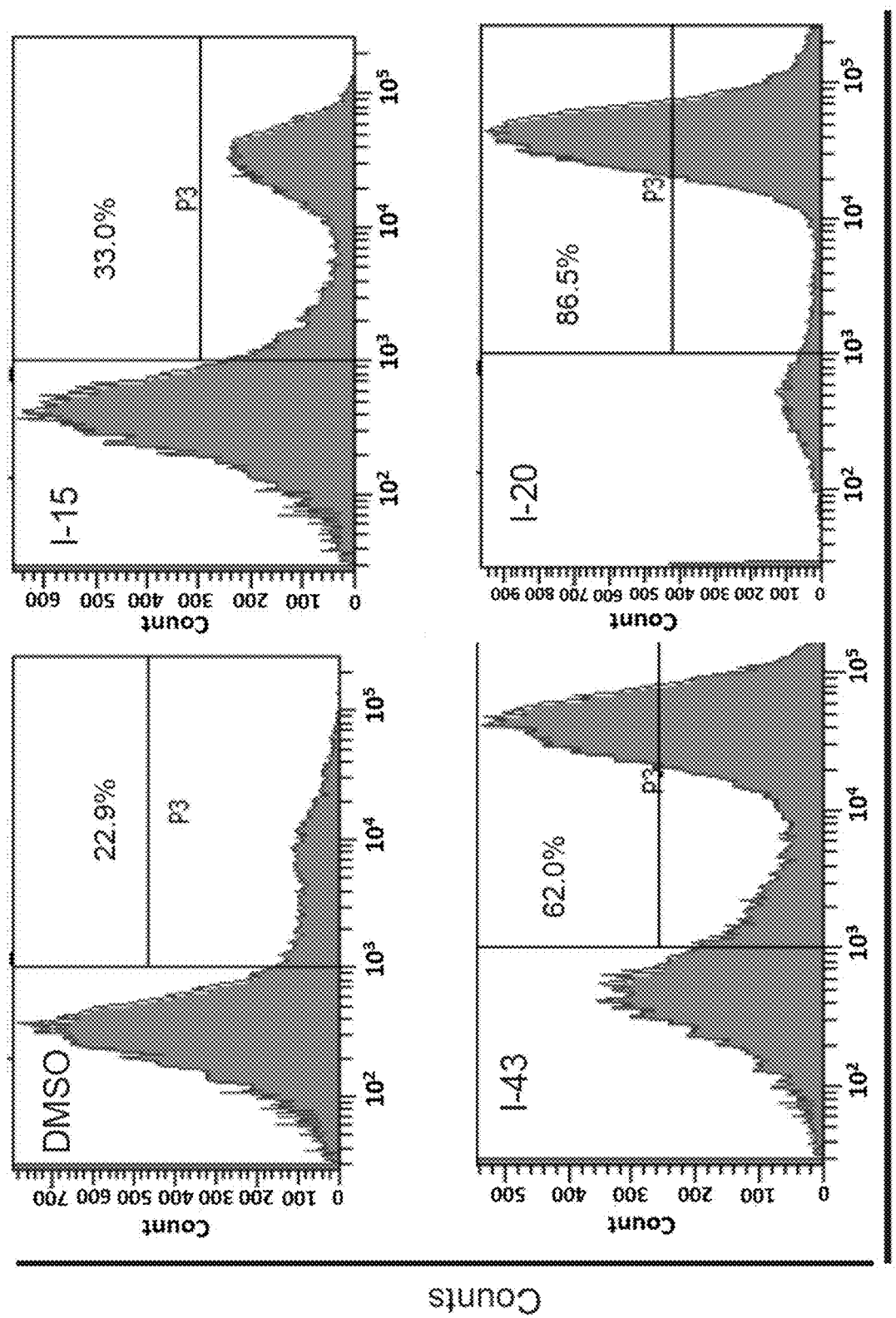
FIG. 6: Some compounds of Formula (I) can suppress FLT3-ITD AML. Cell viability was determined in MLL-AF9/FLT3-ITD cells treated with compound I-15 (1 μM), compound I-43 (1 μM), or compound I-20 (1 μM) for 72 hours by flow cytometric analysis of AnnexinV.

FIGS. 5-6—Methods: Some compounds of Formula (I) can suppress FLT3-ITD AML. (FIG. 5A) Generation of two independent clones (#3 and #6) derived from human cord blood CD34+ cells transduced with MLL-AF9 and then either FLT3-ITD (MA9-FLT3-ITD) or NRas (MA9-NRas). (FIGS. 5B-G) MA9.3 or MA9.6 clones expressing FLT3-ITD or NRas were treated with the indicated compounds for 72 hours. Cell-titer glow relative response values represent normalized growth compared to control cells (DMSO) based on luminescence intensities. Cellular IC50 values (nM) are shown for each experiment. In FIG. 6, cell viability was determined in MA9-FLT3-ITD cells treated with compound I-15 (1 µM), compound I-20 (1 µM), or compound I-43 (1 µM) for 72 hours by flow cytometric analysis of AnnexinV. Further details of these methods can be found in Mathews Griner et al., "High-throughput combinatorial screening identifies drugs that cooperate with ibrutinib to kill activated B-cell-like diffuse large B-cell lymphoma cells" (2014) PNAS, Vol. 111, No. 6, pp. 2349-2354.

FIGS. 5-6—Results & Discussion: Some compounds of Formula (I) can suppress FLT3-ITD AML. To assess the selectivity of the inhibitors to FLT3-ITD AML, we used FLT3-ITD-containing and NRAS-containing AML cells created from isogenic human CD34+ MLL-AF9 parental cells (FIG. 5A). Analysis of proliferation via CellTiter Glo revealed that FLT3-ITD AML cells are more sensitive to all of the compounds tested as compared to NRAS AML cells (FIGS. 5B-F). Therefore, these compounds appear to be selective for FLT3-ITD positive cells, rather than broadly cytotoxic, and are equivalently effective against two independent clones of MLL-AF9 AML. Additionally, the efficacy of compounds I-15, I-20, and I-43 at inhibiting AML cell growth (FIG. 5G) and viability (FIG. 6) correlated with the relative potency IRAK1/4 inhibition (FIG. 5G). Without being bound by theory, the correlation between the degree of IRAK1/4 inhibition and cell growth inhibition might suggest that the inhibitors' activity against IRAK1/4 is a contributor to the efficacy of the inhibitors.

Figure 7:
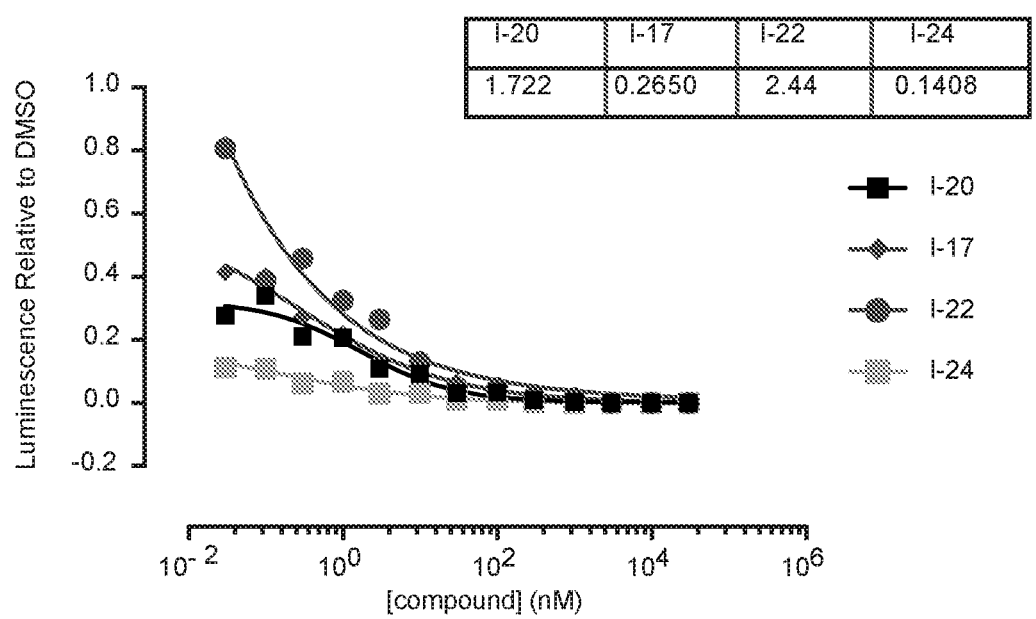
FIG. 7: Cell studies using compound I-20, compound I-17, compound I-22, and compound I-24.
Figure 7:
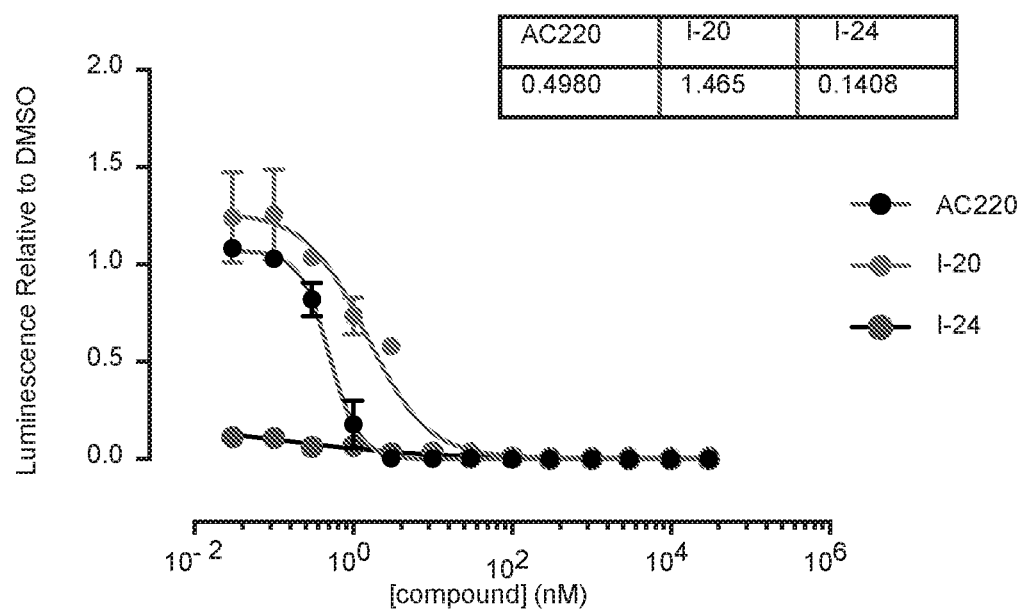
Figure 7:
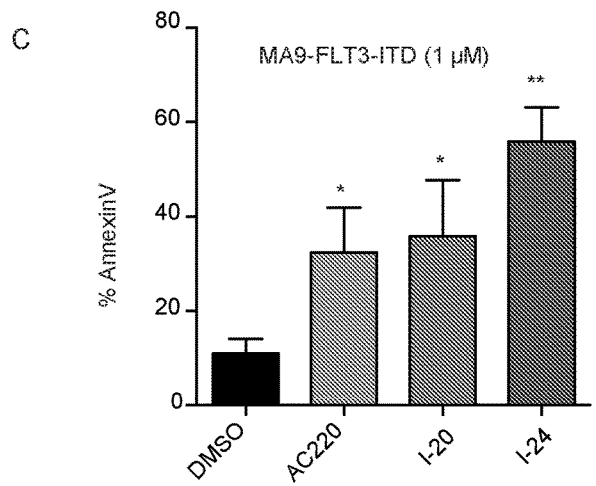
Figure 7:
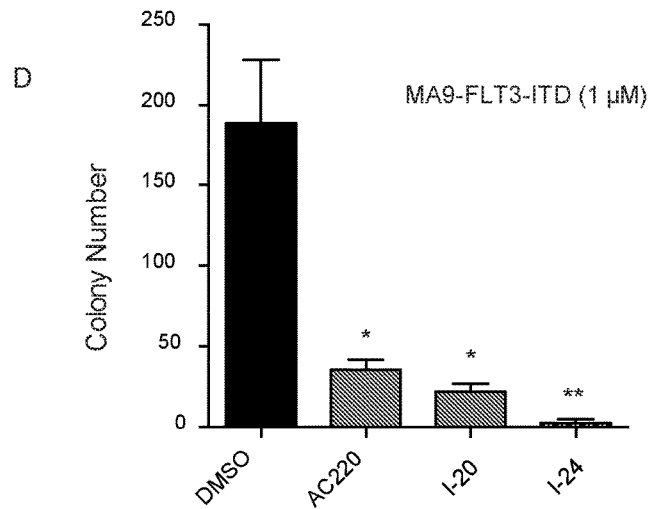
Figure 7:
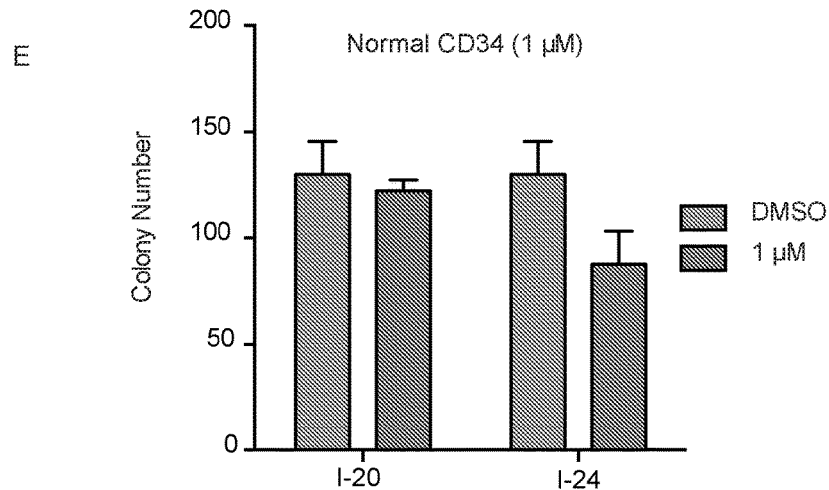

FIG. 7—Methods: (FIGS. 7A-B) MA9-FLT3-ITD cells were treated with the indicated compounds for 72 hours. Cell-titer glow relative response values represent normalized growth compared to control cells (DMSO) based on luminescence intensities. Cellular IC50 values (nM) are shown for each experiment. (FIG. 7C) Cell viability was determined in MA9-FLT3-ITD cells treated with 1 µM of the indicated compounds for 72 hours by flow cytometric analysis of AnnexinV. (FIG. 7D) Leukemic colony formation of MA9-FLT3-ITD cells was determined in methylcellulose supplemented with 1 µM of the indicated compounds. Colony formation was determined after 10 days. (FIG. 7E) Colony formation of normal cord blood CD34+ cells was determined in methylcellulose supplemented with 1 µM of the indicated compounds. Colony formation was determined after 10 days.

FIG. 7—Results & Discussion: Compounds I-17, I-22, and I-24 had subnanomolar activity against FLT3-ITD cells. In particular, compound I-24 exhibited increased potency at inhibiting cell growth, at inducing apoptosis and at inhibiting leukemic colony formation, as compared to compound I-20 and AC220 (FIGS. 7A-D). Compound I-24 inhibited colony formation of normal CD34+ cells (FIG. 7E).

Figure 8:
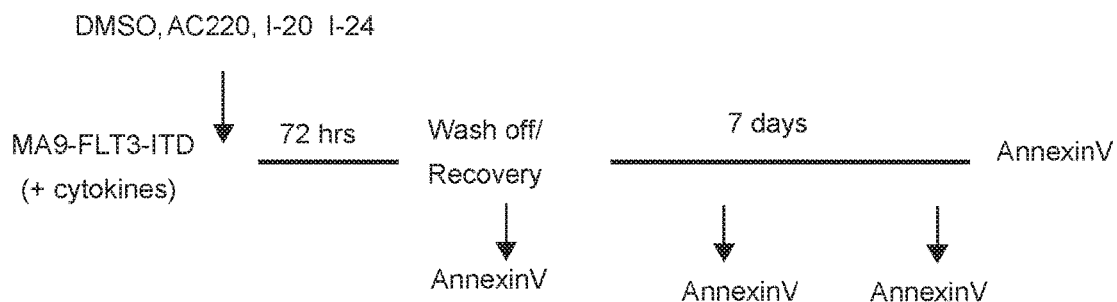
FIG. 8: Some compounds of Formula (I) can prevent emergence of resistant FLT3-ITD AML.
Figure 8:
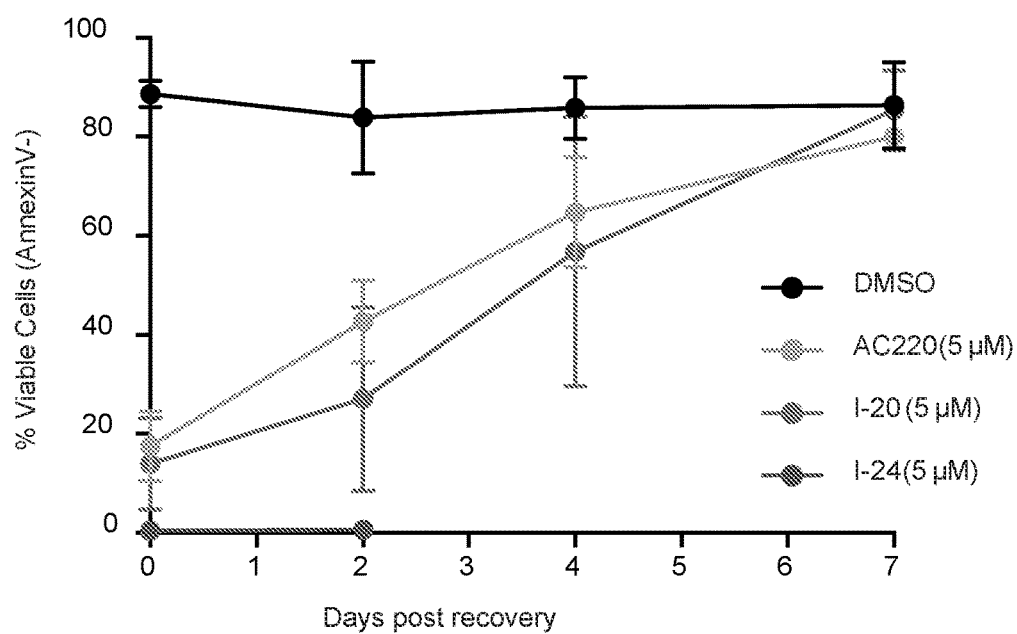
Figure 8:
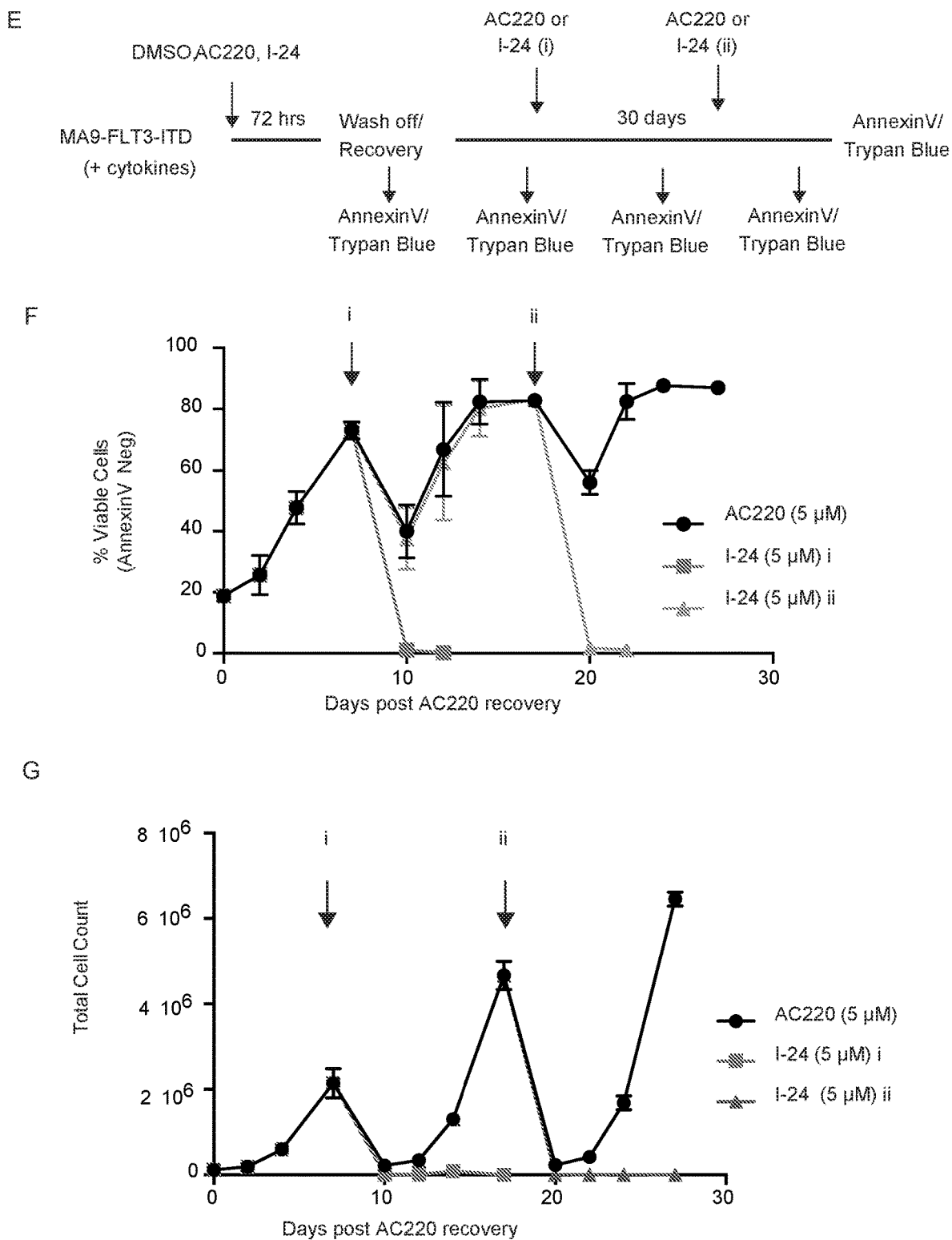

FIG. 8—Methods: (FIG. 8A) Overview of experimental design: MA9-FLT3-ITD cells were cultured in cytokines and then treated with AC220 or compound I-20 (1, 2.5, or 5 µM) for 72 hours. Cell viability was assessed by AnnexinV staining. The remaining cells were washed and replated in fresh media with cytokines. Recovery of MA9-FLT3-ITD cell growth was determined after 7 days by AnnexinV staining or Trypan Blue exclusion. (FIG. 8B) Cell viability was determined in MA9-FLT3-ITD cells after 72 hours following treatment with the indicated compounds, or after 7 days of recovery. (FIG. 8C) Overview of experimental design: MA9-FLT3-ITD cells were cultured in cytokines and then treated with AC220, compound I-20, or compound I-24 (5 μM) for 72 hours. Cell viability was assessed by AnnexinV staining. The remaining cells were washed and replated in fresh media with cytokines. Recovery of MA9-FLT3-ITD cell growth was monitored every 2 days by AnnexinV staining. (FIG. 8D) Cell viability was determined in MA9-FLT3-ITD cells after 72 hours following treatment (Day 0) with the indicated compounds, or every 2 dayspost recovery by AnnexinV staining. Compound I-24-treated cells were not monitored past Day 2 as no viable cells remained. (FIG. 8E) Overview of experimental design: MA9-FLT3-ITD cells were cultured in cytokines and then treated with AC220 or compound I-24 (5 μM) for 72 hours. Cell viability was assessed by AnnexinV staining. The remaining cells were washed and replated in fresh media with cytokines. After AC220-treated cells recovered (Day 7), they were subsequently treated with AC220 (5 μM) or compound I-24 (5 μM) ("i") and monitored every 2 days by AnnexinV staining. This step was repeated once more at Day 16 ("ii"). (FIGS. 8F-G) Cell viability was determined in MA9-FLT3-ITD cells after 72 hours following treatment (Day 0) with the indicated compounds, or every 2 days post recovery by AnnexinV staining (FIG. 8F) or Trypan Blue exclusion (FIG. 8G).

FIG. 8—Results & Discussion: Some compounds of Formula (I) can prevent emergence of resistant FLT3-ITD AML. AML relapse is a clinical problem following FLT3 inhibitor treatment. Therefore, we assessed AML cells recovery and emergence of resistant cells after AC220 treatment in vitro. To permit emergence of resistant AML cells and better recapitulate the cytokine conditions in vivo, we cultured MA9 FLT3-ITD cells in the presence of the cytokines (IL-3, IL-6, Stem Cell Factor (SCF), FL, and thrombopoietin (TPO) at 10 ng/mL). The AML cells were treated with AC220 or compound I-20 at 1 μM, 2.5 μM, or 5 μM for 72 hours. After initial treatment with the inhibitors, the cells were washed and replated in fresh media containing cytokines (day 0). Viability was assessed by AnnexinV staining following 7 days of recovery (FIG. 8A). While AC220-treated cells showed increased viability by 7 days, compound I-20-treated cells remained apoptotic, particularly at the higher doses (FIG. 8B). To evaluate the kinetics of this recovery, we evaluated viability on days 2 and 4 after washing (FIG. 8C). Viability of the AML cells with 5 μM AC220 treatment results in 15-20% viability (day 0). However after removal of the compounds, the AC220-treated cells reached 50% viability at day 2.7, while compound I-20-treated cells didn't reach 50% viability until day 3.4 (FIG. 8D). Thus, compound I-20 treatment appeared to reduce AML cell emergence after treatment. And compound I-24-treated cells did not recover. To determine whether AC220-resistant FLT3-ITD AML cells remained sensitive to compound I-24, we treated cells with AC220 (5 μM) for 72 hours, washed the cells, replated in fresh media, and monitored viability and cell number as described above. Once the cells recovered on day 7, we treated them with either AC220 or compound I-24 (5 μM) for 72 hours and then allowed them to recover for 7 days (FIGS. 8E-F). Upon the second exposure to AC220, the cells were less sensitive, with viability increasing from 20% to 35% after the first exposure. However, these cells remained sensitive to compound I-24 (FIGS. 8E-F). This pattern was repeated upon a third exposure to AC220, with viability after treatment rising to 55% while resistance to compound I-24 after two rounds of AC220 treatment was not observed. Sequencing of the TK domain of FLT3 in the cells that had recovered from AC220-treated revealed no mutations in the TK domain, indicating (without wishing to be bound by theory) that AC220 resistance does not appear to be due to diminished binding to FLT3-ITD.

Figure 9:
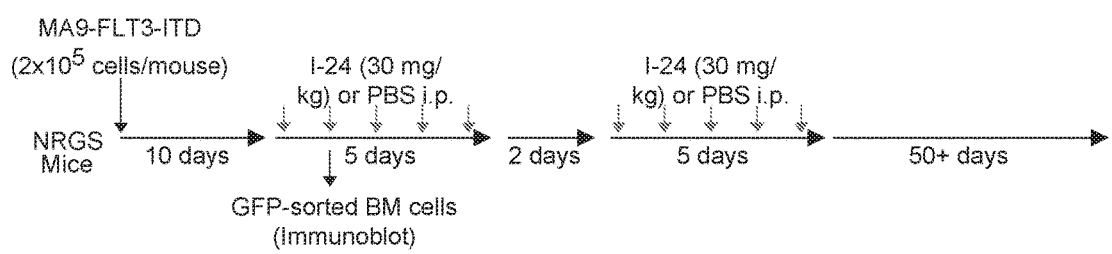
FIG. 9: Some compounds of Formula (I) can be effective against FLT3-ITD AML xenograft mouse models.
Figure 9:
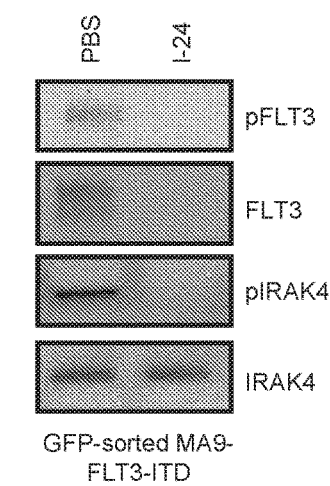
Figure 9:
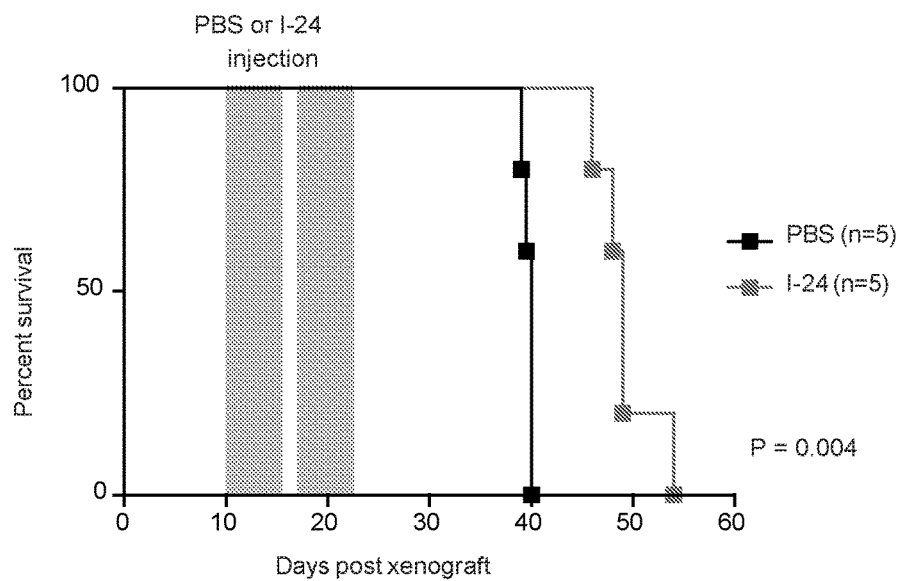

FIG. 9—Methods: (FIG. 9A) Overview of in vivo experimental design: NRGS mice were injected i.v. with MA9-FLT3-ITD cells ($2 \times 10^5$ cells/mouse). After 10 days, PBS or compound I-24 (30 mg/kg) was injected i.p. for 5 daily treatments, followed by a 2 day rest. After the 2nd treatment, one mouse from each group was sacrificed and MA9-FLT3-ITD (GFP+) cells were isolated from the bone marrow ("BM") by flow sorting for immunoblotting of FLT3 and IRAK4. A second cycle of daily injections of PBS or compound I-24 for 5 days, followed by daily monitoring of morbidity. (FIG. 9B) Immunoblot analysis of sorted (GFP+) MA9-FLT3-ITD BM cells from xenografted mice after 2 doses of compound I-24. (FIG. 9C) Overall survival of NRGS mice xenografted with MA9-FLT3-ITD treated with compound I-24 or PBS.

FIG. 9—Results & Discussion: Some compounds of Formula (I) can be effective against FLT3-ITD AML xenograft mouse models. We next assessed the in vivo efficacy of compound I-24 using a human xenograft model of FLT3-ITD AML in NOD.Rag1−/−;γcnull mice that express human IL-3, human granulocyte/macrophage-stimulating factor (GM-CSF) and human stem cell factor (SCF) (NRGS). NRGS mice are radioresistant and have been shown to be a model for AML when engrafted with MA9 FLT3-ITD cells. MLL-AF9 FLT3-ITD cells ($2 \times 10^5$ cells per mouse) were injected via tail vein into NRGS mice (n=12). The cells were allowed to engraft for 10 days. The mice were then treated with PBS (n=6) or compound I-24 (30 mg/kg) (n=6) once daily, intraperitoneally (IP), on days 10-14 and 17-21 post-xenograft (FIG. 8A). On day 12, total bone marrow was collected from the PBS and compound I-24 group and GFP+ cells were isolated by flow cytometry. FLT3 and IRAK4 phosphorylation was evaluated by immunoblotting (FIG. 9B). IP delivery of compound I-24 resulted in reduction of FLT3 and IRAK phosphorylation. To determine the efficacy of compound I-24, NRGS xenografted mice were continually monitored for evidence of AML. As expected, the PBS-treated mice developed AML, as evident by infiltration of leukemic cells into the BM, spleen, and lungs, beginning at Day 38 (median survival of 40 days). In contrast, compound I-24 treatment extended median survival to 49 days (p=0.004) (FIG. 9C).

Figure 10:
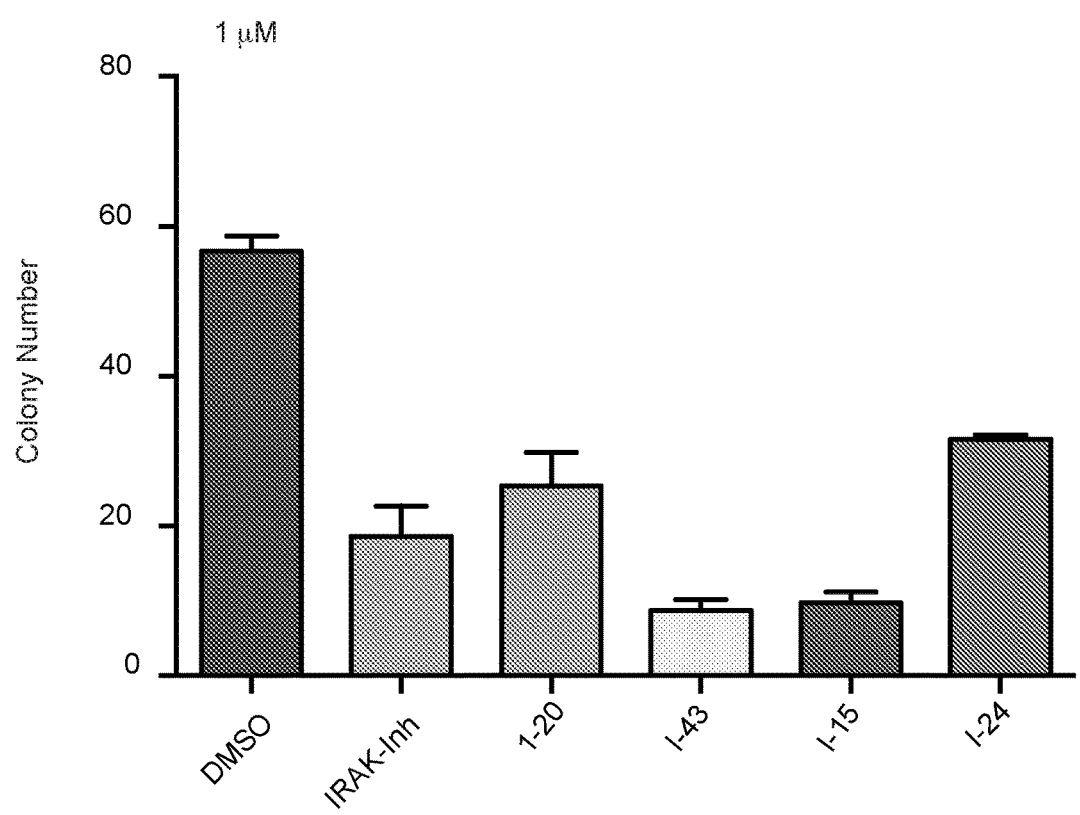
FIG. 10: Some compounds of Formula (I) can be effective against MDS cell function and viability.
Figure 10:
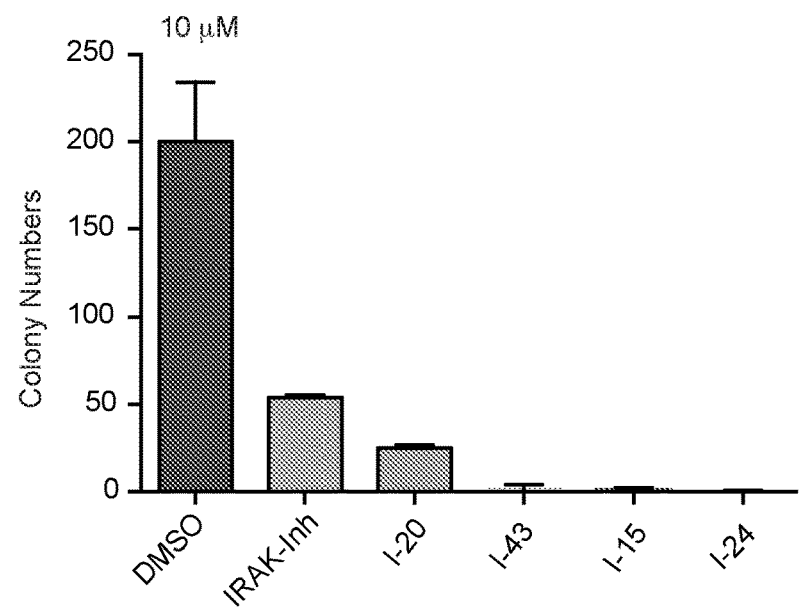
Figure 10:
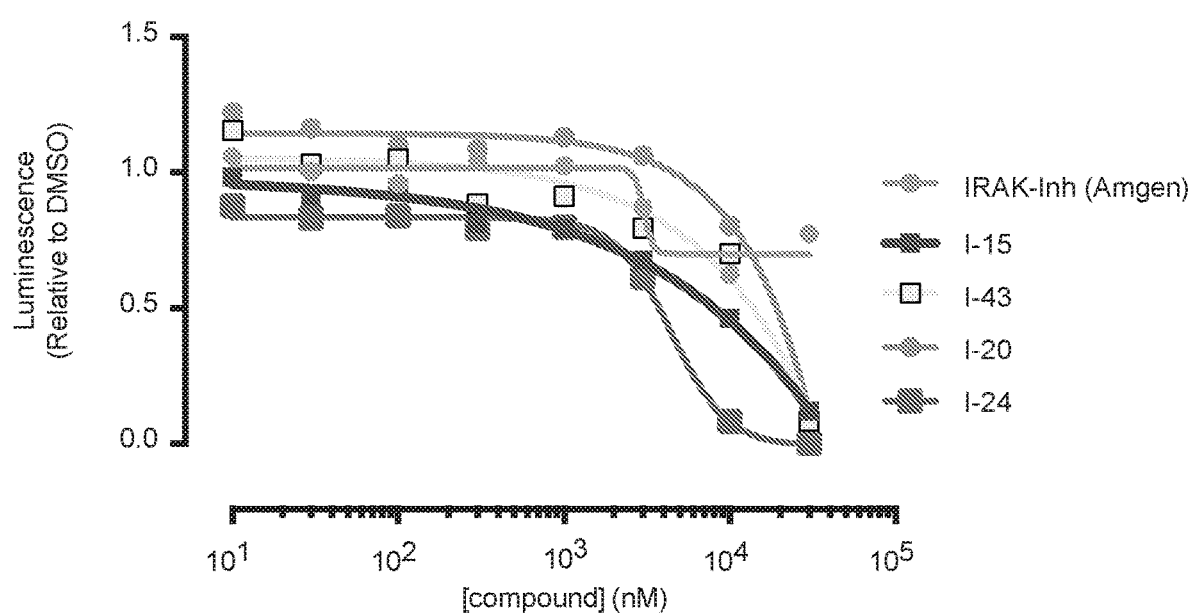

FIG. 10—Methods: (FIG. 10A) Colony formation of MDSL cells was determined in methylcellulose supplemented with 1 μM or 10 μM of the indicated compounds. Colony formation was determined after 10 days. (FIG. 10B) MDSL cells were treated with the indicated compounds for 72 hours. Cell-titer glow relative response values represent normalized growth compared to control cells (DMSO) based on luminescence intensities.

FIG. 10—Results & Discussion: Some compounds of Formula (I) can be effective against MDS cell function and viability. IRAK1 and IRAK4 are hyperactivated in MDS patients. The consequences of treating MDS cells with compounds of Formula (I) were performed by measuring viability and function of a patient-derived MDS cell line (MDSL), which exhibits activated IRAK1 and IRAK4. The effect of the IRAK inhibitors on MDS progenitor function was evaluated in methylcellulose. All four compounds tested inhibited colony formation of MDSL cells, at 10 μM, all are more potent than the commercially-available IRAK1/4 inhibitor. Compound I-24 showed increased ability to inhibit MDSL growth compared to IRAK-Inh. Therefore in addi-

What is claimed is:

1. A compound of Formula (I):

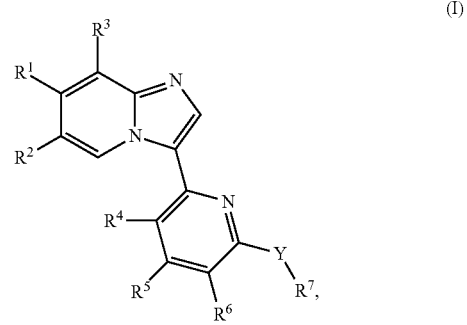

or a pharmaceutically acceptable salt or stereoisomer thereof,
wherein:
$R^1$ is H, halogen, $C_1$-$C_7$ alkyl, $C_2$-$C_7$ alkenyl, $C_2$-$C_7$ alkynyl, OH, or $C_1$-$C_6$ alkoxy, wherein the $C_1$-$C_7$ alkyl, $C_2$-$C_7$ alkenyl, $C_2$-$C_7$ alkynyl, or $C_1$-$C_6$ alkoxy is optionally substituted with one or more substituents independently selected from the group consisting of halogen, $NO_2$, CN, $CH_3$, $CH_2CH_3$, C≡CH, C(O)H, C(O)OH, OH, $SO_3H$, and morpholinyl;

$R^2$ is H, halogen, CN, $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl, wherein the $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl is optionally substituted with one or more substituents independently selected from the group consisting of halogen, $NO_2$, CN, $C_1$-$C_3$ alkyl, $C_1$-$C_3$ perfluorinated alkyl, C≡CH, $CH_2C$≡CH, C≡$CCH_3$, C(O)H, $C(O)NH_2$, $C(O)N(CH_3)_2$, C(O)OH, C(O)-morpholin-4-yl, $NH_2$, $N(CH_3)_2$, OH, $C_1$-$C_3$ alkoxy, $SO_3H$, heterocyclyl, aryl, and heteroaryl;

$R^3$ is H, halogen, $C_1$-$C_3$ alkyl, $C_2$-$C_3$ alkenyl, $C_2$-$C_3$ alkynyl, OH, or $C_1$-$C_2$ alkoxy, wherein the $C_1$-$C_3$ alkyl, $C_2$-$C_3$ alkenyl, $C_2$-$C_3$ alkynyl, or $C_1$-$C_2$ alkoxy is optionally substituted with one or more substituents independently selected from the group consisting of halogen, CN, $CH_3$, $CH_2CH_3$, C≡CH, C(O)H, C(O)OH, OH, and $SO_3H$;

$R^4$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;

$R^5$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;

$R^6$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;

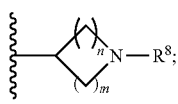

R⁷ is
R⁸ is H, CN, NO₂, C₁-C₄ alkyl, C₂-C₄ alkenyl, C₂-C₄ alkynyl, C(O)H, C(O)CH₃, C(O)CH₂CN, C(O)-phenyl, C(O)OH, or phenyl-CH₃;
Y is —NH—, —N(CH₃)—, —N(CH₂CH₃)—, —N(CH₂CH₂CH₃)—, —N[CH(CH₃)₂]—, or —O—;
m is 0, 1, 2, 3, 4, or 5; and
n is 0, 1, 2, 3, 4, or 5;
with the provisos that:
(1) the sum of m and n is at least 1; and
(2) when R¹ is H, at least one of R⁴, R⁵, or R⁶ is F, Cl, Br, CH₃, CF₃, or OCH₃.

2. The compound of claim 1, or a pharmaceutically acceptable salt or stereoisomer thereof, wherein R¹ is H, halogen, C₁-C₇ alkyl, OH, or C₁-C₆ alkoxy, wherein the C₁-C₇ alkyl or C₁-C₆ alkoxy is optionally substituted with one or more substituents independently selected from the group consisting of halogen, NO₂, CN, CH₃, CH₂CH₃, C≡CH, C(O)H, C(O)OH, OH, SO₃H, and morpholinyl.

3. The compound of claim 2, or a pharmaceutically acceptable salt or stereoisomer thereof, wherein R¹ is halogen, C₁-C₇ alkyl, OH, or C₁-C₆ alkoxy, wherein the C₁-C₇ alkyl or C₁-C₆ alkoxy is optionally substituted with one or more substituents independently selected from the group consisting of halogen, NO₂, CN, CH₃, CH₂CH₃, C≡CH, C(O)H, C(O)OH, OH, SO₃H, and morpholinyl.

4. The compound of claim 2, or a pharmaceutically acceptable salt or stereoisomer thereof, wherein R¹ is Cl, CH₃, OCH₃, or OCH₂CH₂-morpholinyl.

5. The compound of claim 1, or a pharmaceutically acceptable salt or stereoisomer thereof, wherein R² is halogen, CN, C₁-C₇ alkyl, C₂-C₇ alkenyl, C₂-C₇ alkynyl, C(O)H, C(O)OH, OH, C₁-C₆ alkoxy, cycloalkyl, heterocyclyl, aryl, or heteroaryl, wherein the C₁-C₇ alkyl, C₂-C₇ alkenyl, C₂-C₇ alkynyl, C(O)H, C(O)OH, C₁-C₆ alkoxy, cycloalkyl, heterocyclyl, aryl, or heteroaryl is optionally substituted with one or more substituents independently selected from the group consisting of halogen, NO₂, CN, C₁-C₃ alkyl, C₁-C₃ perfluorinated alkyl, C≡CH, CH₂C≡CH, C≡CCH₃, C(O)H, C(O)NH₂, C(O)N(CH₃)₂, C(O)OH, C(O)-morpholin-4-yl, NH₂, N(CH₃)₂, OH, C₁-C₃ alkoxy, SO₃H, heterocyclyl, aryl, and heteroaryl.

6. The compound of claim 1, or a pharmaceutically acceptable salt or stereoisomer thereof, wherein R² is C₁-C₇ alkyl, C₂-C₇ alkenyl, C₂-C₇ alkynyl, C(O)H, C(O)OH, C₁-C₆ alkoxy, cycloalkyl, heterocyclyl, aryl, or heteroaryl, wherein the C₁-C₇ alkyl, C₂-C₇ alkenyl, C₂-C₇ alkynyl, C(O)H, C(O)OH, C₁-C₆ alkoxy, cycloalkyl, heterocyclyl, aryl, or heteroaryl is optionally substituted with one or more substituents independently selected from the group consisting of halogen, NO₂, CN, C₁-C₃ alkyl, C₁-C₃ perfluorinated alkyl, C≡CH, CH₂C≡CH, C≡CCH₃, C(O)H, C(O)NH₂, C(O)N(CH₃)₂, C(O)OH, C(O)-morpholin-4-yl, NH₂, N(CH₃)₂, OH, C₁-C₃ alkoxy, SO₃H, piperidinyl, piperazinyl, morpholinyl, and pyrrolyl.

7. The compound of claim 1, or a pharmaceutically acceptable salt or stereoisomer thereof, wherein R² is H, halogen, CN, C₁-C₇ alkyl, C(O)H, C(O)OH, OH, C₁-C₆ alkoxy, cycloalkyl, heterocyclyl, aryl, or heteroaryl, wherein the C₁-C₇ alkyl, C(O)H, C(O)OH, OH, C₁-C₆ alkoxy, cycloalkyl, heterocyclyl, aryl, or heteroaryl is optionally substituted with one or more substituents independently selected from the group consisting of halogen, NO₂, CN, C₁-C₃ alkyl, C₁-C₃ perfluorinated alkyl, C≡CH, CH₂C≡CH, C≡CCH₃, C(O)H, C(O)NH₂, C(O)N(CH₃)₂, C(O)OH, C(O)-morpholin-4-yl, NH₂, N(CH₃)₂, OH, C₁-C₃ alkoxy, SO₃H, heterocyclyl, aryl, and heteroaryl.

8. The compound of claim 1, or a pharmaceutically acceptable salt or stereoisomer thereof, wherein R² is Cl, CN, CH₃, CF₃, CF₂CF₃, C≡CH, C(O)NH₂, C(O)N(CH₃)₂, C(O)-morpholin-4-yl, OCH₃, OCH₂CH₃, OCH₂CH₂-morpholin-4-yl, 4-ethylpiperazin-1-yl, 1H-pyrrol-3-yl, pyrazol-3-yl, 1H-pyrazol-4-yl, 1-methylpyrazol-4-yl, 1-(morpholin-4-yl)pyrazol-4-yl, 3,5-dimethylpyrazol-4-yl, 3,5-dimethylisoxazol-4-yl, tetrazol-5-yl, pyridin-3-yl, pyridin-4-yl, or 2-methoxypyridin-5-yl.

9. The compound of claim 1, or a pharmaceutically acceptable salt or stereoisomer thereof, wherein R³ is H, halogen, C₁-C₃ alkyl, OH, or C₁-C₂ alkoxy, wherein the C₁-C₃ alkyl or C₁-C₂ alkoxy is optionally substituted with one or more substituents independently selected from the group consisting of halogen, CN, CH₃, CH₂CH₃, C≡CH, C(O)H, C(O)OH, OH, and SO₃H.

10. The compound of claim 9, or a pharmaceutically acceptable salt or stereoisomer thereof, wherein R³ is H or OCH₃, wherein the OCH₃ is optionally substituted with one, two or three independently selected halogen substituents.

11. The compound of claim 10, or a pharmaceutically acceptable salt or stereoisomer thereof, wherein R³ is H or OCH₃.

12. The compound of claim 1, or a pharmaceutically acceptable salt or stereoisomer thereof, wherein R⁴ is H, halogen, CN, NO₂, C₁-C₄ alkyl, C(O)H, C(O)OH, OH, C₁-C₃ alkoxy, or SO₃H, wherein the C₁-C₄ alkyl or C₁-C₃ alkoxy is optionally substituted with one or more substituents independently selected from the group consisting of halogen, NO₂, CN, CH₃, CH₂CH₃, C≡CH, C(O)H, C(O)OH, OH, and SO₃H.

13. The compound of claim 12, or a pharmaceutically acceptable salt or stereoisomer thereof, wherein R⁴ is F, Cl, Br, CH₃, CF₃, or OCH₃.

14. The compound of claim 1, or a pharmaceutically acceptable salt or stereoisomer thereof, wherein R⁵ is H, halogen, CN, NO₂, C₁-C₄ alkyl, C(O)H, C(O)OH, OH, C₁-C₃ alkoxy, or SO₃H, wherein the C₁-C₄ alkyl or C₁-C₃ alkoxy is optionally substituted with one or more substituents independently selected from the group consisting of halogen, NO₂, CN, CH₃, CH₂CH₃, C≡CH, C(O)H, C(O)OH, OH, and SO₃H.

15. The compound of claim 14, or a pharmaceutically acceptable salt or stereoisomer thereof, wherein R⁵ is F, Cl, Br, CH₃, CH₂CH₃, or OCH₃.

16. The compound of claim 1, or a pharmaceutically acceptable salt or stereoisomer thereof, wherein R⁶ is H, halogen, CN, NO₂, C₁-C₄ alkyl, C(O)H, C(O)OH, OH, C₁-C₃ alkoxy, or SO₃H, wherein the C₁-C₄ alkyl or C₁-C₃ alkoxy is optionally substituted with one or more substituents independently selected from the group consisting of halogen, NO₂, CN, CH₃, CH₂CH₃, C≡CH, C(O)H, C(O)OH, OH, and SO₃H.

17. The compound of claim 16, or a pharmaceutically acceptable salt or stereoisomer thereof, wherein R⁶ is F, Cl, Br, CH₃, CF₃, or OCH₃.

18. The compound of claim 1, or a pharmaceutically acceptable salt or stereoisomer thereof, wherein R⁷ is:

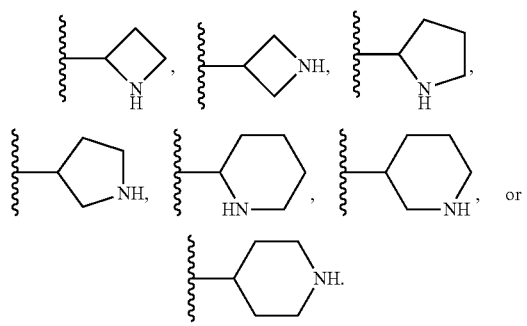

19. The compound of claim 1, or a pharmaceutically acceptable salt or stereoisomer thereof, wherein $R^8$ is H, C≡CH, C(O)CH$_3$, C(O)CH$_2$CN, or C(O)-phenyl.

20. The compound of claim 1, or a pharmaceutically acceptable salt or stereoisomer thereof, wherein Y is —NH—, —N(CH$_3$)—, —N(CH$_2$CH$_3$)—, —N(CH$_2$CH$_2$CH$_3$)—, or —N[CH(CH$_3$)$_2$]—.

21. The compound of claim 20, or a pharmaceutically acceptable salt or stereoisomer thereof, wherein Y is —NH— or —N(CH$_3$)—.

22. The compound of claim 1, or a pharmaceutically acceptable salt or stereoisomer thereof, wherein:

m is 1, 2, or 3; or n is 1, 2, or 3.

23. The compound of claim 1, or a stereoisomer thereof, wherein the compound, or stereoisomer thereof, is selected from the group consisting of:

I-20
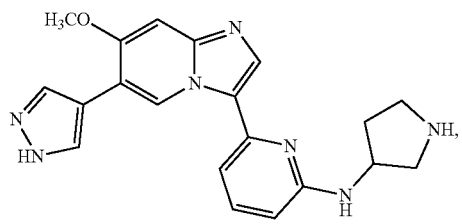

I-21
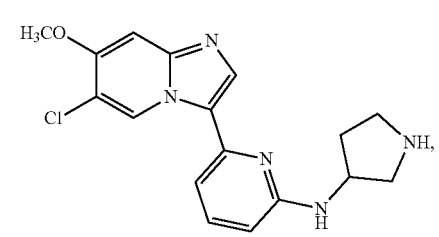

I-22
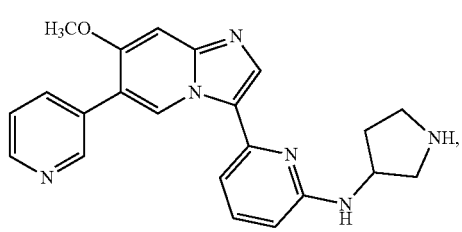

I-23
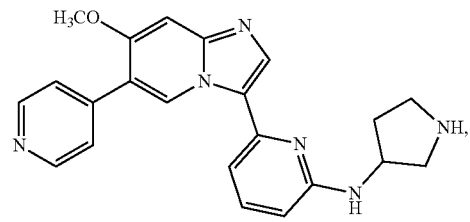

I-24
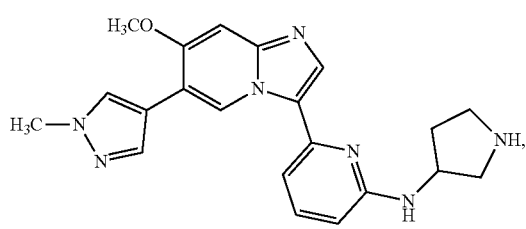

I-25
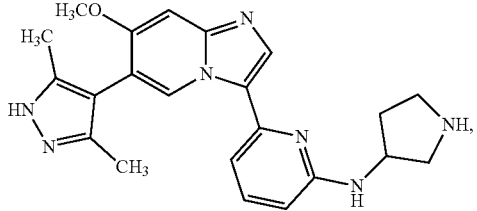

I-26
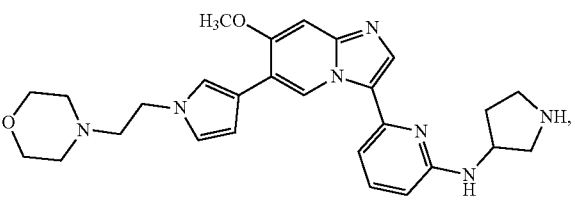

I-27
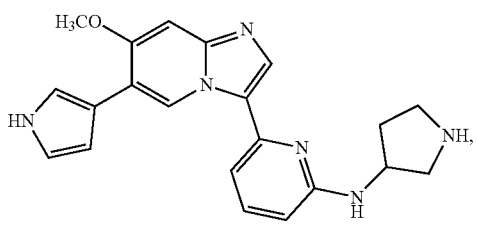

I-28
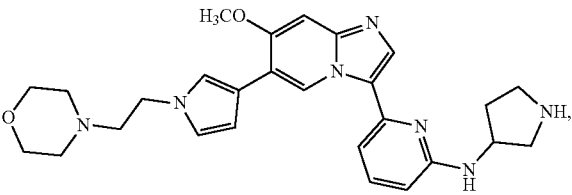

I-29
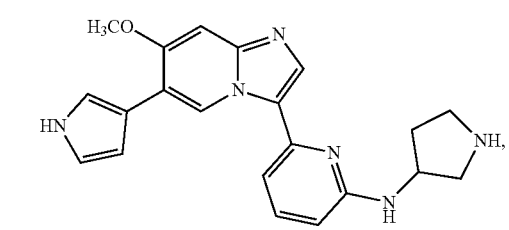

I-30
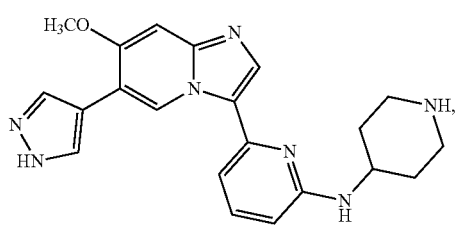
I-31
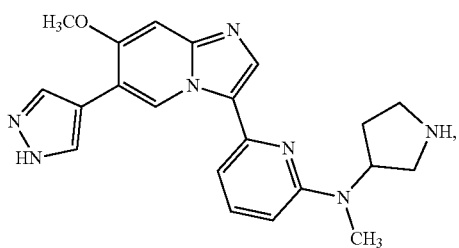
I-32
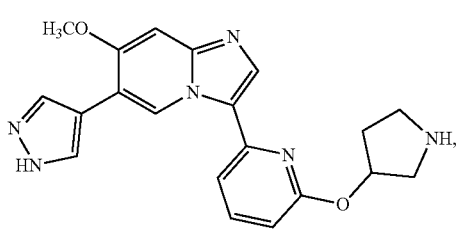
I-33
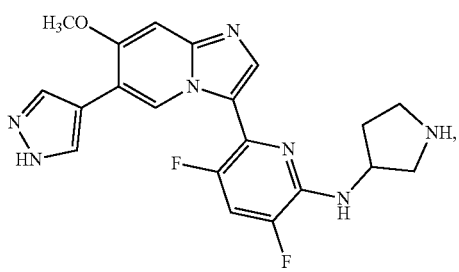
I-34
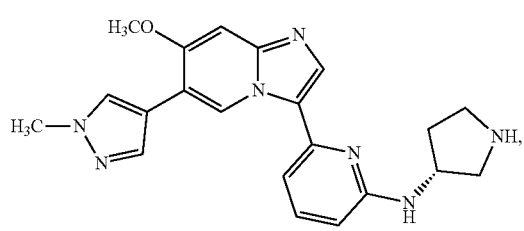
I-35
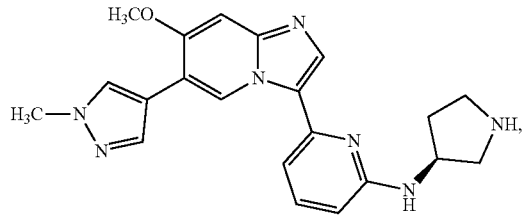
I-36
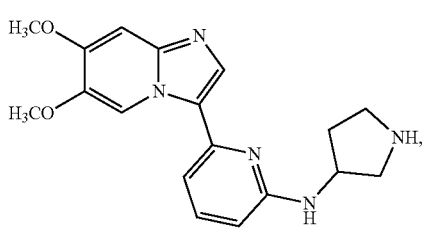
I-37
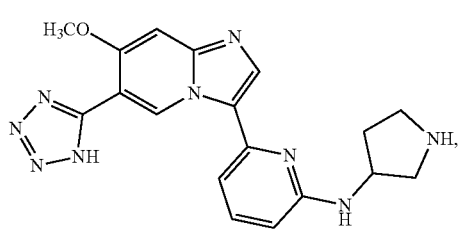
I-39
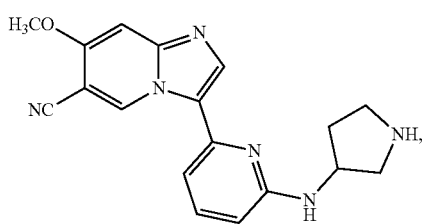
I-40
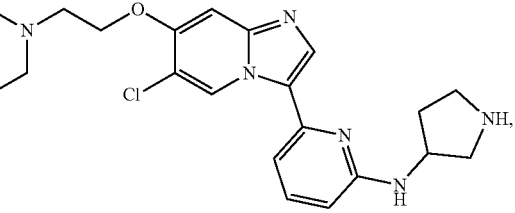
I-41
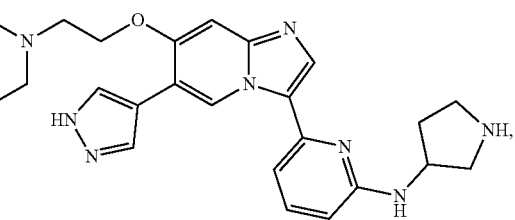
I-47
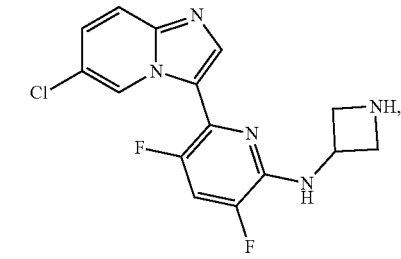

I-48
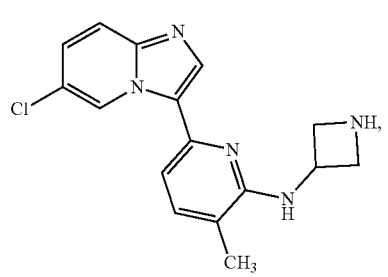
I-49
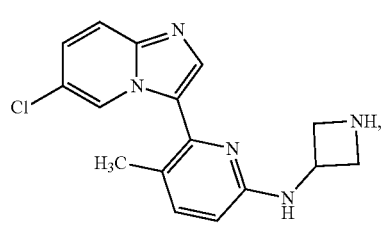
I-50
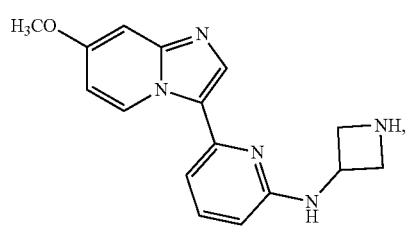
I-53
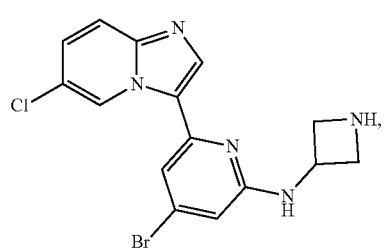
I-55
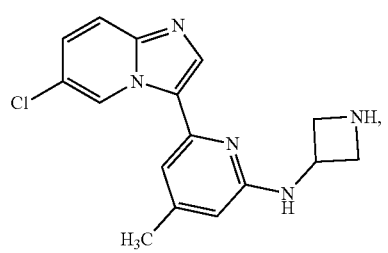
I-56
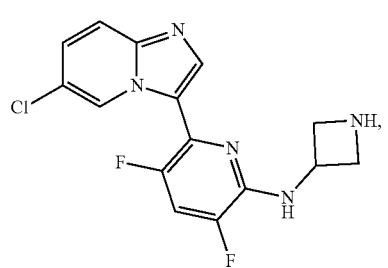
I-61
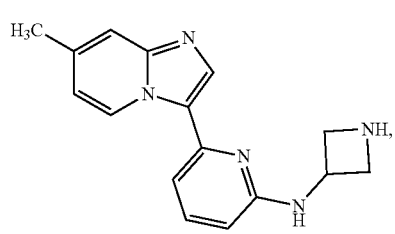
I-62
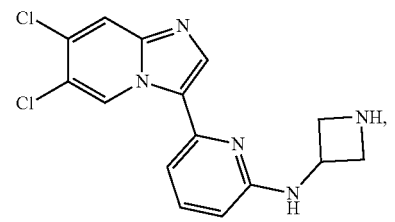
I-63
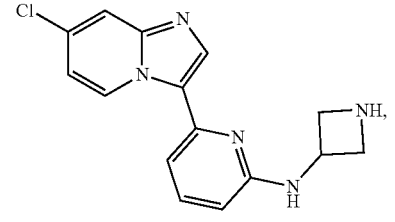
I-65
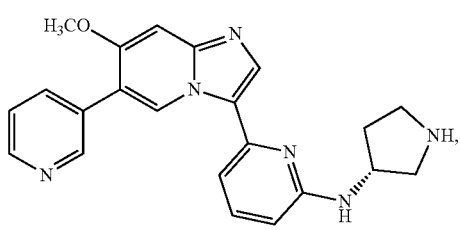
I-66
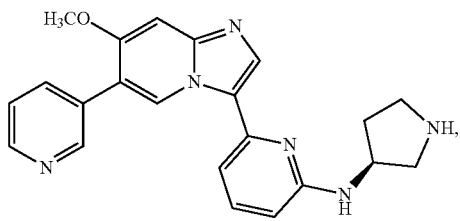
I-67
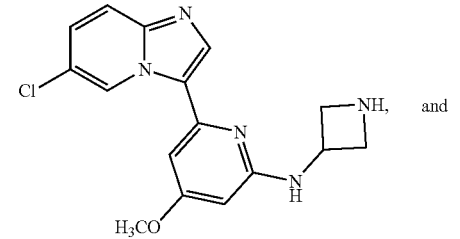
and
I-68
or a pharmaceutically acceptable salt thereof.

24. The compound of claim 23, or a stereoisomer thereof, wherein the compound, or stereoisomer thereof, is selected from the group consisting of:

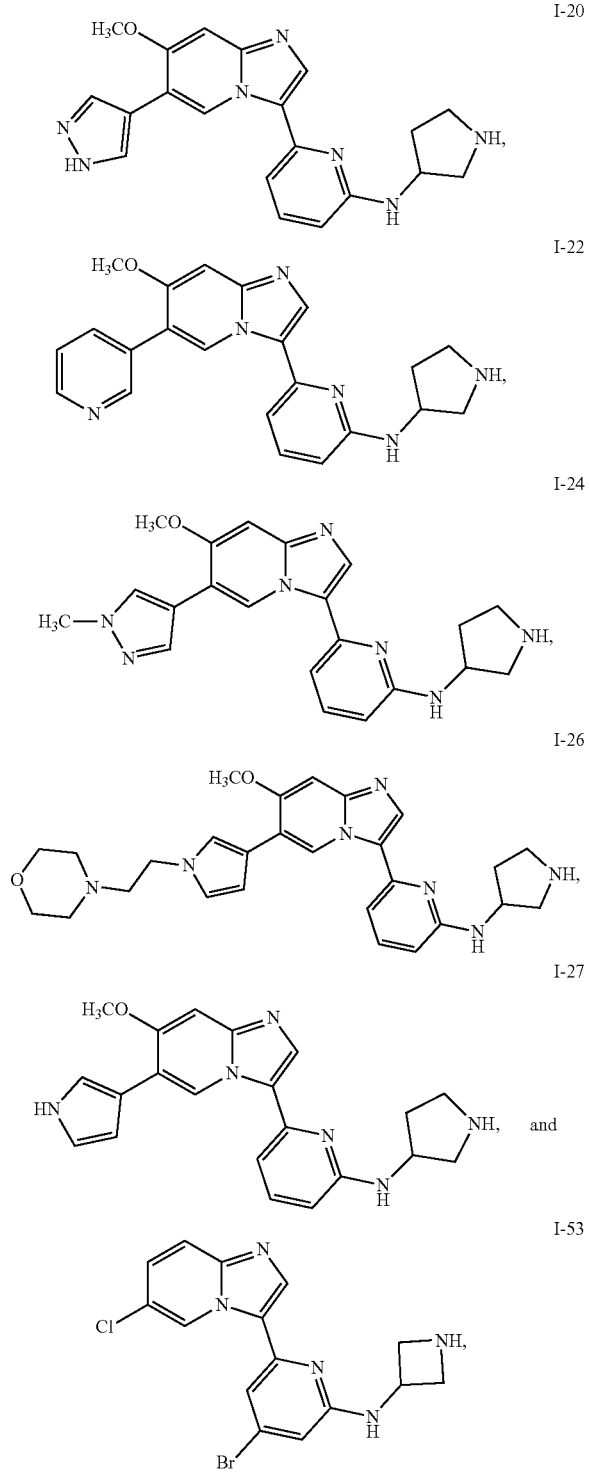

or a pharmaceutically acceptable salt thereof.

25. A pharmaceutical composition comprising a pharmaceutically acceptable carrier and a compound of claim 1, or a pharmaceutically acceptable salt or stereoisomer thereof.

26. A method for inhibiting kinase activity in a human, wherein the method comprises administering to the human in need thereof the pharmaceutical composition of claim 25; wherein the kinase is selected from the group consisting of B-lymphocyte kinase, cyclin dependent kinase 7, cyclin H, fms-like tyrosine kinase 3, interleukin-1 receptor-associated kinase 1, interleukin-1 receptor-associated kinase 4, lymphocyte-specific protein tyrosine kinase, platelet-derived growth factor receptor beta, rearranged during transfection, and serine/arginine-protein kinase 1, or a combination thereof.

27. The method of claim 26, wherein the human has a disease or disorder selected from the group consisting of a blood disorder, a cancer, leukemia, lymphoma, and myelodysplastic syndrome.

28. The method of claim 27, wherein the cancer is bone marrow cancer.

29. The method of claim 27, wherein the leukemia is acute myeloid leukemia.

30. The method of claim 27, wherein the lymphoma is non-Hodgkin lymphoma.

31. The method of claim 30, wherein the non-Hodgkin lymphoma is Waldenstrom macroglobulinemia.

32. The method of claim 27, wherein the human has myelodysplastic syndrome.

33. The method of claim 32, wherein the myelodysplastic syndrome is selected from the group consisting of myelodysplastic syndrome with a mutation in isocitrate dehydrogenase 1, myelodysplastic syndrome with a mutation in isocitrate dehydrogenase 2, and myelodysplastic syndrome with a splicing factor mutation.

34. The method of claim 26, wherein the pharmaceutical composition is administered to the human using intradermal administration, intramuscular administration, intranasal administration, intravenous administration, mucosal administration, oral administration, parenteral administration, subcutaneous administration, sublingual administration, or topical administration, or a combination thereof.

35. The method of claim 26, wherein the pharmaceutical composition is administered to the human in an amount in the range of 0.005 mg/kg human body weight to 50 mg/kg human body weight.

36. The method of claim 26, wherein the compound of claim 1, or pharmaceutically acceptable salt or stereoisomer thereof, present in the pharmaceutical composition is administered to the human in an amount in the range of 0.0001% (w/w) to 99% (w/w).

37. The method of claim 26, wherein the pharmaceutical composition further comprises a formulary ingredient.

38. A method for preparing the compound of claim 1 of Formula (I):

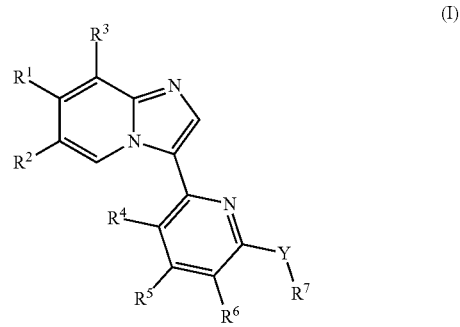

wherein:
  $R^1$ is H, halogen, $C_1$-$C_7$ alkyl, $C_2$-$C_7$ alkenyl, $C_2$-$C_7$ alkynyl, OH, or $C_1$-$C_6$ alkoxy, wherein the $C_1$-$C_7$ alkyl, $C_2$-$C_7$ alkenyl, $C_2$-$C_7$ alkynyl, or $C_1$-$C_6$ alkoxy is optionally substituted with one or more substituents independently selected from the group consisting of halogen, $NO_2$, CN, $CH_3$, $CH_2CH_3$, C≡CH, C(O)H, C(O)OH, OH, $SO_3H$, and morpholinyl;
  $R^2$ is H, halogen, CN, $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl, wherein the $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl is optionally substituted with one or more substituents independently selected from the group consisting of halogen, $NO_2$, CN, $C_1$-$C_3$ alkyl, $C_1$-$C_3$ perfluorinated alkyl, C≡CH, $CH_2$C≡CH, C≡$CCH_3$, C(O)H, C(O)$NH_2$, C(O)N($CH_3$)$_2$, C(O)OH, C(O)-morpholin-4-yl, $NH_2$, N($CH_3$)$_2$, OH, $C_1$-$C_3$ alkoxy, $SO_3H$, heterocyclyl, aryl, and heteroaryl;
  $R^3$ is H, halogen, $C_1$-$C_3$ alkyl, $C_2$-$C_3$ alkenyl, $C_2$-$C_3$ alkynyl, OH, or $C_1$-$C_2$ alkoxy, wherein the $C_1$-$C_3$ alkyl, $C_2$-$C_3$ alkenyl, $C_2$-$C_3$ alkynyl, or $C_1$-$C_2$ alkoxy is optionally substituted with one or more substituents independently selected from the group consisting of halogen, CN, $CH_3$, $CH_2CH_3$, C≡CH, C(O)H, C(O)OH, OH, and $SO_3H$;
  $R^4$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;
  $R^5$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;
  $R^6$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;

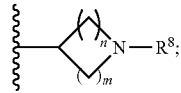

$R^7$ is
    $R^8$ is H, CN, $NO_2$, $C_1$-$C_4$ alkyl, $C_2$-$C_4$ alkenyl, $C_2$-$C_4$ alkynyl, C(O)H, C(O)$CH_3$, C(O)$CH_2$CN, C(O)-phenyl, C(O)OH, or phenyl-$CH_3$;
    Y is —NH—, —N($CH_3$)—, —N($CH_2CH_3$)—, —N($CH_2CH_2CH_3$)—, —N[CH($CH_3$)$_2$]—, or —O—;
    m is 0, 1, 2, 3, 4, or 5; and
    n is 0, 1, 2, 3, 4, or 5;
  with the provisos that:
    (1) the sum of m and n is at least 1; and
    (2) when $R^1$ is H, at least one of $R^4$, $R^5$, or $R^6$ is F, Cl, Br, $CH_3$, $CF_3$, or $OCH_3$;

wherein the method comprises the following steps:
(a) reacting a compound of Formula (II):

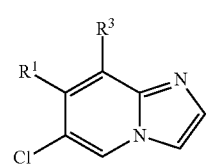

wherein:
  $R^1$ is H, halogen, $C_1$-$C_7$ alkyl, $C_2$-$C_7$ alkenyl, $C_2$-$C_7$ alkynyl, OH, or $C_1$-$C_6$ alkoxy, wherein the $C_1$-$C_7$ alkyl, $C_2$-$C_7$ alkenyl, $C_2$-$C_7$ alkynyl, or $C_1$-$C_6$ alkoxy is optionally substituted with one or more substituents independently selected from the group consisting of halogen, $NO_2$, CN, $CH_3$, $CH_2CH_3$, C≡CH, C(O)H, C(O)OH, OH, $SO_3H$, and morpholinyl; and
  $R^3$ is H, halogen, $C_1$-$C_3$ alkyl, $C_2$-$C_3$ alkenyl, $C_2$-$C_3$ alkynyl, OH, or $C_1$-$C_2$ alkoxy, wherein the $C_1$-$C_3$ alkyl, $C_2$-$C_3$ alkenyl, $C_2$-$C_3$ alkynyl, or $C_1$-$C_2$ alkoxy is optionally substituted with one or more substituents independently selected from the group consisting of halogen, CN, $CH_3$, $CH_2CH_3$, C≡CH, C(O)H, C(O)OH, OH, and $SO_3H$;

with a compound of Formula (III):

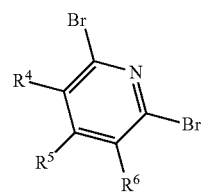

wherein:
  $R^4$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;
  $R^5$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$; and
  $R^6$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;

in the presence of a palladium catalyst, to provide a mixture comprising a compound of Formula (IV):

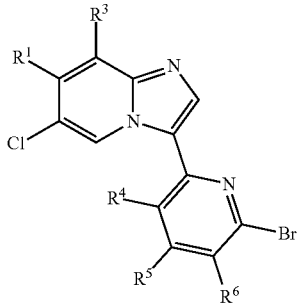

(IV)

wherein:
- $R^1$ is H, halogen, $C_1$-$C_7$ alkyl, $C_2$-$C_7$ alkenyl, $C_2$-$C_7$ alkynyl, OH, or $C_1$-$C_6$ alkoxy, wherein the $C_1$-$C_7$ alkyl, $C_2$-$C_7$ alkenyl, $C_2$-$C_7$ alkynyl, or $C_1$-$C_6$ alkoxy is optionally substituted with one or more substituents independently selected from the group consisting of halogen, $NO_2$, CN, $CH_3$, $CH_2CH_3$, C≡CH, C(O)H, C(O)OH, OH, $SO_3H$, and morpholinyl;
- $R^3$ is H, halogen, $C_1$-$C_3$ alkyl, $C_2$-$C_3$ alkenyl, $C_2$-$C_3$ alkynyl, OH, or $C_1$-$C_2$ alkoxy, wherein the $C_1$-$C_3$ alkyl, $C_2$-$C_3$ alkenyl, $C_2$-$C_3$ alkynyl, or $C_1$-$C_2$ alkoxy is optionally substituted with one or more substituents independently selected from the group consisting of halogen, CN, $CH_3$, $CH_2CH_3$, C≡CH, C(O)H, C(O)OH, OH, and $SO_3H$;
- $R^4$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;
- $R^5$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$; and
- $R^6$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;

(b) reacting the mixture comprising the compound of Formula (IV) above with a compound of Formula (V):

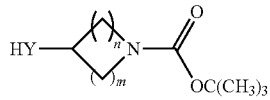

(V)

wherein:
- Y is —NH—, —N($CH_3$)—, —N($CH_2CH_3$)—, —N($CH_2CH_2CH_3$)—, —N[CH($CH_3$)$_2$]—, or —O—;
- m is 0, 1, 2, 3, 4, or 5; and
- n is 0, 1, 2, 3, 4, or 5;

in the presence of a palladium catalyst or copper (I) catalyst, to provide a mixture comprising a compound of Formula (VI):

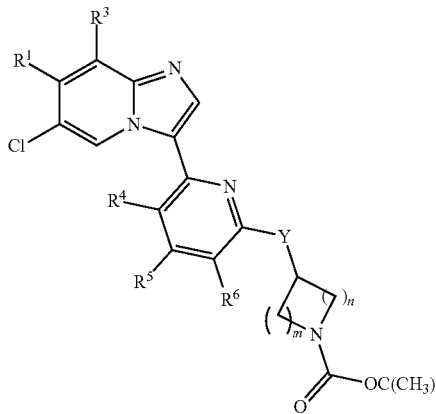

(VI)

wherein:
- $R^1$ is H, halogen, $C_1$-$C_7$ alkyl, $C_2$-$C_7$ alkenyl, $C_2$-$C_7$ alkynyl, OH, or $C_1$-$C_6$ alkoxy, wherein the $C_1$-$C_7$ alkyl, $C_2$-$C_7$ alkenyl, $C_2$-$C_7$ alkynyl, or $C_1$-$C_6$ alkoxy is optionally substituted with one or more substituents independently selected from the group consisting of halogen, $NO_2$, CN, $CH_3$, $CH_2CH_3$, C≡CH, C(O)H, C(O)OH, OH, $SO_3H$, and morpholinyl;
- $R^3$ is H, halogen, $C_1$-$C_3$ alkyl, $C_2$-$C_3$ alkenyl, $C_2$-$C_3$ alkynyl, OH, or $C_1$-$C_2$ alkoxy, wherein the $C_1$-$C_3$ alkyl, $C_2$-$C_3$ alkenyl, $C_2$-$C_3$ alkynyl, or $C_1$-$C_2$ alkoxy is optionally substituted with one or more substituents independently selected from the group consisting of halogen, CN, $CH_3$, $CH_2CH_3$, C≡CH, C(O)H, C(O)OH, OH, and $SO_3H$;
- $R^4$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;
- $R^5$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$; and
- $R^6$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3H$, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3H$;
- Y is —NH—, —N($CH_3$)—, —N($CH_2CH_3$)—, —N($CH_2CH_2CH_3$)—, —N[CH($CH_3$)$_2$]—, or —O—;
- m is 0, 1, 2, 3, 4, or 5; and
- n is 0, 1, 2, 3, 4, or 5;

(c) optionally reacting the mixture comprising the compound of Formula (VI) above with a compound of Formula (VII):

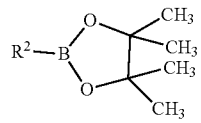

(VII)

wherein:

$R^2$ is H, halogen, CN, $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl, wherein the $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl is optionally substituted with one or more substituents independently selected from the group consisting of halogen, $NO_2$, CN, $C_1$-$C_3$ alkyl, $C_1$-$C_3$ perflourinated alkyl, C≡CH, $CH_2$C≡CH, C≡$CCH_3$, C(O)H, C(O)$NH_2$, C(O)N($CH_3$)$_2$, C(O)OH, C(O)-morpholin-4-yl, $NH_2$, N($CH_3$)$_2$, OH, $C_1$-$C_3$ alkoxy, $SO_3$H, heterocyclyl, aryl, and heteroaryl;

in the presence of a palladium catalyst, to provide a mixture comprising a compound of Formula (VIII):

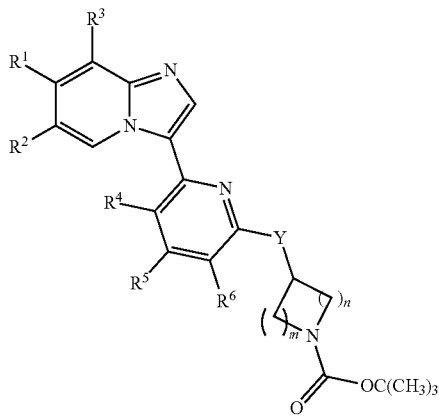

(VIII)

wherein:

$R^1$ is H, halogen, $C_1$-$C_7$ alkyl, $C_2$-$C_7$ alkenyl, $C_2$-$C_7$ alkynyl, OH, or $C_1$-$C_6$ alkoxy, wherein the $C_1$-$C_7$ alkyl, $C_2$-$C_7$ alkenyl, $C_2$-$C_7$ alkynyl, or $C_1$-$C_6$ alkoxy is optionally substituted with one or more substituents independently selected from the group consisting of halogen, $NO_2$, CN, $CH_3$, $CH_2CH_3$, C≡CH, C(O)H, C(O)OH, OH, $SO_3$H, and morpholinyl;

$R^2$ is H, halogen, CN, $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl, wherein the $C_1$-$C_7$ alkyl, $C_2$-$C_7$ alkenyl, $C_2$-$C_7$ alkynyl, C(O)H, C(O)OH, OH, $C_1$-$C_6$ alkoxy, cycloalkyl, heterocyclyl, aryl, or heteroaryl is optionally substituted with one or more substituents independently selected from the group consisting of halogen, $NO_2$, CN, $C_1$-$C_3$ alkyl, $C_1$-$C_3$ perflourinated alkyl, C≡CH, $CH_2$C≡CH, C≡$CCH_3$, C(O)H, C(O)$NH_2$, C(O)N($CH_3$)$_2$, C(O)OH, C(O)-morpholin-4-yl, $NH_2$, N($CH_3$)$_2$, OH, $C_1$-$C_3$ alkoxy, $SO_3$H, heterocyclyl, aryl, and heteroaryl;

$R^3$ is H, halogen, $C_1$-$C_3$ alkyl, $C_2$-$C_3$ alkenyl, $C_2$-$C_3$ alkynyl, OH, or $C_1$-$C_2$ alkoxy, wherein the $C_1$-$C_3$ alkyl, $C_2$-$C_3$ alkenyl, $C_2$-$C_3$ alkynyl, or $C_1$-$C_2$ alkoxy is optionally substituted with one or more substituents independently selected from the group consisting of halogen, CN, $CH_3$, $CH_2CH_3$, C≡CH, C(O)H, C(O)OH, OH, and $SO_3$H;

$R^4$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3$H, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3$H;

$R^5$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3$H, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3$H; and $R^6$ is H, halogen, CN, $NO_2$, $C_1$-$C_4$ alkyl, $C_2$-$C_4$ alkenyl, $C_2$-$C_4$ alkynyl, C(O)H, C(O)OH, OH, $C_1$-$C_3$ alkoxy, or $SO_3$H, wherein the $C_1$-$C_4$ alkyl, $C_2$-$C_4$ alkenyl, $C_2$-$C_4$ alkynyl, or $C_1$-$C_3$ alkoxy is optionally substituted with one or more substituents independently selected from the group consisting of halogen, $NO_2$, CN, $CH_3$, $CH_2CH_3$, C≡CH, C(O)H, C(O)OH, OH, and $SO_3$H;

Y is —NH—, —N($CH_3$)—, —N($CH_2CH_3$)—, —N($CH_2CH_2CH_3$)—, —N[CH($CH_3$)$_2$]—, or —O—;

m is 0, 1, 2, 3, 4, or 5; and n is 0, 1, 2, 3, 4, or 5;

(d) deprotecting the compound of Formula (VI) above or the compound of Formula (VIII) above in the presence of a mixture comprising trifluoroacetic acid and dichloromethane; and (e) recovering the compound of Formula (I) above.

* * * * *